(12) United States Patent
Jenkins et al.

(10) Patent No.: US 7,194,301 B2
(45) Date of Patent: Mar. 20, 2007

(54) METHOD FOR SCREENING AND TREATING PATIENTS AT RISK OF MEDICAL DISORDERS

(75) Inventors: David A. Jenkins, Flanders, NJ (US); Roland Maude-Griffin, Edina, MN (US)

(73) Assignee: Transneuronic, Inc., Mt. Arlington, NJ (US)

( * ) Notice: Subject to any disclaimer, the term of this patent is extended or adjusted under 35 U.S.C. 154(b) by 176 days.

(21) Appl. No.: 10/955,591

(22) Filed: Sep. 30, 2004

(65) Prior Publication Data

US 2005/0080462 A1    Apr. 14, 2005

Related U.S. Application Data

(60) Provisional application No. 60/508,280, filed on Oct. 6, 2003.

(51) Int. Cl.
*A61N 1/00* (2006.01)

(52) U.S. Cl. .......................................................... 607/2

(58) Field of Classification Search ....................... 607/2
See application file for complete search history.

(56) References Cited

U.S. PATENT DOCUMENTS

| | | | |
|---|---|---|---|
| 4,607,639 A | 8/1986 | Tanogho et al. |
| 5,188,104 A | 2/1993 | Wernicke et al. |
| 5,292,344 A | 3/1994 | Douglas |
| 5,423,872 A | 6/1995 | Cigaina |
| 5,690,691 A | 11/1997 | Chen et al. |
| 5,836,994 A | 11/1998 | Bourgeois |
| 5,861,014 A | 1/1999 | Familoni |
| 6,041,258 A | 3/2000 | Cigaina et al. |
| 6,091,992 A | 7/2000 | Bourgeois et al. |
| 6,115,635 A | 9/2000 | Bourgeois |
| 6,321,124 B1 | 11/2001 | Cigaina |
| 6,498,993 B1 | 12/2002 | Chen et al. |
| 6,519,534 B2 | 2/2003 | Bonissone et al. |
| 6,542,776 B1 | 4/2003 | Gordon et al. |
| 6,600,953 B2 | 7/2003 | Flesler et al. |
| 6,615,084 B1 | 9/2003 | Cigaina |
| 6,889,076 B2 | 5/2005 | Cigaina |
| 2004/0015201 A1 | 1/2004 | Greenstein |

(Continued)

OTHER PUBLICATIONS

RAND 36 Item Health Survey 1.0 Questionnaire Items, RAND Health, a printout of: http://www.rand.org/health/surveys/st36item/questionnaire.html, 5 pages, Jun. 12, 2003.

(Continued)

*Primary Examiner*—Robert Pezzuto
*Assistant Examiner*—Yun Haeng Lee
(74) *Attorney, Agent, or Firm*—Fitch, Even, Tabin & Flannery

(57) ABSTRACT

Method for screening patients to predict which patients at risk of a medical disorder, such as morbid obesity, gastrointestinal problems, or gastroesophageal problems, will be responders, and conversely, which patients will not, to achieve a favorable outcome from therapy for that disorder. This method supports an intervention strategy for patients having weight or gastrointestinal problems that will cut health costs. It enables patients and care-givers alike to more efficiently use their time, efforts and resources by enabling an early selection of an appropriate treatment modality for a given patient. Its application also extends to other implantable medical devices and therapies using them.

43 Claims, 25 Drawing Sheets

U.S. PATENT DOCUMENTS

2004/0088022 A1    5/2004    Chen

OTHER PUBLICATIONS

Breiman, L., "Bagging Predictors," Machine Learning, 24(2), pp. 123-140, 1996.

Breiman, L., "Arcing Classifiers," Annals of Statistics 26, pp. 801-849, 1998.

Breiman, L., et al., "Chapter 8: Regression Trees," Classification and Regression Trees, pp. 216-265, Chapman & Hall/CRC, New York NY, 1984.

Hastie, T., et al., "Chapter 8, Section 7: Bagging," The Elements of Statistical Learning: Data Mining, Inference and Prediction; pp. 246-253, Springer, New York NY, 2001.

Hastie, T., et al., "Chapter 9: Additive Models, Trees and Related Methods," The Elements of Statistical Learning: Data Mining, Inference and Prediction; pp. 257-298, Springer, New York NY, 2001.

Hastie, T., et al., "Chapter 10: Boosting and Additive Trees," The Elements of Statistical Learning: Data Mining, Inference and Prediction; pp. 299-345, Springer, New York NY, 2001.

CART® for Windows User's Guide—An Implementation of the Original CART Technology—Salford Systems CART® version 5.0, pp. i-xii and pp. 1-295, Salford Systems, San Diego, CA, 2002.

Efron, B. et al., "Chapter 17: Cross-Validation and Other Estimates of Prediction Error," An Introduction to the Bootstrap, pp. 237-257, Chapman Hall, New York NY, 1993.

Dudoit, S. et al., "Asymptotics of Cross-Validated Risk Estimation In Estimator Selection and Performance Assessment," UC Berkeley Division of Biostatistics Working Paper Series, Paper 126, pp. 1-35, 2003.

Hatsie, T., et al., "Chapter 7: Model Assessment and Selection," The Elements of Statistical Learning: Data Mining, Inference and Prediction; pp. 193-224, Springer, New York NY, 2001.

Shao, J., "Linear Model Selection by Cross-Validation," JASA, 88(422), pp. 486-494, Jun. 1993.

de Zwaan, M., et al., "Two Measures of Health-Related Quality of Life in Morbid Obesity," Obesity Research, 10(11), pp. 1143-1151, Nov. 2002.

Hays, R., et al., "A Microcomputer Program (SF-36.EXE) that Generates SAS Code for Scoring the SF-36 Health Survey," SAS Users Group International SUG122 Proceedings, pp. 1128-1132, SAS Institute, Cary, NC, 1997.

"Medical Outcomes Trust . . . SF-36 Standard US Version 1.0," pp. 1-6, Medical Outcomes Trust, Waltham, MA, 1992.

Wadden, T., et al., "Assessment of Quality of Life in Obese Individuals," Obesity Research , 10(Suppl. 1), pp. 50S-57S, Nov. 2002.

Ware, Jr., J., et al., "Overview of the SF-36 Health Survey and the International Quality of Life Assessment (IQOLA) Project," Journal of Clinical Epidemiology, 51(11), pp. 903-912, Jul. 1998.

Ware, Jr., J., et al., "The Equivalence of SF-36 Summary Health Scores Estimated Using Standard and Country-Specific Algorithms in 10 Countries: Results from an IQOLA Project," Journal of Clinical Epidemiology, 51(11), pp. 1167-1170, Jul. 1998.

Ware, Jr., J., "SF-36 Health Survey Update," SPINE, 25(24), pp. 3130-3139, 2000.

Dixon, J. B., et al., "Pre-Operative Predictors of Weight Loss at 1-Year After Lap-Band Surgery," Obesity surgery, 11(2), pp. 200-207, 2001.

Herpertz, S., et al., "Do Psychosocial Variables Predict Weight Loss or Mental Health After Obesity Surgery?" Obesity Research, 12(10), pp. 1554-1569, Oct. 2004.

van Hout, G., et al., "Psychosocial Predictors of Success Following Bariatric Surgery," Obesity Surgery, 15, pp. 552-560, 2005.

Allore, H., et al., "A case study found that a regression tree outperformed multiple linear regression in predicting the relationship between impairments and Social and Productive Activities scores," Journal of Clinical Epidemiology, 58, pp. 154-161, 2005.

Deconinck, E., et al., "Classification of drugs in absorption classes using the classification and regression trees (CART) methodology," Journal of Pharm and Biomed Analysis (article in press), pp. 1-13, accepted Mar. 2005.

Fonarow, G., et al., "Risk Stratification for In-Hospital Mortality in Acutely Decompensated Heart Failure—Classification and Regression Tree Analysis," JAMA, 293(5), pp. 572-580, Aug. 2005.

Friedman, J., et al., "Multiple Additive Regression Trees with Application in Epidemiology," Statistics in Medicine, 22, pp. 1365-1381, 2003.

Haukoos, J.S., et al., "Emergency Department Triage of Patients Infected with HIV," Academic Emergency Medicine, 9(9), pp. 880-888, Sep. 2002.

Marvez, E., et al., "Predicting Adverse Outcomes in a Diagnosis-Based Protocol System for Rapid Sequence Intubation," American Journal of Emergency Medicine, 21(1), pp. 23-29, Jan. 2003.

Newgard, C. D., et al., "Use of Out-Of-Hospital Variables to Predict Severity of Injury in Pediatric Patients Involved in Motor Vehicle Crashes," Annals of Emergency Medicine, 39(5), pp. 481-491, May 2002.

FIG. 2

The SF-36 Version 1.0 Health Survey

INSTRUCTIONS: This survey asks for you views about your health. This information will help keep track of how you feel and how well you are able to do your usual activities. Answer every question by marking the answer as indicated. If you are unsure about how to answer a question, please give the best answer you can.

1. In general, would you say your health is: (circle one)

Excellent................................................. 1
   Very good............................................... 2
   Good ..................................................... 3
   Fair ....................................................... 4
   Poor ...................................................... 5

2. Compared to one year ago, how would you rate your health in general now? (circle one)

Much better now than one year ago....................1
   Somewhat better now than one year ago..............2
   About the same as one year ago.........................3
   Somewhat worse now than one year ago..............4
   Much worse now than one year ago....................5

FIG. 3

3. The following items are about activities you might do during a typical day. Does your health now limit you in these activities? If so, how much? (circle one number on each line)

| ACTIVITIES | Yes, Limited A Lot | Yes, Limited A Little | No, Not Limited At All |
|---|---|---|---|
| a. Vigorous activities, such as running, lifting heavy objects, participating in strenuous sports | 1 | 2 | 3 |
| b. Moderate activities, such as moving a table, pushing a vacuum cleaner, bowling, or playing golf | 1 | 2 | 3 |
| c. Lifting or carrying groceries | 1 | 2 | 3 |
| d. Climbing several flights of stairs | 1 | 2 | 3 |
| e. Climbing one flight of stairs | 1 | 2 | 3 |
| f. Bending, kneeling, or stooping | 1 | 2 | 3 |
| g. Walking more than a mile | 1 | 2 | 3 |
| h. Walking several blocks | 1 | 2 | 3 |
| i. Walking one block | 1 | 2 | 3 |
| j. Bathing or dressing yourself | 1 | 2 | 3 |

FIG. 4

4. During the past 4 weeks, have you had any of the following problems with your work or other regular daily activities as a result of your physical health? (circle one number on each line)

|  | YES | NO |
|---|---|---|
| a. Cut down on the amount of time you spent on work or other activities | 1 | 2 |
| b. Accomplished less than you would like | 1 | 2 |
| c. Were limited in the kind of work or other activities | 1 | 2 |
| d. Had difficulty performing the work or other activities (for example, it took extra effort) | 1 | 2 |

5. During the past 4 weeks, have you had any of the following problems with your work or other regular daily activities as a result of any emotional problems (such as feeling depressed or anxious)? (circle one number on each line)

|  | YES | NO |
|---|---|---|
| a. Cut down on the amount of time you spent on work or other activities | 1 | 2 |
| b. Accomplished less than you would like | 1 | 2 |
| c. Didn't do work or other activities as carefully as usual. | 1 | 2 |

FIG. 5

6. During the past 4 weeks, to what extent has your physical health or emotional problems interfered with your normal social activities with family, friends, neighbors, or groups? (circle one)

Not at all ............................................................. 1
    Slightly ................................................................ 2
    Moderately .......................................................... 3
    Quite a bit ........................................................... 4
    Extremely ............................................................ 5

7. How much bodily pain have you had during the past 4 weeks? (circle one)

None .................................................................... 1
    Very mild ............................................................. 2
    Mild ..................................................................... 3
    Moderate ............................................................. 4
    Severe .................................................................. 5
    Very severe ......................................................... 6

8. During the past 4 weeks, how much did pain interfere with your normal work (including both work outside the home and housework)? (circle one)

Not at all ............................................................. 1
    A little bit ........................................................... 2
    Moderately .......................................................... 3
    Quite a bit ........................................................... 4
    Extremely ............................................................ 5

FIG. 6

9. These questions are about how you feel and how things have been with you during the past 4 weeks. For each question, please give the one answer that comes closest to the way you have been feeling.

| How much of the time during the past 4 weeks (circle one number on each line): | All of the Time | Most of the Time | A Good Bit of the Time | Some of the Time | A Little of the Time | None of the Time |
|---|---|---|---|---|---|---|
| a. Did you feel full of pep? | 1 | 2 | 3 | 4 | 5 | 6 |
| b. Have you been a very nervous person? | 1 | 2 | 3 | 4 | 5 | 6 |
| c. Have you felt so down in the dumps that nothing could cheer you up? | 1 | 2 | 3 | 4 | 5 | 6 |
| d. Have you felt calm and peaceful? | 1 | 2 | 3 | 4 | 5 | 6 |
| e. Did you have a lot of energy? | 1 | 2 | 3 | 4 | 5 | 6 |
| f. Have you felt downhearted and blue? | 1 | 2 | 3 | 4 | 5 | 6 |
| g. Did you feel worn out? | 1 | 2 | 3 | 4 | 5 | 6 |
| h. Have you been a happy person | 1 | 2 | 3 | 4 | 5 | 6 |
| i. Did you feel tired? | 1 | 2 | 3 | 4 | 5 | 6 |

FIG. 7

10. During the past 4 weeks, how much of the time has your physical health or emotional problems interfered with your social activities (like visiting with friends, relatives, etc.)? (circle one)

All of the time ..................................................................1
Most of the time ...............................................................2
Some of the time ...............................................................3
A little of the time .............................................................4
None of the time ................................................................5

11. How TRUE or FALSE is each of the following statements for you?

|  | Definitely True | Mostly True | Don't Know | Mostly False | Definitely False |
|---|---|---|---|---|---|
| a. I seem to get sick a little easier than other people | 1 | 2 | 3 | 4 | 5 |
| b. I am as healthy as anybody I know | 1 | 2 | 3 | 4 | 5 |
| c. I expect my health to get worse | 1 | 2 | 3 | 4 | 5 |
| d. My health is excellent | 1 | 2 | 3 | 4 | 5 |

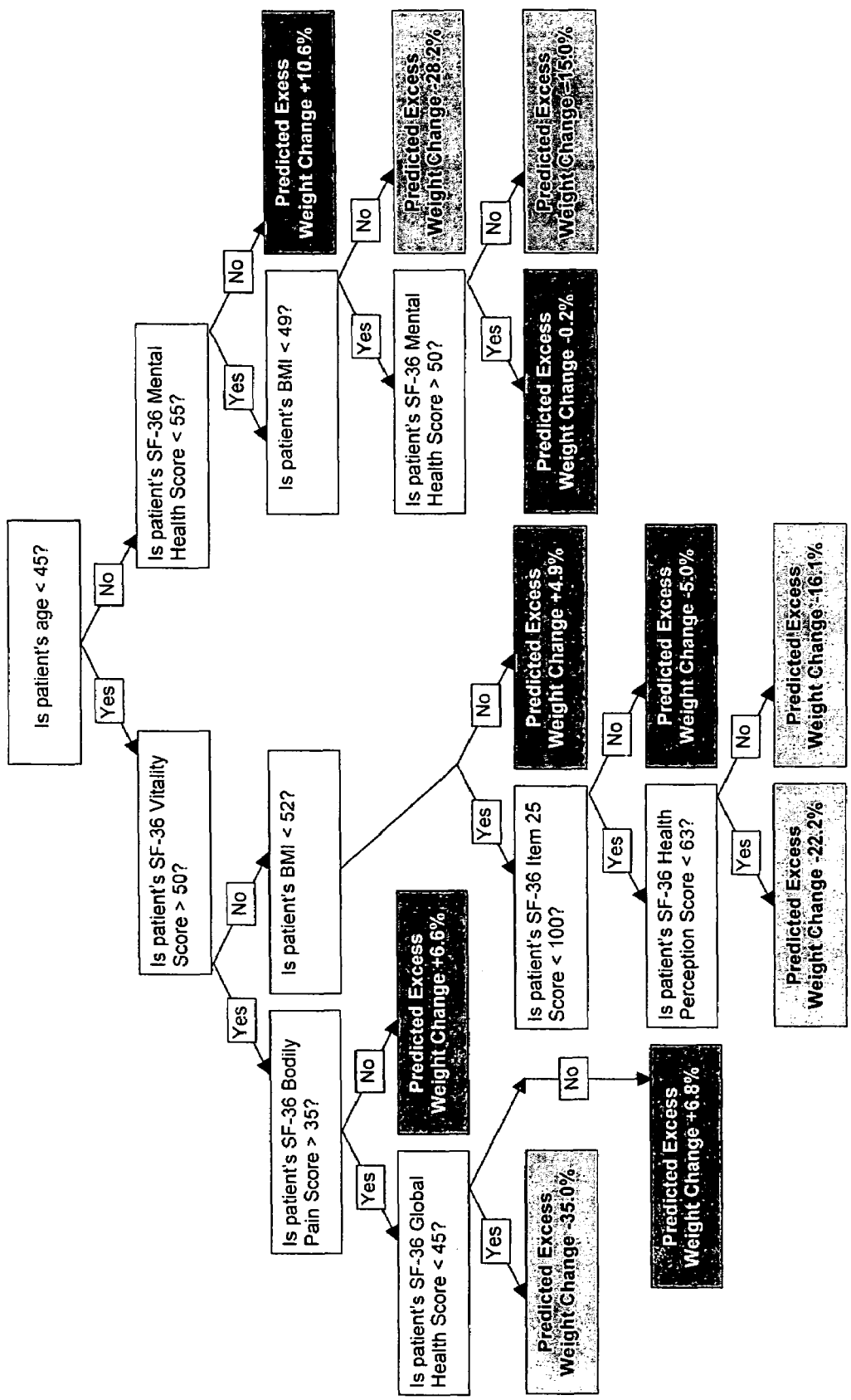
Figure 8. An Example CART Regression Tree for Predicting Weight Change Under GS Treatment

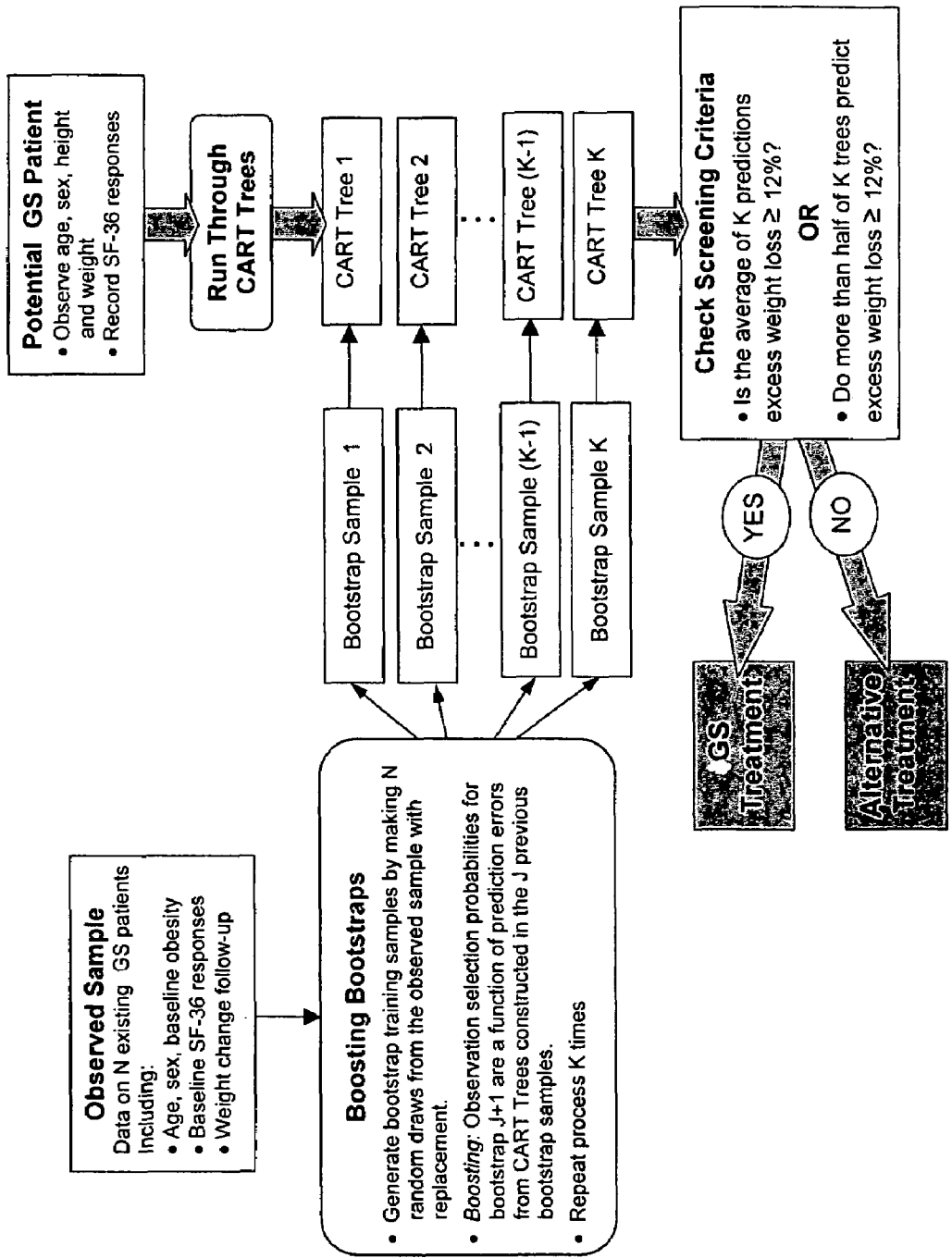
Figure 9. Predicted Weight Loss Screening with Boosted CART Regression Trees

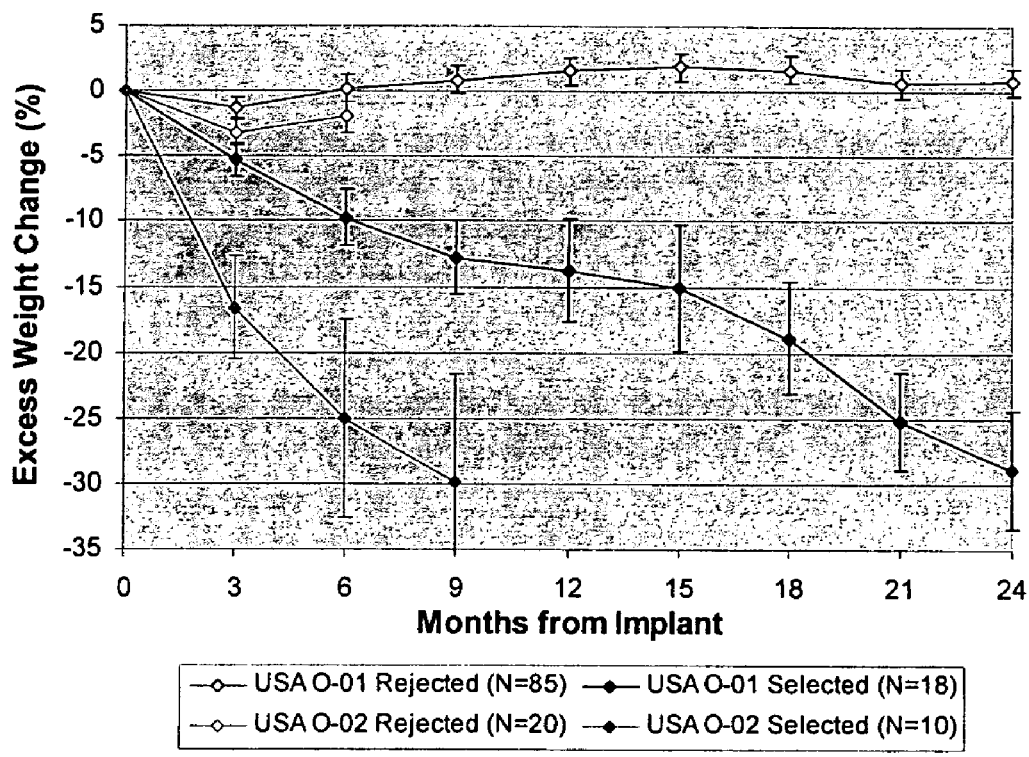
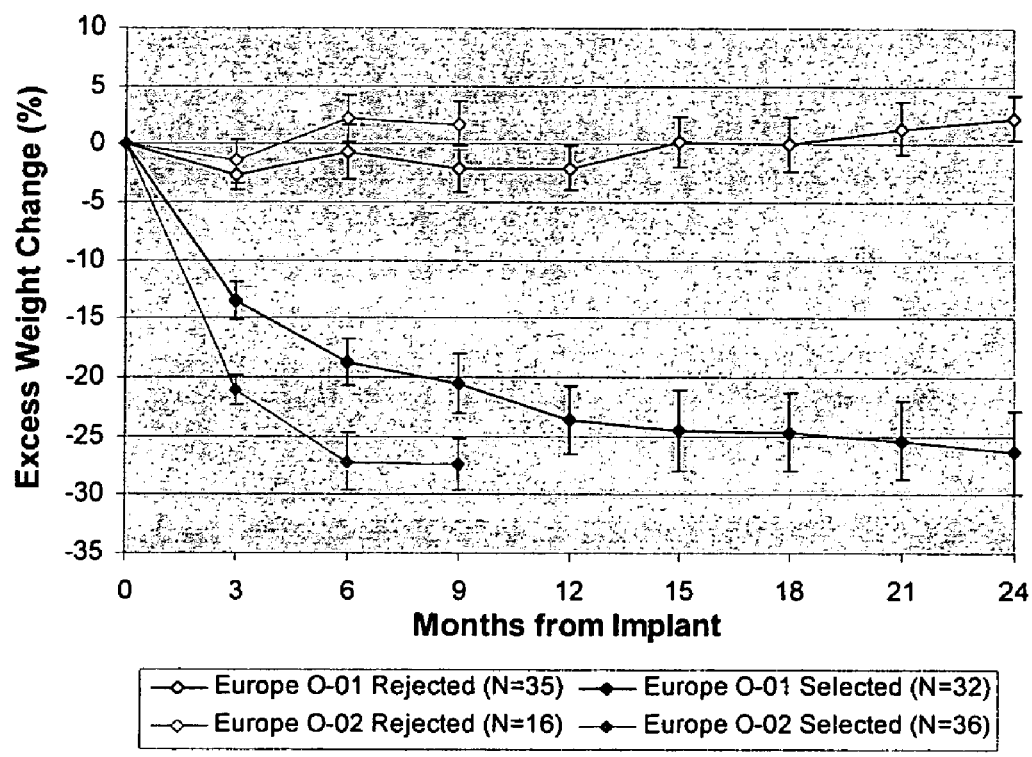

Distribution of Excess Weight Loss by Last Follow-Up in US O-01 Trial Subjects

Distribution of Excess Weight Loss by Last Follow-Up in US O-02 Trial Subjects

Distribution of Excess Weight Loss by Last Follow-Up in Europe O-01 Trial Subjects Distribution of Excess Weight Loss by Last Follow-Up in Europe O-02 Trial Subjects Distribution of Excess Weight Loss by Last Follow-Up in US O-01 Trial Subjects Distribution of Excess Weight Loss by Last Follow-Up in US O-02 Trial Subjects Distribution of Excess Weight Loss by Last Follow-Up in Europe O-01 Trial Subjects Distribution of Excess Weight Loss by Last Follow-Up in Europe O-02 Trial Subjects Probability of Selection for Treatment by the Screening Algorithm:
Association with Patient BMI and Age

**Probability of Selection for Treatment by the Screening Algorithm:
Association with Baseline SF-36 Scores**

Emotional Well Being Score

General Health Perception Score

Physical Health Composite Score

Vitality Score

Weight Loss Maintenance under GS and Sibutramine

Weight Loss Maintenance under GS and Orlistat

Weight Loss Maintenance after a Year of Diet and Counseling Compared to GS

Outcomes in Screened Patients and Patients Selected on Initial Weight Loss

Goodness-of-Fit Plot for Descriptive Logistic Model

METHOD FOR SCREENING AND TREATING PATIENTS AT RISK OF MEDICAL DISORDERS

CROSS-REFERENCE TO RELATED APPLICATIONS

This application claims the benefit of priority under 35 U.S.C. § 119(e) to U.S. Provisional Application Ser. No. 60/508,280, filed Oct. 6, 2003, the entire disclosure and contents of which are incorporated herein by reference for all purposes.

FIELD OF THE INVENTION

This invention relates generally to methods for screening and treating patients at risk of medical disorders.

Obesity is a chronic, lifelong disease of excessive fat storage. It has highly significant associated medical, psychological, social, physical and economic co-morbidities. As presently understood, it is a multifactorial, genetically-related disease involving heredity, biochemical, hormonal, environmental, behavioral, public health and cultural elements. Morbid obesity, also referred to as severe obesity, typically is associated with a body mass index (BMI), i.e., the ratio of weight in kg to the square of the height in meters, of close to, or in excess, of 40 $kg/m^2$. Mortality rates for morbidly obese individuals are more than twice as high as those for otherwise similar normal weight individuals. Comorbidities associated with obesity include, for example, high blood pressure, hypertension, high blood cholesterol, dyslipidemia, Type 2 (non-insulin dependent) diabetes, insulin resistance, glucose intolerance, hyperinsulinemia, coronary heart disease, angina pectoris, congestive heart failure, stroke, gallstones, cholesystitis, cholelithiasis, gastroephageal reflux disease (GERD), gout, osteoarthritis, respiratory problems such as obstructive sleep apnea and sleep apnea complications of pregnancy, cancer (e.g., endometrial, breast, prostate, and colon cancers), poor female reproductive health (e.g., menstrual irregularities, infertility, irregular ovulation), bladder control problems (e.g., stress incontinence), uric acid nephrolithiasis, psychological disorders (e.g., depression, eating disorders, distorted body image, and low self esteem). Morbid obesity is, therefore, an extreme health hazard, if left untreated.

Diet programs and behavioral modification programs have been generally ineffective in providing long-term maintenance of weight loss in morbidly obese patients. There is an extremely high incidence of failure to sustain even a 5 percent long-term weight loss in morbidly obese patients with any form of non-operative treatment. Pharmacological drugs or other orally administered remedies used in efforts to induce weight loss currently have no clinically proven efficacy or may create serious health risks.

Surgical procedures have been developed and used to help control obesity. Bariatric procedures performed in this regard include malabsorptive and restrictive surgical procedures. Both of these bariatric procedures have some immediate and/or delayed risks.

Malabsorptive procedures decrease intestinal absorption by the patient. The most widely used method is the Roux-en-Y Gastric Bypass. In this procedure, the surgeon uses staples to construct a proximal gastric pouch with an outlet that is a limb of the small bowel, thus bypassing most of the stomach and some of the small intestine. Reported complications associated with the Roux-en-Y Gastric Bypass are disruption of the staple line forming the proximal gastric pouch such as the result of cutting and suturing of the gastrointestinal tract; gastrointestinal leakage and ulceration at the site of the anastomosis of the small bowel; long-term, micronutrient deficiencies such as in B12, folate and iron; and "dumping syndrome" (a gastrointestinal distress reaction to sugar intake). Although weight loss results for patients undergoing Roux-en-Y Gastric Bypass vary widely, it is generally reported that weight is greater in the first year after surgery with successive years resulting in a slowing in weight loss and even weight regain.

Restrictive surgical procedures decrease the amount of solid food a patient is able to ingest. Common restrictive surgical techniques are Vertical Banded Gastroplasty (VBG); Silicone Ring Gastroplasty (SRG); and Gastric Banding. In VBG and SRG, reduction in stomach size is achieved by using rows of staples to create a small stomach along the lesser curvature of the stomach. The pouch outlet (stoma) is reinforced with a marlex band or silicon ring, sometimes placed through a hole in the stomach created by a circular stapler. Reported complications associated with VBG and SRG include operative complications such as leakage, sepsis, pneumonia, and deep vein thrombosis; disruption of the staple line over a period of time leading to weight regain; obstruction (stenosis) of the reinforced stoma outlet; and migration and/or erosion of the reinforced band or ring. In Gastric Banding, a small upper pouch and reinforced stoma are created in one step by placing a band or ring around the upper stomach. This procedure avoids the complications associated with staple line leakage and disruption, but may be associated with a higher rate of pouch enlargement and obstruction.

Implantable gastric stimulation systems have been developed as a significantly less invasive surgical approach for treatment of obesity. An example of such a system is the Transcend® IGS® apparatus, developed by Transneuronix, Inc., Mt. Arlington, N.J., U.S.A. The important role played by electrophysiology in controlling gastrointestinal activity has become increasingly apparent in recent years. It recently has been shown, for example, that changes occur in the motility and electromotor conduct of the gastric tract in eating disorders, such as obesity, underweightness, bulimia, and anorexia. Disturbances in electromotor activity in diabetic gastroparesis, reflux in the upper digestive tract, and numerous other gastro-enterological functional pathologies have also been observed. Thus, the possibility has been recognized of correcting digestive tract dysfunction by means of electrostimulation of the intrinsic nervous system of the stomach.

In the treatment of obesity, the implantable gastric stimulation systems electrically stimulate or pace the stomach or intestinal tract with electrodes implanted in the abdomen tissue. One general system includes an implantable pulse generator, an external programmer, and a gastric stimulation lead. The implantable pulse generator delivers electrical pulses to the stimulation lead. The lead conducts the pulses to the smooth muscle of the stomach to stimulate it. The external programmer can non-invasively communicate with the implanted pulse generator and permits modification of the parameters of the electrical stimuli delivered. The implantable pulse generator and lead are implanted in a minimally invasive video-laparoscopic surgical procedure that normally takes approximately one hour or less. Several trocars are often used during the implantation: one for the camera, two for operating ports including a larger diameter operating port used to introduce the lead into the abdominal cavity, and optionally one for liver retraction, with their specific position left to the discretion of the surgeon. The implantable gastric stimulator is placed in a subcutaneous pocket in the abdomen, such as anchored on the fascia.

The electrical stimulator can be programmed to induce in the stomach a motor incoordination in order to slow down or even prevent stomach emptying by slowing gastric transit through the pylorus into the intestine located downstream. This modality, for example, can be used for treatment of obesity, such as related to hyperalimentation. Gastric intestinal stimulators have proven to be relatively safe and straightforward to install and operate in patients.

Gastric stimulation generally has been implemented to help patients lose weight in combination with standard behavior and dietary modifications. It is typically, but not exclusively, indicated for patients with a BMI of greater than 40 or 35–40 with co-morbidity risk factors or conditions. These implantable gastric stimulation systems have been found in long-term studies to be very effective in combating obesity in some patients, but not all patients. The patients that have responded well to gastric stimulation treatment in terms of long-term weight loss have achieved more normal cycles of hunger and satiation. The implanted patients who demonstrate at least modest short-term eating restraint by losing five pounds or more in the initial months of treatment go on to lose an average of 20 percent of excess body weight by their last available follow-up. Moreover, long-term weight loss maintenance in these patients is better than expected under any non-invasive treatment, and rivals that observed in competing surgical procedures that have substantially higher risks of complication-related mortality and morbidity. Still, some implanted patients fail to attain clinically significant weight loss under implantable gastric stimulation therapy. While many of these non-responding patients report an increased sense of satiety and diminished hunger after implantable gastric stimulation activation, their eating is evidently unresponsive to this change in appetite cues. If these non-responders could be reliably identified and excluded prior to implantation, expected weight loss and the ratio of risks to benefits for patients treated with implantable gastric stimulation would greatly improve.

Consequently, a medical understanding has been lacking on which potential patients are more likely to respond successfully to gastric simulation treatment as a treatment for obesity. In particular, there has been no medical understanding in regard to predicting how individual patients at risk of eating disorders may respond to gastric stimulation treatment. A higher degree of confidence is needed in advance that implantable gastric stimulation therapy will work for a given patient.

The development of predictive models to facilitate medical decision-making and improve care recently has received increasing interest. Enormous quantities of data are accumulated in clinical databases of information about patients and their medical histories and conditions. Ideally, evaluation of the stored clinical data could lead to a better understanding of possible trends and patterns hidden within the data that could be used to improve care. Unfortunately, few methodologies have been developed to date that will reliably evaluate and analyze clinical data in particular after it has been captured and stored.

Data mining, also sometimes referred to as Knowledge Discovery in Databases (KDD), searches for relationships and patterns that may exist in large databases but are "hidden" among the enormous amounts of data. A typical data mining process generally involves transferring data originally collected in production systems into a data warehouse, cleaning or scrubbing the data to remove errors and checking for consistency of formats, and then searching the data using statistical queries, neural networks, or other machine learning methods. Most prior applications of data mining have focused on identifying data patterns to solve business related problems. The application of conventional data mining techniques to health care scenarios is much more in its infancy, and it is more problematic with reports of isolated successes.

In general, a wide variety of different types of data mining tools have been introduced in theory or practice that are premised on widely different platforms, algorithms, data input and model output schemes, and so forth. However, among other limitations, data mining tools alone can not substitute for statistical and domain expertise and special knowledge. Medical decision-making applications, in particular, can involve a vast number of potential variables drawn from, for example, all of the physical, psychological, economical, demographical, historical, and social domains of information. For any particular medical decision-making scenario presented, the potential variables and possible techniques for evaluating them may be virtually unlimited. In addition, the development of prediction models for medical intervention strategies and decisions based on the data inputs are prone to overfitting and generalization errors. For example, predictive models generated in health care applications often perform well on the database samples, but fail or perform poorly when applied to new samples of the same population. Advanced Heuristics markets a product known as Cadenza® for providing evidence-based cardiovascular management in which the probability of coronary disease in a patient is diagnosed by application of Bayes' theorem, and also providing probabilistic analysis at each stage of the testing continuum and predicting effectiveness of treatment modalities.

There is a need for a method for predicting the suitability of implantable gastric stimulation treatment for patients with weight or gastrointestinal problems using a highly reliable and accurate predictive model that can be easily administered.

SUMMARY OF THE INVENTION

A method generally is provided for screening patients to predict which patients at risk of a medical disorder will be responders, and conversely, which patients will not, to achieve a favorable outcome from a particular medical treatment or therapy proposed for treating that disorder. In one embodiment, a method is provided for predicting weight loss outcomes of a therapy for patients at risk of morbid obesity, gastrointestinal disorders, or gastroesophageal disorders. The method predicts which at risk patients will be responders, and conversely, which patients will not, to achieve a favorable outcome from a given type of obesity treatment or therapy.

In one more particular embodiment of this invention, there is a method for predicting the weight loss outcome of electrical stimulation of neuromuscular tissue in a patient for treating an eating, gastrointestinal, or gastroesophageal disorder, comprising the steps of a) obtaining items of information from a patient at risk of one of an eating, gastrointestinal, and gastroesophageal disorder, each item of information relating to a preselected patient variable; b) predicting a weight loss outcome for the patient from the obtained information for the patient using an aggregated weight loss predictor developed from i) similar types of information and corresponding weight loss information obtained from an actual population of patients who previously received electrical stimulation treatment, or ii) information generated from a simulated population of patients by resampling the actual population information to produce pseudo-replicates. In one embodiment, the electrical stimulation therapy is implantable gastric stimulation therapy.

In one embodiment, the predicting step of the method comprises comparing the weight loss variable data to similar data gathered from an actual or simulated patient population for which results to an electrical stimulation treatment have been precollected or precalculated, respectively, effective to permit a classification of the patient in terms of a probable outcome to the electrical stimulation treatment. In a further embodiment, a decision is rendered as to whether or not to treat the patient's disorder with electrical stimulation based on the classification of the patient. In one embodiment, patients can self-administer a simple questionnaire to provide data inputs processed by the predictive tool to predict whether a given patient is a favorable candidate for the implantable gastric stimulation treatment. In one particular embodiment, the items of information include i) answers by the patient to questions asked in a psychometric instrument, such as, e.g., a RAND Short Form 36 (SF-36) health survey (version 1.0), a Three-Factor Eating Questionnaire, a Weight Loss of Control (WLOC) questionnaire, or Beck Depression Inventory, and so forth, ii) anthropometric data, such as weight, height, age, sex, and body mass index (BMI) information, and iii) biomarker information, which may include, e.g., hormone information, peptide information (e.g., ghrelin peptide information), genomics information, and body scan information (e.g., a positron emission tomography brain scan), or any combination thereof.

In one particular embodiment, the development of the predictive model for weight loss outcomes of an obesity treatment includes processing the items of patient information using an aggregated classification and regression tree model formed using a statistical ensemble or committee method such as a bootstrap, bagging, or arcing algorithm. In a further embodiment, the aggregated classification and regression tree model is trained by preprocessing i) historical data comprising actual patient information of patients who previously received electrical stimulation treatment, and ii) the corresponding weight loss outcomes those patients to learn how to predict weight loss outcomes. In one particular embodiment, the preprocessing comprises reducing the quantity of the historical patient information and corresponding patient weight loss outcomes; reducing the number of variables contained in the historical patient information and corresponding patient weight loss outcomes using classification and regression trees; transforming the values of the historical patient information and corresponding patient weight loss outcomes; applying a boosting algorithm to the extracted features; and generating the classification and regression tree model to predict a weight loss outcome from the boosted extracted features. In one further embodiment, the model is cross-validated by repeated training of the model in a randomly chosen 90 percent training samples followed by prediction in the remaining 10 percent hold-out test set to yield estimates of the screening-related improvement in implantable gastric stimulation weight loss outcomes.

In another embodiment, the prediction of the weight loss outcome comprises processing the items of information using an aggregated classification and regression tree model formed using a bootstrap algorithm including a combination of many distinct trees, each model estimated in a sequence of bootstrap samples drawn from the original sample, and wherein a screening decision for a patient is then based on a combination of average predicted weight loss across bootstrap trees and a majority vote criterion comprising whether a majority of the bootstrap trees predict weight loss above a predetermined threshold level.

The method according to an embodiment of this invention supports an intervention strategy for patients having weight or gastrointestinal problems that will cut health costs. The method of this invention is particularly useful for treatment of individuals at risk of obesity. This invention enables patients and health care-providers to more efficiently use their time, efforts and resources by enabling an early selection of an appropriate treatment modality for a given patient. The screening method employs a predictive model that provides an accurate prediction of the weight loss outcomes for patients at risk of morbid obesity or gastrointestinal disorders who are considering undergoing gastric stimulation treatment. Patients predicted by the tool to have an unacceptably low probability for an obesity treatment to work well on them can be redirected to other treatment options without delay, which also saves health costs and time.

The invention encompasses, but is not limited to, implantable pulse generator therapy for treating obesity, and also extends to other obesity therapies, both surgical, such as gastric by pass, vertical banded gastroplasty, or banding with devices such as the LapBand marketed by Innamed or Swedish Band marketed by Johnson & Johnson, and non-surgical, such as behavioral modification therapy, or low calorie or very low calorie (liquid fasting) dieting. Further, while the optimal implantable pulse generator therapy may be the pacing of the stomach in many situations, the placement of the implantable pulse in embodiments of the present invention extends to generator therapy for obesity including, but not limited to, the stimulation of the stomach, vagus nerve, intestines, brain, and spinal cord.

BRIEF DESCRIPTION OF THE DRAWINGS

The present invention is illustrated by way of example and not limitation in the accompanying figures, and in which:

FIGS. 2–7 show details of a SF-36 Health Survey used as a source of patient data according to an embodiment of the present invention;

FIG. 8 is a CART regression tree for predicting weight change under implantable gastric stimulation treatment according to an embodiment of the present invention;

FIG. 9 is a flow chart illustrating the data analysis used for predicted weight loss screening with boosted CART regression trees in accordance with a more particular embodiment of the present invention;

FIGS. 10–11 are plots of excess weight change (%) as a function of months from implant for the trial patients for the U.S. and European trials, respectively, indicated in Table 1 as between the trial subjects classified as either "rejected" or "selected" by the model for implantable gastric stimulation treatment using a predictive model developed according to an embodiment of this invention;

DETAILED DESCRIPTION OF THE INVENTION

The present invention generally relates to a method for screening patients to predict which patients will be responders to a proposed medical treatment or therapy for a given disorder.

In one aspect, the present invention relates to a method for screening patients who are candidates for an obesity treatment, and other treatments for other motor disorders of the stomach or other tissues. A screening algorithm is included in the method that reliably and significantly improves the predictability of obesity treatment weight loss outcomes in candidate patients based on prognostic factors and data known for and/or elicited from a patient prior to treatment, preferably with minimal cost and patient inconvenience.

Figure 1:
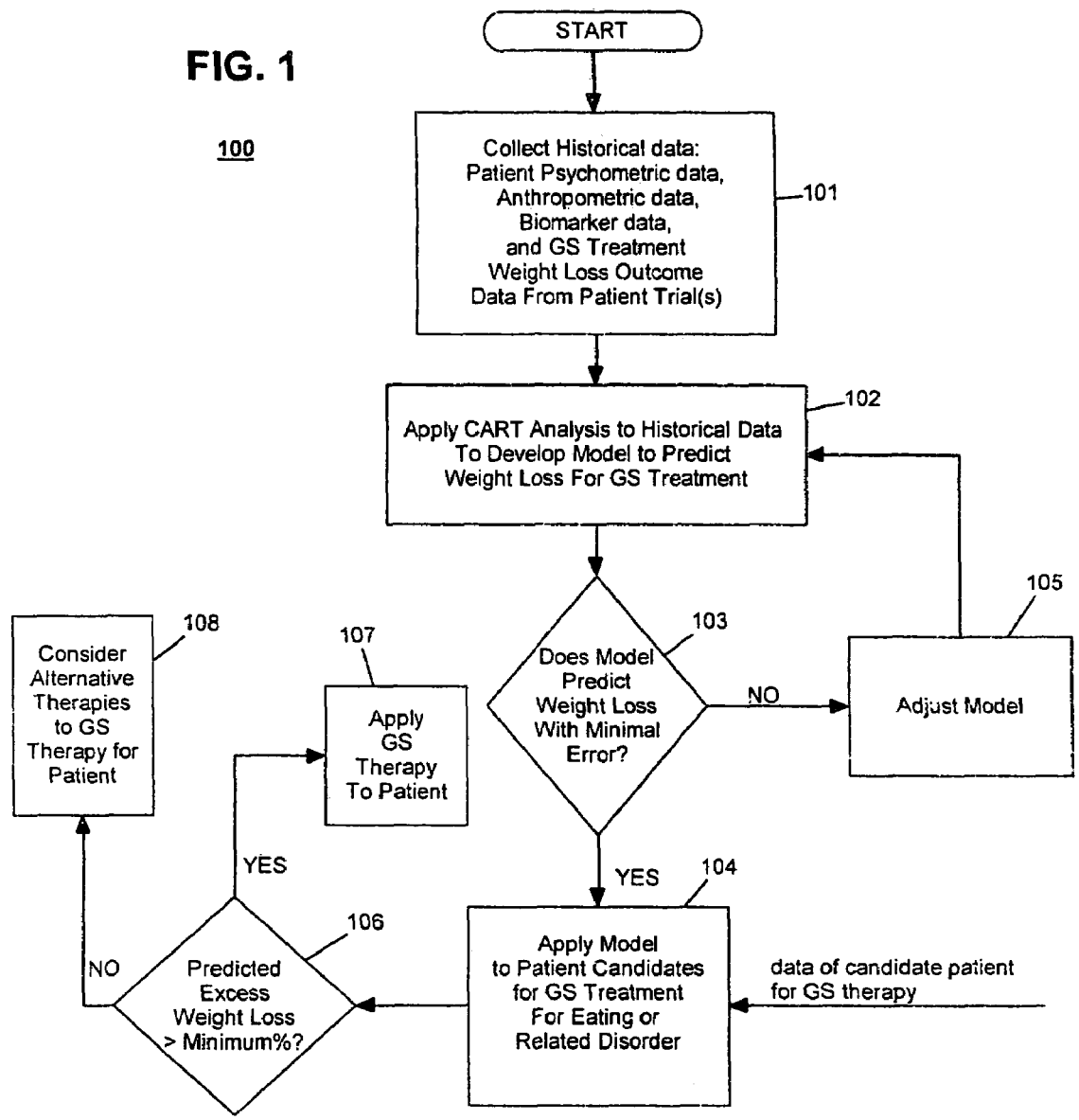
FIG. 1 is a flow chart setting forth the steps used to train, test, and apply a predictive model for implantable gastric stimulation treatment in a patient at risk of eating, gastrointestinal, and gastroesophageal disorders according to an embodiment of this invention.

Referring to FIG. 1, a general overview of one embodiment of this invention is illustrated for providing a reliable predictive model of weight loss outcomes of patients at risk of obesity and so forth to implantable gastric stimulation treatment for such disorders. In this non-limiting illustration, a device having a microprocessor, such as a computer, that contains CART model software is trained and tested with historical patient data gleaned from a psychometric instrument, anthropometric data, the associated weight loss outcomes for those patients upon undergoing implantable gastric stimulation treatment for obesity, and biomarker data (which is optional in this illustration). The terminology "implantable gastric stimulation" is occasionally abbreviated herein and in the accompanying figures as "GS." At 101, the patient's historical data is collected. Psychometric data may be collected via a psychometric instrument, such as, e.g., a RAND Short Form 36 (SF-36) health survey (version 1.0); a Three-Factor Eating Questionnaire (e.g., Stunkard, A. et al., The Three-Factor Eating Questionnaire to measure dietary restraint, disinhibition and hunger, *J. Psychosom. Res.*, 29:71–83, 1985), a Weight Loss of Control (WLOC) questionnaire (e.g., Saltzer, E., The weight locus of control (WLOC) scale: A specific measure for obesity research, *Personality Assessment*, 46(6), 620–628, 1982), or Beck Depression Inventory (Beck, A., et al., Beck Depression Inventory-II (BDI-II), The Psychological Corporation, San Antonio, Tex., USA, 1996), and so forth. As an alternative to using such self-report type questionnaires, the psychometric data also may be collected via patient interview at least in part, e.g., using The Yale-Brown-Cornell Eating Disorder Scale (e.g., see Sunday, S., et al., Yale-Brown-Cornell Eating Disorder Scale: a new scale to assess eating disorder symptomatology, *Int J Eat Disord*, 1995 Nov; 18(3):237–45). The anthropometric data may include, e.g., weight, height, age, sex, and body mass index (BMI)

information. The biomarker information may include, e.g., hormone information, peptide information (e.g., ghrelin peptide information), genomics information, and body scan information (e.g., a positron emission tomography brain scan), or any combination thereof. As will be understood, a patient's body mass index (BMI) value can be computed from the patient's height and weight data, and thus it need not be provided as information per se by the patient. Thereafter, at 102, a decision-tree analysis is applied to the historical data to develop a predictive model for outcomes of the implantable gastric stimulation therapy. Once the predictive model is developed from the training set of data, a testing set of data is developed, such as by a cross-validation technique as described in more detail below, is used to test how well the training model predicts weight loss outcomes at 103. The testing is measured, for example, by using misclassification rates. If the trained model does predict the weight loss with minimal error (e.g., <20% misclassification) at 103, then the model is ready to be used at 104 to predict weight loss outcomes for implantable gastric stimulation therapy candidates. However, if the trained model is unable to predict the weight loss outcome with minimal error at 103, then the model is adjusted at 105 and steps 102 and 103 are repeated until the misclassification rate error becomes small enough. For example, the model may be adjusted by using different feature extraction algorithms, described in more detail below. It should be noted that adjusting the predictive model in this fashion may require obtaining additional test set data in order to obtain valid estimates of the likely generalization error that will occur when the predictor is used to screen new patients from the same population. At 106, the data supplied by the candidates for implantable gastric stimulation therapy is processed by the predictive model to determine the associated predicted weight loss via implantable gastric stimulation therapy for a given candidate. If the predicted weight loss meets an arbitrary minimum percentage correlated with a reasonably significant and meaningful outcome to implantable gastric stimulation therapy by health professionals in this field, then the candidate is "approved" for the implantable gastric stimulation therapy at 107. On the other hand, a candidate who does not meet the criteria at 106, then the patient can consult with his or her health care practitioner at 108 about alternative therapies at an early juncture while foregoing the time and cost otherwise may have been devoted to implantable gastric stimulation therapy with little prospect of a favorable outcome. It will be appreciated that other algorithms might be used in lieu of a decision tree-based analysis, such as a neural network analysis.

In more detail, in one embodiment of this invention there is a method using data drawn from a large of pool patients receiving implantable gastric stimulation treatment, e.g., more than 250 implantable gastric stimulation treatment trial patients, to initially estimate a regression model for predicting weight loss at the last available follow-up based only on patient information collected before treatment. The predictive validity of this model is then tested using a form of cross-validation. This entails repeatedly estimating the model in subsets of the sample data, and then using these estimates to predict weight loss in independent test sets comprised of data excluded from the estimation. If the average test set prediction error is sufficiently small, the model is designed to provide usefully accurate predictions of weight loss outcomes in new samples of implantable gastric stimulation treatment candidates drawn from the same severely obese population.

Here "usefully accurate" means that retention and rejection of future patients based on model predictions will be characterized by low rates of false positives and false negatives. In other words, only a small percentage of retained implantable gastric stimulation patients will fail in attaining significant weight loss, and it can be expected that a similarly small percentage of rejected patients would have done well under implantable gastric stimulation. The results of the present invention represent a significant advance and breakthrough in the treatment of patients at risk of obesity and related disorders of the stomach. Namely, a highly useful predictive model for implantable gastric stimulation treatments has now been developed based on particular baseline information collected on an available sample of implantable gastric stimulation trial subjects that had not previously been recognized as having as association with weight loss outcomes. Indeed, if the baseline data were not analyzed according to a method of the present invention, estimates of test set error for a model offering good within-sample prediction might indicate that it is likely to predict poorly in new patients.

As it turns out, weight loss outcomes in the implantable gastric stimulation trial data appear highly predictable using a limited set of predictors observed at study entry, including age, sex, measures of obesity, and the individual item and summary scale scores from the RAND Medical Outcomes Study SF-36 Health Survey or other suitable psychometric instrument. More importantly, test set performance of the prediction model suggests that using it to screen new subjects is likely to yield mean implantable gastric stimulation weight loss approximately three times that obtained without screening. Additionally, qualitative support for the face validity of the prediction model can be garnered from the fact that the nature and direction of the associations it uses to predict weight loss are consistent with the existing literature on obesity treatment and weight-related behaviors.

In one embodiment, the methods applied to arrive at a predictive screening model come from the field of data mining. Data mining techniques are well suited to the implantable gastric stimulation screening problem in several respects. The primary focus of the field is prediction, with particular emphasis on producing models that will generalize to new samples. Toward this end, data mining tools include methods for limiting and estimating the amount of generalization error that is likely to occur when the analysis moves from the training sample used to develop a predictor to independent samples from the same population. Further, data mining methods are specifically designed for analysis of convenience datasets, such as the implantable gastric stimulation trial data in the present instance, which were originally collected for other purposes and contain a large number of potential predictors. Some of the available variables may have predictive value for the target variable of interest, while many others are likely irrelevant. Given the happenstance nature of the data, there is typically a dearth of prior information to guide predictor selection, and thus little alternative to the data driven, (as opposed to hypothesis driven), model building processes of data mining.

In one embodiment, regression tree methods are employed for analysis of the implantable gastric stimulation trial data, which build a decision tree for sorting subjects into relatively homogenous groups with similar values of a continuous target variable, such as weight loss. Regression tree algorithms date at least to the Automatic Interaction Detection (AID) algorithm proposed by Morgan and Sonquist four decades ago. Morgan, J. and J. Sonquist, *Problems in the Analysis of survey Data and a Proposal*, J. Amer.

Statistical Assoc., 1963, 58:415–434. Since then a range of competing tree-building algorithms have been developed. In one embodiment, for the implantable gastric stimulation screening problem, Breiman, Friedman, Olshen, and Stones' CART algorithm was adopted. Breiman, L., et al., Classification and Regression Trees, 1984, New York: Chapman Hall.

The acronym "CART" stands for Classification And Regression Trees. Many other tree-based algorithms can be grouped under the same heading. CART is a flexible, non-parametric algorithm for building either classification or regression trees that has proven to be a useful predictor in many different contexts. Alternatively, Quinlan's C4.5 algorithm could be adapted for analysis of the implantable gastric stimulation trial data (see, e.g., Quinlan, J. R., *Programs for Machine Learning*, The Morgan Kaufman Series in Machine Learning, Morgan Kaufman Publ., San Mateo, Calif. (1993)).

Decision-tree based methods are only a modest subset of the data mining tools available for predictive modeling. Leading alternatives include k-Nearest Neighbor methods (see, e.g., Duda, R., et al., *Pattern Classification and Scene Analysis*, New York, John Wiley & Sons, 1973), and Neural Network methods (see, e.g., Rumelhart, D., et al., "Learning internal representations by error propagation," in *Parallel Distributed Processing Exploration of the Microstructure of Cognition*, Cambridge, Mass.: MIT Press 1986). Both of these have been found to offer prediction that is superior tree-based methods in many instances. Nonetheless, CART regression trees have two critical advantages. First, CART is better suited to modeling of scenarios characterized by a large number of candidate predictors and limited information to guide predictor selection. Unlike Nearest Neighbor and Neural Network methods, CART is insensitive to the inclusion of irrelevant variables in the input predictor set, robust to the presence of outlier values in these inputs, and unaffected by monotone transformations of predictors. The second major advantage of tree-based methods like CART lies in interpretability. While it is unlikely to appear so to those unfamiliar with data mining algorithms, tree-based methods are far less of a "black box" than the alternatives that provide superior prediction. The algorithm used to construct CART regression trees is relatively simple to describe in plain English, with minimal reference to mathematics and statistics. Interpretability is further aided by the fact that the predictive model is expressed in the form of a decision tree, a device commonly used in both managerial and medical decision making.

While these features make tree-based methods like CART an attractive data mining technique, they come at the cost of predictive accuracy. Regression trees are often unstable, varying dramatically in response to small changes in the estimation data. They provide excellent prediction within the training sample used in building the decision tree, but their instability can result in unfavorably large generalization error when the estimated tree is applied to independent samples. A recent innovation in data mining known as "boosting" has been shown to dramatically reduce the generalization error associated with tree-based methods. Simulation studies by Breiman and others have found that using boosting in conjunction with tree-based predictors like CART yields mean test set prediction error that approaches the minimum possible (i.e., the level attainable using the true conditional expectation of the target given the predictors).

In one embodiment, the analysis of the implantable gastric stimulation data employs the variant of boosting developed by Breiman referred to as "adaptive resampling and combining," or "arcing". E.g., See Breiman, L., Arcing Classifiers, Annals of Statistics, 1998. 26:801–49. Boosting reduces the generalization error associated with CART trees by combining predictions from many trees, typically 250 or more, each estimated in a different perturbed version of the observed training sample. The perturbed data sets are a sequence of bootstrap training samples, generated by random draws with replacement from the observed sample. The sampling probabilities used to draw the $j^{th}$ bootstrap training sample under boosting are a function of prediction errors in the previous (j−1) bootstraps, and evolve adaptively to give progressively greater weight to difficult to predict observations. Prediction for new subjects is then based on combining predictions from the estimated sequence of boosted trees by averaging or majority voting. In this embodiment, a combination of both is used. Prospective implantable gastric stimulation patients are retained for treatment if either the average of their predicted weight loss exceeds 12 percent of their baseline excess body weight, or if the majority of 250 boosted CART trees predict greater than 12 percent excess weight loss.

It will be appreciated that the processing of the patient information data obtained generally may be performed using an aggregated classification and regression tree model formed using a statistical ensemble or committee method, such as a bootstrap, bagging, or arcing algorithm.

The implantable gastric stimulation trial data used in one embodiment to develop and test the predictive screening model is described in more detail below. A brief overview of regression trees will also be provided below, and then details the process of building and combining boosted CART trees. The effects on weight loss outcomes and patient retention obtained by applying the predictive screening model to the implantable gastric stimulation trial data are also described below. In data mining terminology, the estimated benefits of predictive screening presented in the last-mentioned section are called "resubstitution estimates," since they are obtained by applying the predictive model back to the same sample used to train it. Resubstitution estimates are by definition free of generalization error and provide an optimistic representation of how a predictor will perform in new samples. The validation experiment described in another section below provides evidence that generalization error is likely to have only a small effect on the ability of the boosted CART predictor to accurately screen new implantable gastric stimulation patients. Repeated training of the model in randomly chosen 90 percent training samples followed by prediction in the corresponding 10 percent hold-out test set yields estimates of the screening-related improvement in implantable gastric stimulation weight loss outcomes that are only slightly less than the resubstitution estimates. The specific associations that drive patient selection under the predictive screening model of embodiments of this invention are also discussed herein.

EXPERIMENTAL

EXAMPLE 1

Development/Validation of Predictive Model

A. Data Description

In one embodiment, the CART predictive screening model is estimated and validated using baseline and weight change follow-up data on 252 of 279 implantable gastric stimulation patients implanted in the course of four treatment trials conducted in Europe and the United States.

Apparatus for stimulating neuromuscular tissue of the gastrointestinal tract and methods for installing the apparatus to the neuromuscular tissue and therapeutic techniques for operating the apparatus as applied to these patients are indicated in Table 1 below. Further details on how to perform the implantable gastric stimulation treatment are described in U.S. Pat. No. 5,542,776 B1 to P. Gordon and D. Jenkins, which descriptions are incorporated herein by reference.

Table 1 below provides brief descriptions of these trials and their participants. The study samples are predominantly middle aged and female. Primary inclusion criteria required that trial participants be severely obese, having a body mass index (BMI) of 40 or higher, or having a BMI of 35 or higher with co-morbid conditions. The CART analysis includes 90 percent of all patients implanted in the four studies. 27 European patients were excluded for whom a completed baseline SF-36 Health Survey was lacking. As discussed further below, the SF-36 individual item scores and summary scales account for most of the predictors input into the CART algorithm.

The target variable that is the focus of the predictive modeling of an embodiment of this invention is change in weight by the last available follow-up as a percentage of excess body weight at implant. For purposes of this application, "excess body weight" at implant is calculated using ideal body weight estimates from the 1983 Metropolitan Life tables. The ideal body weight for each patient is taken to be the midpoint of the Metropolitan Life minimum-mortality weight range for a medium frame person of the same height and sex. Percentage change in excess body weight calculated in this fashion has become the dominant outcome measure reported in the bariatric literature. Unless indicated otherwise, the terminology "excess weight" as used herein also refers to excess body weight.

As described in Table 1 there is a large difference in the mean months to last follow-up across implantable gastric stimulation trials. The two newer trials have mean follow-up of nine months or less while implanted patients from the earlier generation of trials have been followed an average of more than 18 months. An alternative to the use of weight loss at the last available follow-up would be to use a single weight loss endpoint, such as six months from implant. This was not done for four primary reasons. First, the choice of a common endpoint is complicated by the fact that some patients from the earlier trials were randomized into implantable gastric stimulation On (i.e., "GS On") and implantable gastric stimulation Off (i.e., "GS Off") groups during the initial months of study. Second, the use of the last available follow-up maximizes the size of the sample available for developing the predictive screening model. Third, the health benefits of weight loss are sustained only through its long-term maintenance, meaning that the longest available follow-up is also the most clinically significant. Finally, short and long-term weight changes are highly correlated in implantable gastric stimulation patients implanted for more than a year. Because of this, screening based on predictions of six or 12-month weight loss would result in a selection of patients very similar to that obtained with predictions of weight loss at the last available follow-up.

Predictors of excess weight loss entered into the CART algorithm include gender, age at implant, and measures of baseline obesity, (body weight, excess body weight, excess body weight as a percentage of ideal weight, and BMI). These variables are obvious candidates for inclusion among the input predictors. Most of the existing studies attempting to predict obesity treatment outcomes include age, sex and baseline obesity in their predictive models, and a number of these studies report that these variables are significantly correlated with weight loss. The only other predictors entered into the CART algorithm are 52 variables created from subject responses to the SF-36 Health Survey (Version 1) completed prior to implant. The SF-36 Survey Form is illustrated in FIGS. 2–7.

The SF-36 is a widely used instrument for measuring health states. The "SF" stands for "Short Form" and reflects the fact that the survey's 36 item battery is drawn from an earlier, 149 item "Long Form" version developed for the RAND Health Insurance Experiment and Medical Outcomes Study. Studies of the validity and reliability of the SF-36 are numerous and generally supportive of its usefulness in measuring both physical and mental health. The instrument has also been translated into nearly all European languages as part of the International Quality of Life Assessment (IQOLA) Project. The IQOLA Project is funded primarily by major pharmaceutical companies and includes investigators from more than 50 countries. All of the Project's translations are subjected to formal psychometric testing prior to publication to assess translation quality and validity. Translations of the SF-36 into French, Italian, Spanish, German, and Swedish were used at the European implantable gastric stimulation trial sites. While the SF-36 was used within this specific embodiment, one skilled in the art could appreciate that other validated lifestyle, quality of life, mental health or mental well being questionnaire forms could be substituted with perhaps similar results.

TABLE 1

Implantable Gastric Stimulation (GS) Treatment Trial Data Summary

| Trial ID, Start Date | GS Implants | Included In CART Analysis | Patient Characteristics | Trial Characteristics |
|---|---|---|---|---|
| US O-01, Feb. 10, 2000 | 103 | 103 (100%) | Mean Age: 40<br>Females: 84%<br>Mean BMI: 46 | Treatment with single-lead, Transcend® IGS® device without diet or behavioral intervention at 10 US sites. Subjects randomized at one month post-implant into either GS On or GS Off conditions for 6 months. Mean months from implant to last follow-up: 18.6. |
| US O-02, Feb. 19, 2002 | 30 | 30 (100%) | Mean Age: 39<br>Females: 87%<br>Mean BMI: 43 | Single arm trial of dual-lead Transcend® IGS® device with dietary advice at 2 US sites. Mean months from implant to last follow-up: 9.0. |

TABLE 1-continued

Implantable Gastric Stimulation (GS) Treatment Trial Data Summary

| Trial ID, Start Date | GS Implants | Included In CART Analysis | Patient Characteristics | Trial Characteristics |
|---|---|---|---|---|
| Europe O-01, Jan. 19, 2000 | 81 | 67 (82%) | Mean Age: 40 Females: 84% Mean BMI: 46 | Treatment with single-lead Transcend ® IGS ® device without diet or behavioral intervention at sites in 8 European countries. A subset of 20 patients at two sites were randomized at one month post-implant into either GS On or GS Off conditions for 6 months. Mean months from implant to last follow-up: 22.4. |
| Europe O-02, Jan. 23, 2002 | 68 | 52 (76%) | Mean Age: 41 Females: 71% Mean BMI: 41 | Single arm trial of single-lead Transcend ® IGS ® device with monthly dietary counseling at sites in 5 European countries. Mean months from implant to last follow-up: 7.6 |
| All Combined | 279 | 252 (90%) | Mean Age: 40 Females: 79% Mean BMI: 44 | Mean months from implant to last available follow-up: 16.2 |

The SF-36 is designed to be a multidimensional measure of health. Individual item responses are translated onto a scale from 0 (worst) to 100 (best). Each item score then contributes to one of eight multi-item scales measuring distinct dimensions of health. The health dimensions covered by the eight SF-36 scales are physical functioning, social functioning, physical role limitations, emotional role limitations, emotional well-being, bodily pain, and general health perceptions. Additionally, global scales have been developed for physical, mental and general health. For all SF-36 scoring and scale calculation, the SAS macro published by Hays and colleagues was relied upon. Hays, R., et al., A Microcomputer Program that generates SAS Code for Scoring the SF-36 Health Survey, in SAS Users Group Int'l SUG122 Proc., 1997, SAS Inst.: Cary, N. C., pp. 1128–1132. The SF-36 predictor set entered into the CART model includes the 0 to 100 scale scores for the 36 individual items and the eight multi-item health dimension scales. Additionally, two versions of mental and physical health summary scores are included in this embodiment; one set calculated using the RAND method advocated by Hays et al., RAND 36-Item Health Survey 1.0, 1992, Santa Monica, Calif.: RAND Health Sciences program, and a second set calculated using the New England Medical Center (NEMC) method of Ware, Kosinski and Keller, SF-36 Physical and Mental Health Summary scales: A User's Manual, 1997, Boston, Mass.: The Health Institute, New England Medical Center. The NEMC group's general health summary score was also included, and their specific variant of the scores for SF-36 items 1, 21 and 22.

The SF-36 based variables were used in the predictive screening model for at least two main reasons. First, at least one recent investigation of bariatric surgery outcomes has found pre-surgery SF-36 responses to be predictive of weight loss. Second, there is a body of literature suggesting that motivation to attempt and succeed in intentional weight loss depends critically on an obese individual's recognition of the negative health consequences of his or her obesity. This led to the working hypothesis that implantable gastric stimulation patients sufficiently motivated to attempt to restrain their eating, and thereby to benefit from the appetite reducing effects of the device, would likely have SF-36 responses reflecting awareness of the physical and psychological consequences of severe obesity.

B. Application of Regression Trees, CART and Boosting Techniques

Regression trees, like commonly used linear or logistic regression models, provide a method of predicting some target or dependent variable from a set of predictor variables. In a regression tree, however, prediction is not based on a single equation that is fit to the entire sample, but on a sequence of local regressions, fit to subsets of the sample. The result is not a set of estimated regression coefficients, but a set of logical rules that divide the sample into subsets, referred to as "terminal nodes" or "leaves", that are relatively homogenous in the observed values of the target variable. To predict the value of the target variable for a new subject, the values observed for the subject's predictor variables are taken and the tree rules are followed, running through the branches until arrival at a terminal node or leaf. The mean (or some other measure of central tendency) of the target variable for the estimation sample subjects who were similarly sorted into this final node is the predicted value of the target variable for the new subject.

Closely related to regression trees, and nearly identical in their final form, are classification trees. These are used when the target variable being predicted is categorical, rather than continuous. The terminal nodes or leaves of a classification tree each correspond to a particular category of the target variable. Running new subjects through the tree rules sorts them into predicted classes or categories of the target variable. In the implantable gastric stimulation patient screening project of this inventive embodiment, the outcome of primary interest is a continuous variable (percentage excess weight loss), hence a regression tree is used. An alternative would be to partition this continuous outcome variable into categories (e.g., gained weight, lost<12 percent of excess weight, lost≧12 percent of excess weight) and estimate a classification tree. The key drawback of such artificial treatment of a continuous variable as categorical is information loss. If only the fact that an individual lost 12 percent or more of their excess body weight is used, critical distinctions may be missed between, for example, a person losing just over this amount and another losing 90 percent of their excess weight.

What exactly a regression tree is, and how it is used to predict weight loss is more easily understood by considering an example. The regression tree shown in FIG. 8 is based on one of the boosted CART trees estimated for implantable gastric stimulation patient screening according to a non-limiting embodiment of this invention. The tree has been trimmed back slightly from its estimated form for the sake of simplifying the illustration to make it fit more conveniently on a single page. In an embodiment, the original tree contains further subdivision of some of the terminal nodes, which are shown as colored boxes containing a predicted percentage change in excess body weight for patients who are sorted into the node. The regression tree is a representation of a set of rules for sorting patients based on variables observed prior to treatment, namely age, measures of obesity, and the patient's SF-36 individual item and summary scale scores. Given these data for a potential patient, the analysis begins at the top of the tree and the questions are answered at each node, moving in the direction indicated by the "Yes" and "No" arrows, until arrival at one of the colored terminal nodes or leaves.

Predicted weight change at each terminal node is the mean percentage change in excess body weight among implantable gastric stimulation trial patients who were sorted into the same terminal node. If the questionnaire answers of a prospective patient are run through the tree and one arrives at a red (or darkly shaded) node, it is known that the baseline predictor values for the new patient are similar to those for patients that did poorly under implantable gastric stimulation, either gaining weight or experiencing a clinically insignificant weight loss. Conversely, if running the new patient through the tree leads to a green (or lightly shaded) terminal node, it is known that the patient has baseline prognostic factors similar to patients with relatively favorable weight loss outcomes under implantable gastric stimulation.

Expressed in terms of the tree illustrated in FIG. 8, the general idea of the implantable gastric stimulation screening algorithm is to retain and treat prospective patients who are sorted into the green nodes, while rejecting those sorted into the red nodes. In actuality, given the use of boosting in conjunction with CART regression trees in one embodiment, the screening algorithm is not quite this simple. Instead of using weight loss predictions from a single regression tree, the screening model combines predictions from 250 distinct trees built in a sequence of bootstrap samples drawn from the observed implantable gastric stimulation trial data. Prospective patients are then retained for treatment if either the average of their predicted weight loss across bootstrap trees exceeds a target level, or the majority of boosted CART trees predict their weight loss will exceed the target level. In one embodiment, a target level of 12 percent excess weight loss is used, which is found to be satisfactory in terms of patient retention and the distribution of weight loss outcomes among selected patients.

Before detailing the process of combining multiple boosted trees, a description is first provided here on how the CART algorithm arrives at a single regression tree. CART, like other regression tree algorithms, builds trees recursively. Beginning with all observations concentrated in a single node, it divides the data into two groups according to a specific set of rules, thereby creating an intermediate tree with two terminal nodes. The same set of rules are then reapplied to the observations at each new terminal node, and this progressive subdivision of the data continues until the splitting rules allow no further splits at any terminal node. Denoting a tree with k terminal nodes by $T_k$, the typical CART tree growing process begins with $T_1$, a "stump" with no leaves, and progresses through a sequence of intermediate trees, $T_1$, $T_2$, $T_3$, $T_4$, and so on, until it reaches $T_{Max}$, the largest tree attainable in the sample under the algorithm rules.

In general, the maximal tree grossly overfits the training sample in that a smaller, intermediate tree would provide superior prediction in independent samples drawn from the same population. For single tree predictive modeling the CART algorithm uses cross-validation to alleviate this overfitting problem, "pruning" the maximal tree back to the tree size that minimizes validation sample prediction error. When prediction is based on a combination of a large number of boosted CART trees, however, Breiman has shown that there is little or no improvement in test sample prediction gained from pruning each individual tree. Heuristically, the reason for this is that the added error introduced into the individual tree predictors by overfitting boosted bootstrap training samples averages to nearly zero when predictions are combined from a sufficient number of boosted CART trees. Consequently, only unpruned CART trees are used and the description herein of the CART tree-building algorithm omits its pruning component.

Notably, the use of unpruned CART trees in conjunction with boosting has significant computational advantages. Simulation studies and applications to a range of real-world data sets indicate that the reduction in generalization error associated with boosting does not begin to level out until reaching an ensemble of approximately 250 boosted CART trees, which is the number adopted in the analysis of this embodiment. Applying the usual method of CART pruning based on 10-fold cross-validation in this context would require estimating 11 trees—(ten for cross-validated pruning, plus the final pruned tree built in the full training sample)—for each boosting cycle, a total of 11×250=2750 trees.

Building the maximal CART regression tree in a training sample, bootstrap or otherwise, requires three basic rules:

1. A rule for assigning a predicted value for the target variable at every terminal node.
2. A rule for splitting observations at the terminal nodes of each intermediate tree.
3. A rule for deciding when node observations will not be subdivided further.

The prediction rule is the easiest to describe. The target variable in the analysis used is the percentage change in the excess body weight of the implantable gastric stimulation trial patients by their last available follow-up. The predicted value for this target at any terminal node is simply its mean value for patients sorted into the node.

In the application of CART to the implantable gastric stimulation trial data according to this embodiment, observations at intermediate nodes are split based on whether a single ordinal or binary predictor variable is less than a threshold value. Patients at the node with values of the predictor below the threshold are sorted into one new node, while the remaining patients pass into another. The specific splitting rule is to consider every possible threshold value for all available predictors, and then split node subjects using the predictor and threshold combination yielding the largest reduction in the mean of squared prediction error for these subjects. Finally, there is no further subdivision of a node when the number of patients at the node reaches or falls below a preset minimum node size of 10 subjects, or when there is no available split that will improve mean squared prediction error.

Table 2 provides a more formal statement of the CART tree-building algorithm. It should be noted that both the forgoing description and that in Table 2 are limited to the features of the CART algorithm as used in the analysis of this non-limiting embodiment. The CART algorithm can, for instance, accommodate splits on predictors with multiple categories that have no natural low-to-high ordering. Since the predictors used in this embodiment are limited to variables that are either ordinal or binary, no use of this feature is made. Likewise, Breiman and colleagues original conception of CART includes rules for handling missing values of the input predictors using what they call "surrogate splits." Missing predictor values in the data are limited to an inconsequentially small number of SF-36 item responses that were imputed by standard methods. It may not be clear in what sense the binary splits within the CART algorithm constitute a sequence of local regressions. To see this, let the best available split at the $t^{th}$ node be to assign the $i^{th}$ subject at t to the left child node, $t_L$, if $x_{ij^*} > c^*$. Otherwise the subject is sorted into the right hand child $t_R$. The resulting predictions for the target variable are the same as would be gotten by fitting an ordinary least squares regression model of the form $$y_i = \beta_0 + \beta_1 D_i + \epsilon_i$$

to the $n_t$ observations at node t. Here $D_i = 1$ when $x_{ij^*} > c^*$ and is zero otherwise, $\beta_0$ and $\beta_1$ are parameters to be estimated, and $\epsilon_i$ is a random error term with mean zero. The CART algorithm predicted values for subjects sorted into $t_L$ and $t_R$ can be expressed in terms of the least squares estimates of $\beta_0$ and $\beta_1$, specifically $\hat{y}(t_L) = \beta_0 + \beta_1$ and $\hat{y}(t_R) = \beta_0$.

subsets of the training sample. The method of choosing splits at each node implies that the estimated tree is unaltered by the inclusion of irrelevant predictors, or by the omission of any monotone transformation of an included predictor that might be more closely correlated with the target. The flexibility and adaptability of the CART algorithm are not gained without cost. Specifically, CART's advantages over more restrictive parametric regression methods come from limiting itself to the class of models attainable using only binary splits at each intermediate node, combined with what is called a "locally greedy" search for the best available split. Neither proscription is innocuous, but the resulting class of models has proved useful in a broad array of circumstances, contributing to the widespread use of the CART algorithm.

The use of boosting in conjunction with CART in this embodiment means the CART tree building algorithm is repeatedly applied in a sequence of bootstrap samples drawn from the observed implantable gastric stimulation trial sample. Bootstrap samples are obtained by making N random draws from an observed sample of size N, replacing selected observations back into the sample after each draw. In the standard case, each sample observation has a 1/N probability of being selected into the bootstrap sample on each draw. The resulting bootstrap sample is distinct from the observed sample, with some observations appearing multiple times while others may not appear at all. Boosting begins with building a CART tree in a standard bootstrap sample, drawn with a 1/N sampling probability assigned to

TABLE 2

CART Regression Tree Building Algorithm

Notation:

$T_k$ denotes a tree with k terminal nodes or "leaves"
t is the set of training sample subjects sorted into the $t^{th}$ node of the tree
$n_t$ is the number of sample subjects sorted into the $t^{th}$ node
$t_L$ and $t_R$ are sets of subjects sorted into the left and right hand child nodes of node t by a binary split of subjects in t
$y_i$ is the value of the target variable for $i^{th}$ training sample subject
$\hat{y}(t)$ is the predicted value of this target for subjects sorted into node t $$\text{err}(t) = \sum_{i \in t} (y_i - \hat{y}(t))^2 \text{ is the sum of squared prediction errors for subjects in node t}$$

$x_i = (x_{1i}, x_{2i}, \ldots x_{Ki})$ is the vector of ordinal or binary predictors observed for the $i^{th}$ subject
$s(x_{ij} > c; t)$ is a rule for splitting node t into child nodes $t_L$ and $t_R$, with subjects passing to $t_L$ if their $j^{th}$ predictor exceeds the threshold c and to $t_R$ if not.

Algorithm:
Rules:

1. Prediction: The predicted value of $y_i$ for subjects in node t is $\hat{y}(t) = \frac{1}{n} \sum_{i \in t} y_i$.

2. Splitting: Choose the split $s(x_{ij} > c; t)$ to maximize the resulting reduction in err(t) defined by $\Delta \text{err}(t) = [\text{err}(t) - \text{err}(t_L) - \text{err}(t_R)]$.
3. Stopping: The $t^{th}$ node is not split if $n_t \leq 10$ or the best possible split is such that $\Delta \text{err}(t) = 0$.

Beginning with a single node tree $T_1$, split subjects at the terminal nodes of each intermediate tree $T_1, T_2, T_3, T_4 \ldots$, according to rules 1 through 3 until reaching the maximal tree, $T_{Max}$, where no further splits are allowed at any terminal node.

Notably the CART tree-building algorithm requires no parametric assumptions on the relationship between the target variable and the predictors. It can accommodate nonlinear relationships between the predictors and the target, as well as heterogeneity in these relationships across each observation. Thereafter the sampling probabilities used to draw the $j^{th}$ bootstrap training sample under boosting are a function of prediction errors in the previous (j−1) bootstraps, and evolve adaptively to give progressively greater weight to difficult to predict observations.

The manner in which these sampling weights evolve depends on the specific boosting algorithm employed. Breiman's adaptive resampling and combining or "arcing" variant of the tree boosting algorithm first suggested by Freund and Schapire is used in this embodiment. Freund, Y., et al., "Experiments with a new boosting algorithm," Machine learning: Porc. 13$^{th}$ Ann. Conf., San Francisco, Morgan Kaufman, 1996, pp. 148–156. The details of this algorithm are given in Table 3. CART trees built in a total of 250 boosted bootstrap training samples are estimated and combined in this embodiment. Experimentation with larger numbers of boosting cycles (ranging up to 1000) showed minimal improvement in prediction over an ensemble of 250 trees.

The process of estimating the boosted CART model and then applying it to the screening of new patients is depicted by the flow chart in FIG. 9. The boxes connected by narrow arrows represent the process of building the boosted CART trees. The wider gray arrows represent the process of screening new implantable gastric stimulation treatment candidates. Practical implementation of predictive patient screening using the boosted CART trees is straightforward. All that is needed from a potential patient is their age, sex, height, weight and a completed SF-36 survey. A simple computer program can then translate this information into the set of predictors used in building the CART trees, and then run this data through each of the ensemble trees, arriving at 250 predictions of excess weight loss under implantable gastric stimulation treatment. With a 12 percent excess weight loss target, the patient is accepted for implantable gastric stimulation treatment if the average of these 250 predictions is 12 percent or more, or if more than half the boosted CART trees predict excess weight loss of 12 percent or more. Patients with model predictions that fail this criterion are referred to other obesity treatment options.

TABLE 3

Breiman's Version of Boosting

Notation:

$y_i$, $i = 1, \ldots, N$, is the value of the target variable for $i^{th}$ training sample subject
$\hat{y}_i^j$ is the value predicted for the target variable in the $i^{th}$ subject by the maximal CART tree built in the $j^{th}$ bootstrap training sample.

$$e_{ij} = \sum_{k=1}^{j} (y_i - \hat{y}_i^k)^2 \text{ is the sum of the squared prediction errors for the}$$

$i^{th}$ subject over CART trees built in bootstrap training samples $1, \ldots, j$.
$p_{ij}$ is $i^{th}$ subject's probability of being selected into the $j^{th}$ bootstrap training sample on each draw.
K is the total number of boosted CART trees to be combined.
Algorithm:

Initiate the algorithm by drawing bootstrap training sample 1 with $p_{i1} = \frac{1}{N}$ for all i.

1. Construct the maximal CART regression tree in the $j^{th}$ bootstrap training sample and apply trees $1, \ldots, j$ to the observed training sample, obtaining predicted values $\hat{y}_i^1, \ldots, \hat{y}_i^j$ for all i.

2. Use these predictions to calculate $e_{ij} = \sum_{k=1}^{j} (y_i - \hat{y}_i^k)^2$ for all i.

TABLE 3-continued

Breiman's Version of Boosting

3. Draw bootstrap sample (j + 1) using sampling probabilities $$p_{i(j+1)} = \frac{(1 + e_{ij}^4)}{\sum_{i=1}^{N} (1 + e_{ij}^4)}.$$

Repeat steps 1 through 3 until a total of K boosted CART trees are obtained. Combine predictions $\hat{y}_i^1, \ldots, \hat{y}_i^K$ by averaging across trees or majority voting (e.g., subject i is predicted to have a value of the target variable above some desired threshold level if $\hat{y}_i^j$ is greater than this threshold in more than half of the K trees).

C. The Effects of Screening on Patient Retention and Weight Loss Outcomes

This section describes the results of estimating the boosted CART prediction model in the full sample of implantable gastric stimulation trial patients, and then using the estimated model to screen these same patients. In the terminology of data mining, the statistics presented in this section are "resubstitution" estimates, since they are obtained by applying the predictive model to the same sample used to train it.

Resubstitution estimates are free of generalization error associated with applying a predictive model outside the estimation sample. They thus provide an optimistic picture of how the predictive screening model will perform when applied to newly recruited implantable gastric stimulation treatment candidates. These estimates are presented primarily because they are conventional. In the empirical medical literature, and in many other contexts, most assessments of the accuracy and usefulness of statistical models focus exclusively on within-sample performance, as measured by resubstitution estimates of the average error and related statistics. For the implantable gastric stimulation screening problem it turns out that this bow to convention is relatively inconsequential. As shown by the test sample validation evidence presented in the next section, there is only a slight deterioration in the predictive performance of the boosted CART model when moving from the training sample used for estimation to hold-out test samples.

As shown in Table 4 herein, if only the patients selected by the CART predictive screening algorithm were implanted, mean percentage excess weight loss by last follow-up among all implantable gastric stimulation patients would nearly triple, rising from 9.6 percent to 28.1 percent. Predictive screening retains 38.1 percent (96 out of 252) implanted patients in the pooled implantable gastric stimulation trial sample. All of the retained subjects lose at least some weight by their last available follow-up, and nearly 90 percent of retained patients lose 5 percent or more of their implant body weight. A weight loss greater than or equal to 5 percent of body weight is of particular salience given that it has been identified as clinically significant in studies of the health benefits of modest weight loss. Specifically weight losses of this magnitude have been found to significantly reduce the risk of cardiovascular disease, prevent or delay the onset of Type II diabetes, and improve control of hypertension and dyslipidemia. Based on this evidence, there are substantive health benefits associated with implantable gastric stimulation treatment in nearly 90 percent of patients selected by predictive screening.

TABLE 4

Predictive Screening, Weight Loss Outcomes and Patient Retention

|  | All Studies Pooled (N = 252) | USA O-01 (N = 103) | USA O-02 (N = 30) | Europe O-01 (N = 67) | Europe O-02 (N = 52) |
| --- | --- | --- | --- | --- | --- |
| Mean % EWL Without Screening (Implant to Last Follow-Up) | 9.6% [7.2, 12.0] | 3.7% [0.4, 7.0] | 10.6% [2.7, 18.5] | 11.7% [6.4, 16.9] | 18.0% [13.0, 23.0] |
| Mean % EWL With Screening (Implant to Last Follow-Up) | 28.1% [24.5, 31.6] | 29.6% [19.9, 39.3] | 30.9% [12.9, 48.8] | 27.3% [20.2, 34.3] | 27.3% [22.9, 31.6] |
| Screening-Based Increase in Mean Weight Loss | 192.2% | 696.2% | 190.4% | 133.8% | 51.0% |
| Screened Patients Retained | 38.1% | 17.5% | 33.3% | 47.8% | 69.2% |
| Share of Retained Patients Losing Any Weight by Last Follow-up | 100.0% | 100.0% | 100.0% | 100.0% | 100.0% |
| Share of Retained Patients Losing 5% of Implant Weight False Positive Rate: | 88.5% | 88.9% | 90.0% | 87.5% | 88.9% |
| Retention Rate for Patients With <5% Weight Loss False Negative Rate: | 4.4% | 1.9% | 3.3% | 6.0% | 4.4% |
| Rejection Rate for Patients With 5% Weight Loss | 5.2% | 6.8% | 10.0% | 4.5% | 0.0% |

Table Notes: Percent excess weight loss (% EWL) calcuated using the 1983 Metropolitan Life estimates of ideal body weight by height and sex. Time from implant to last available follow-up is 18.6 months for the US O-01 study, 9.0 months for the US O-02 study, 22.4 months for the Europe O-01 trial, and 9.0 months for Europe O-02 trial. Figures in brackets are 95% confidence intervals for mean % EWL.

The bottom section of Table 4 addresses the sensitivity and specificity of the predictive screening algorithm for identifying patients who will or will not experience a clinically significant weight loss of 5 percent or more under implantable gastric stimulation treatment. In medical testing terminology, sensitivity is defined as the likelihood that persons with the targeted event or condition will be captured by the screen. Specificity refers to the likelihood that persons without the targeted event or condition will be correctly rejected by the screen. The greater the sensitivity of the test, the lower the rate of false positive results. The greater the specificity of the test the lower the rate of false negatives. For the predictive screening algorithm, both of these rates are well below 10 percent for the case of detecting weight losses of 5 percent or more under implantable gastric stimulation. Predictive screening incorrectly retains only 4.4 percent implantable gastric stimulation trial patients who lost less than 5 percent of their implant body weight. Among implantable gastric stimulation patients who surpass this clinically significant weight loss threshold, the screen rejects only 5.2 percent.

In most instances the statistics shown in Table 4 are remarkably similar across the four sets of implantable gastric stimulation trial subjects. Mean excess weight loss among patients retained in every trial falls in a narrow range between 27 and 31 percent, all retained patients in every trial lose weight, and 88 to 90 percent of retained subjects from all four trial lose 5 percent or more of their implant body weight under implantable gastric stimulation. Similarly, false positive and negative rates defined in terms of a 5 percent weight loss threshold are uniformly 10 percent or less across studies. The notable exceptions to this pattern of similarity are in the patient retention rates and the amount of screening-based improvement weight loss outcomes. Compared with the European studies, a markedly lower proportion of patients are retained by screening in the United States samples, and this lower retention leads to a commensurately larger screening-based improvement in weight loss outcomes.

It is notable that within the United States and Europe patient retention rates are higher in the later studies that incorporate explicit dietary recommendations, and that the highest retention rate overall is in the only studying coupling implantable gastric stimulation with a formal reduced-calorie diet and nutritional counseling. This result is not unexpected given that the inclusion of a dietary component likely acts as a screening device in itself, eliminating some prospective patients who are unable or unwilling to exercise any dietary restraint. The resulting selection of patients would then be more likely to attempt to restrain their eating, and, as a result, more likely to eat in response to appetite cues and to benefit from the effects of implantable gastric stimulation on hunger and satiety.

FIGS. 10 and 11 contain plots of mean percent excess weight change by month for patients selected and rejected by the CART screening algorithm in each of the four implantable gastric stimulation trials conducted in the US and Europe. In calculating the plotted means, missing weight change follow-up data were imputed by linear interpolation, or by carrying forward the last available observation. The main effect of this imputation is to yield slightly more conservative estimates of average excess weight loss at the final plotted endpoint; at the earlier months, the means computed with and without the imputations are nearly identical. Apart from the marked difference in weight change in selected and rejected patients, there are two features of FIGS. 10 and 11 that are of particular note. First, is the absence of any evidence of weight regain among the implantable gastric stimulation patients selected by the screening algorithm. In any non-invasive therapy associated with the degree of weight loss experienced by the selected implantable gastric stimulation subjects' weight change trajectories would be expected to show signs of regain after 6 months. Instead, in all studies weight change trajectories in the selected implantable gastric stimulation patients are either level or still moving downward beyond 6 months from implant. Secondly, while weight loss is more rapid in the later generation of studies that pair implantable gastric stimulation with dietary recommendations, patients selected from the first-generation trials, who received no dietary advice, eventually attain similar levels of mean percentage excess weight loss. This suggests that while a dietary component helps to accelerate initial weight loss, it is not essential to weight loss under implantable gastric stimulation treatment.

Figure 12:
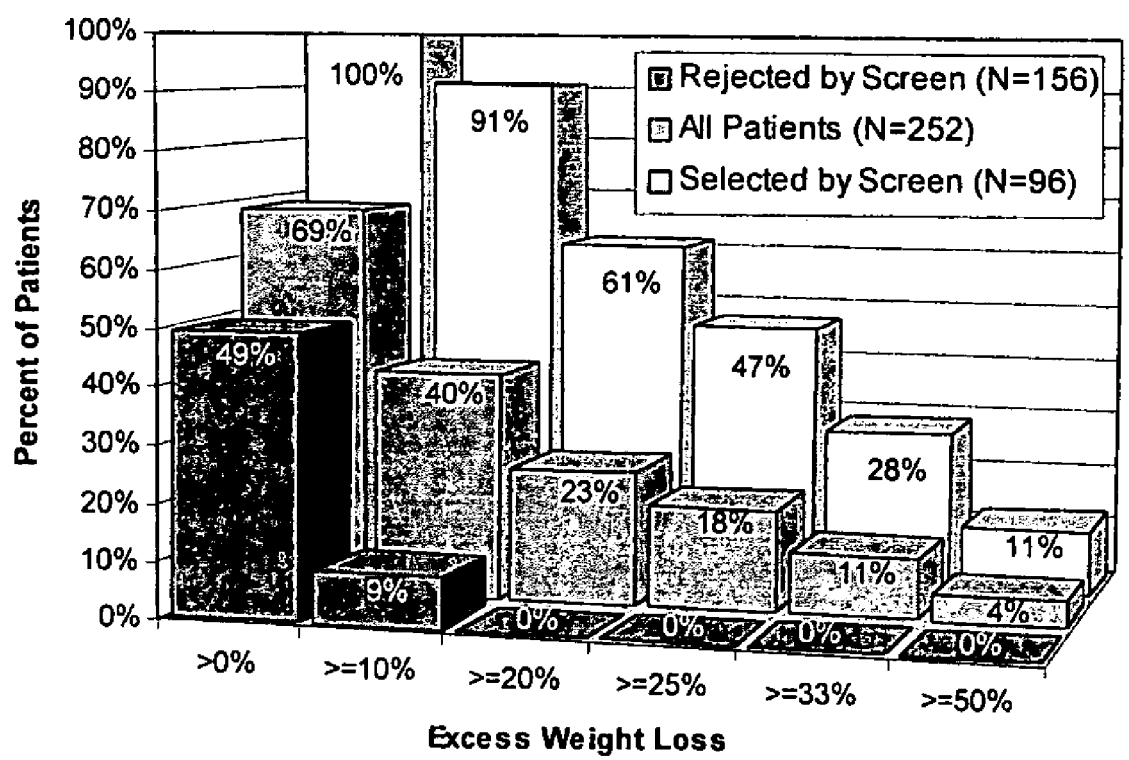
FIG. 12 is a bar graph showing the percentage of trial subjects indicated in Table 1 achieving the various indicated excess weight losses for all the trial subjects, as well as the trial subjects "rejected" and "selected" by a predictive model developed according to an embodiment of this invention.

The distribution of percentage excess weight loss among all implantable gastric stimulation trial subjects, and among patients selected and rejected by the predictive screening algorithm is shown in FIG. 12. Analogous figures showing the distribution of excess weight loss for each trial separately are provided in FIGS. 16–19. More than 60 percent of retained subjects lose more than 20 percent of their excess weight at implant by their last follow-up. Nearly half of retained subjects (47 percent) lose a quarter or more of their excess weight, while 28 percent of have weight losses equal to at least a third of their excess body weight at implant. The specificity of the screening algorithm in selecting patients who will attain substantial weight losses under implantable gastric stimulation is evident in the fact that not a single rejected patient loses 20 percent or more of their excess weight.

D. Test Sample Validation

The resubstitution estimates of screening algorithm performance in the preceding section are likely to be optimistically biased. The statistics presented in this section avoid this bias by incorporating an estimate of the generalization error that occurs when the predictive model is applied outside the sample used to train it. This is done by repeatedly training the screening model in randomly selected subsets of the observed data and then assessing its performance in test samples comprised only of the data not used for training.

The test-set validation procedure used is a variation on k-fold cross-validation, and is commonly used for validating prediction algorithms in the statistical literature on data mining. The basic steps in the procedure are as follows:

1. Randomly select 10 percent (25 of 252 observations) of the full implantable gastric stimulation trial sample and set it aside.

2. Use the remaining 90 percent of the sample to build 250 boosted CART trees for prediction of percent excess weight loss as described herein.

3. Run the 10 percent hold-out sample through the 250 boosted CART trees, recording subjects as retained if their predicted excess weight loss averages at least 12 percent across all trees, or if more than half of the trees predict 12 percent or more excess weight loss.

Steps 1 through 3 are repeated 100 times. Statistics on retained and rejected test sample subjects are then averaged across the 100 replications. In effect, each replication assumes an observation of only a randomly chosen 90 percent subset of the full sample. Then, one considers how the predictive screening model trained in this subset does in selecting successful implantable gastric stimulation patients in "new" treatment candidates, which are represented by the 10 percent of subjects held out of training sample. Averaging statistics across 100 randomly selected combinations of 90 percent training and 10 percent test samples reduces the associated sampling variation, providing more stable estimates of test sample performance. E.g., see Hjorth, J., Computer Intensive Statistical Methods: Validation, Model Selection and Bootstrap, London: Chapman Hill, 1994.

It is important to note that both the full sample estimation of the boosted CART model and the test set validation experiment in the case of this particular embodiment were performed exactly once. There was no iteration over this process to revise the predictive model and improve apparent test set performance. This avoids reintroducing the optimistic bias inherent in the resubstitution estimates of model performance into the test set estimates.

Table 5 herein compares test sample estimates of the effects of predictive screening on patient retention and weight loss to the full sample resubstitution estimates. The test set statistics are remarkably similar to those obtained in the full sample. This similarity is also evident in FIGS. 13–15, which compare test sample and resubstitution estimates of mean excess weight loss by month, and of the distribution of excess weight loss for patients retained by the screening algorithm. Generalization error leads to retention of a slightly higher share of test sample patients, and these retained patients have lower average weight loss. Nonetheless, test sample estimates of screening-based gains in excess weight loss are nearly as large as the full sample estimates. Retained test sample subjects have mean excess weight loss of 25.4 percent, a figure equal to nine-tenths of the 28.1 percent resubstitution estimate.

TABLE 5

Predictive Screening, Weight Loss Outcomes and Patient Retention: Full Estimation Sample vs. Hold-Out Test Sample Performance

| | Sample | All Studies Pooled | USA O-01 | USA O-02 | Europe O-02 | Europe O-02 |
|---|---|---|---|---|---|---|
| Mean % EWL With Screening (Implant to Last Follow-Up) | Full | 28.1% | 29.6% | 30.9% | 27.3% | 27.3% |
| | Test | 25.4% | 22.5% | 31.2% | 25.8% | 25.0% |
| Screening-Based Increase in Mean Weight Loss | Full | 192.2% | 696.2% | 190.4% | 133.8% | 51.0% |
| | Test | 162.9% | 537.2% | 153.2% | 105.1% | 46.7% |
| Screened Patients Retained | Full | 38.1% | 17.5% | 33.3% | 47.8% | 69.2% |
| | Test | 39.4% | 19.1% | 36.0% | 50.1% | 69.2% |
| Retained Patients Losing Any Weight by Last Follow-up | Full | 100.0% | 100.0% | 100.0% | 100.0% | 100.0% |
| | Test | 95.7% | 89.6% | 97.2% | 97.5% | 97.2% |
| Retained Patients Losing 5% of Implant Weight | Full | 88.5% | 88.9% | 90.0% | 87.5% | 88.9% |
| | Test | 82.0% | 66.7% | 92.5% | 84.3% | 85.4% |
| False Positive Rate: Retention Rate for Patients With <5% Weight Loss | Full | 4.4% | 1.9% | 3.3% | 6.0% | 4.4% |
| | Test | 7.1% | 6.4% | 2.7% | 7.8% | 10.1% |
| False Negative Rate: Rejection Rate for Patients With 5% Weight Loss | Full | 5.2% | 6.8% | 10.0% | 4.5% | 0.0% |
| | Test | 6.7% | 8.4% | 9.8% | 6.1% | 2.1% |

Table Notes: Percent excess weight loss (% EWL) calculated using the 1983 Metropolitan Life estimates of ideal body weight by height and sex. Time from implant to last available follow-up is 18.6 months for the US O-01 study, 9.0 months for the US O-02 study, 22.4 months for the Europe O-01 trial, and 9.0 months for Europe O-02 trial.

Figure 13:
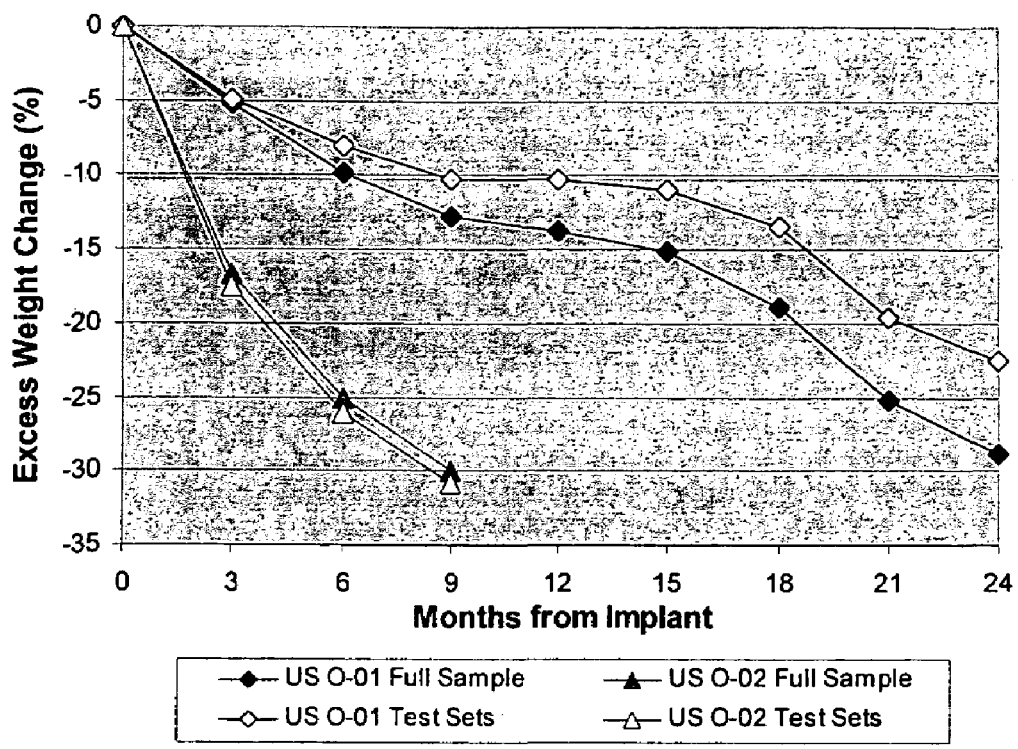
FIGS. 13–14 are plots of excess weight change (%) as a function of months from implant for the trial patients for the US and European trials, respectively, indicated in Table 1 as between all the trial subjects and test sets thereof using a predictive model developed in accordance with one embodiment of the invention.
Figure 14:
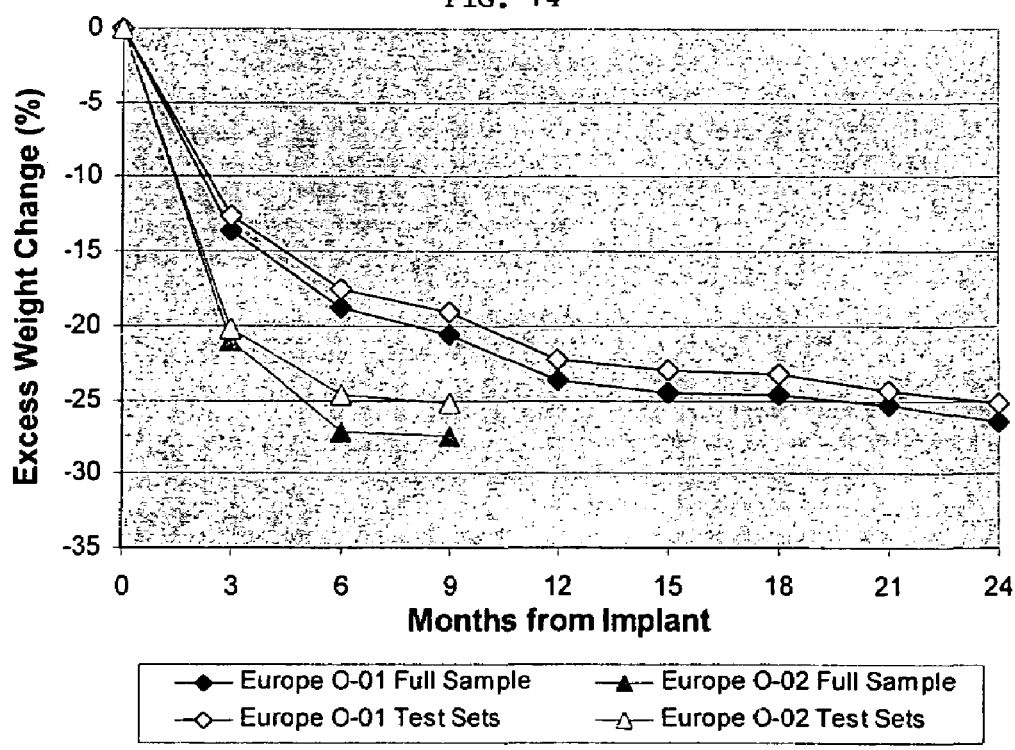
Figure 15:
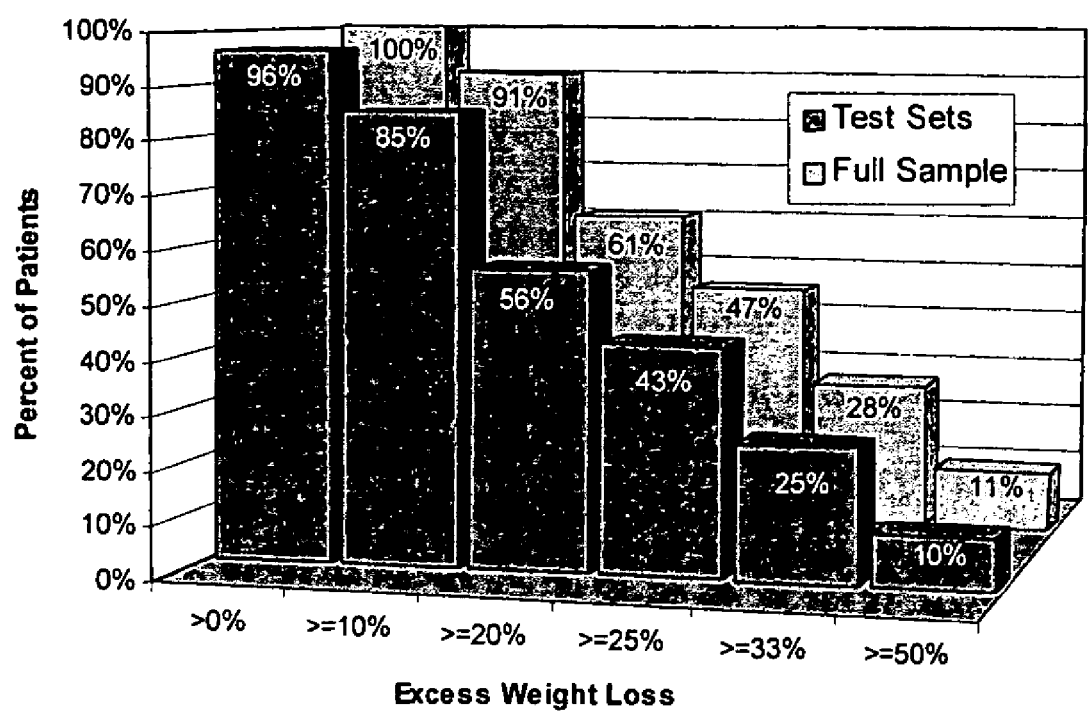
FIG. 15 is a bar graph showing the percentage of trial subjects indicated in Table 1 achieving the various indicated excess weight losses for all the trial subjects and test sets thereof by a predictive model developed according to an embodiment of this invention.
Figure 16:
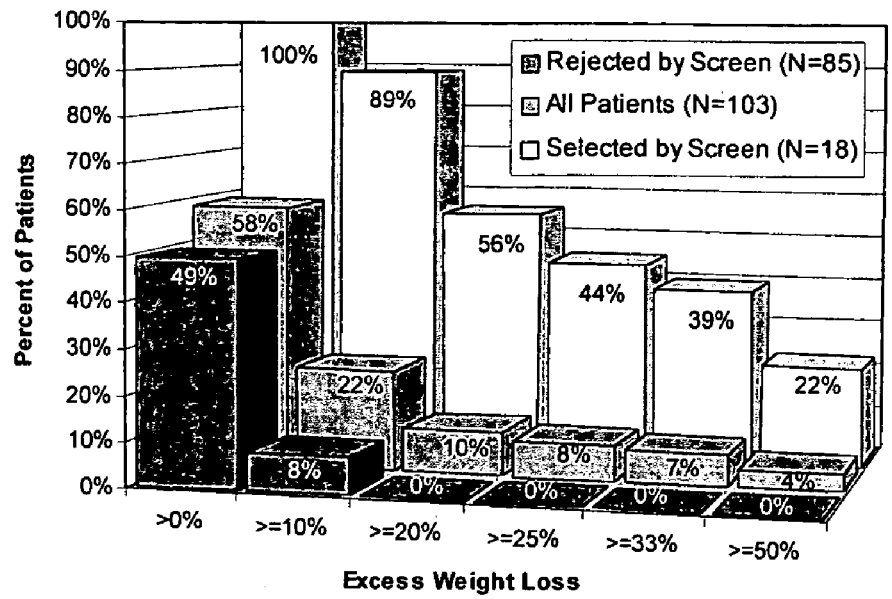
FIGS. 16 and 17 are bar graphs showing the percentage of trial subjects in the U.S. trials indicated in Table 1 achieving the various indicated excess weight losses by the last follow-up for all the trial subjects, as well as the trial subjects "rejected" and "selected" by a predictive model developed according to an embodiment of this invention.
Figure 17:
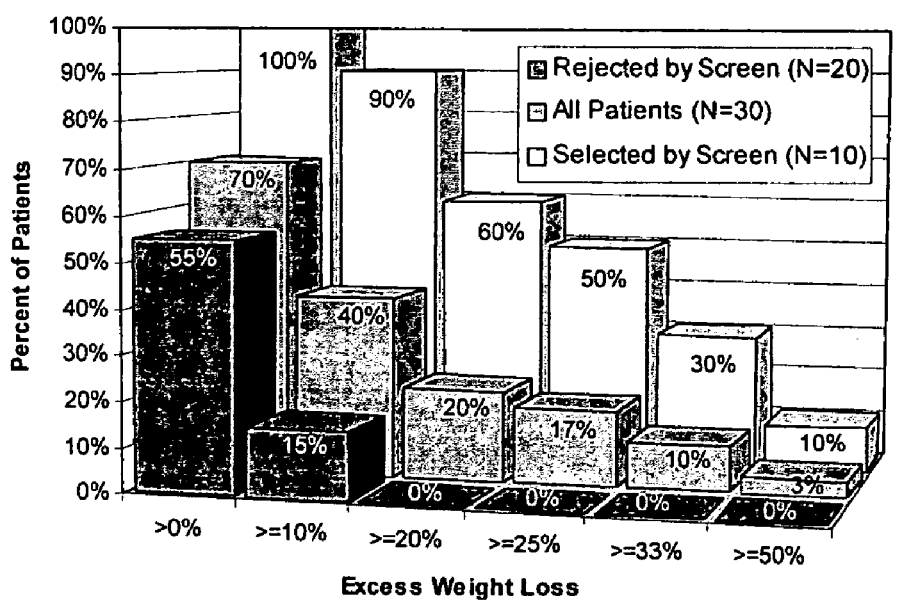
Figure 18:
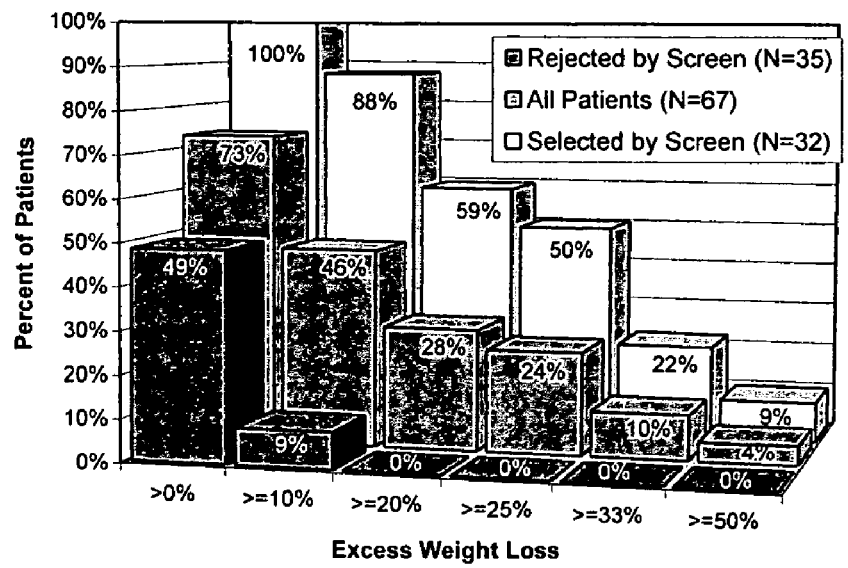
FIGS. 18 and 19 are bar graphs showing the percentage of trial subjects in the European trials indicated in Table 1 achieving the various indicated excess weight losses by the last follow-up for all the trial subjects, as well as the trial subjects "rejected" and "selected" by a predictive model developed according to an embodiment of this invention.
Figure 19:
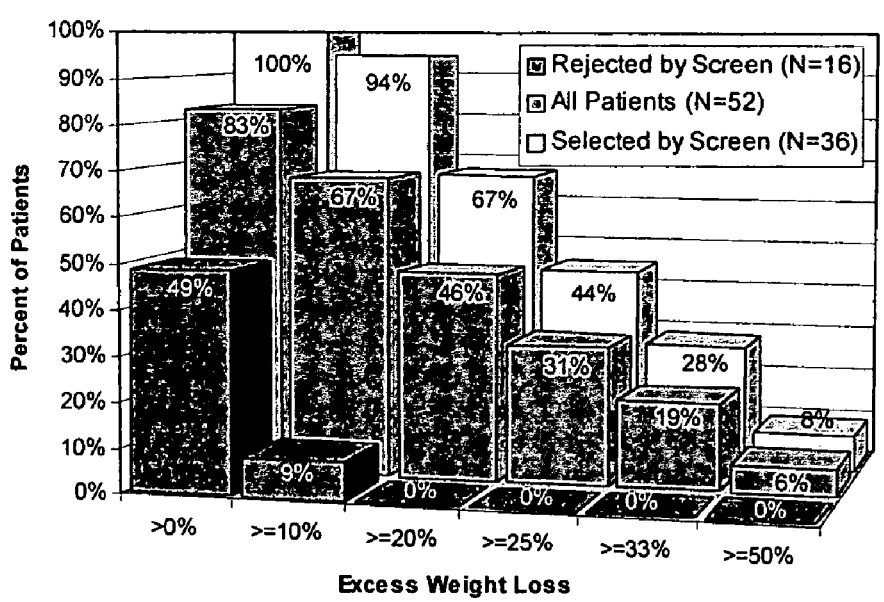
Figure 20:
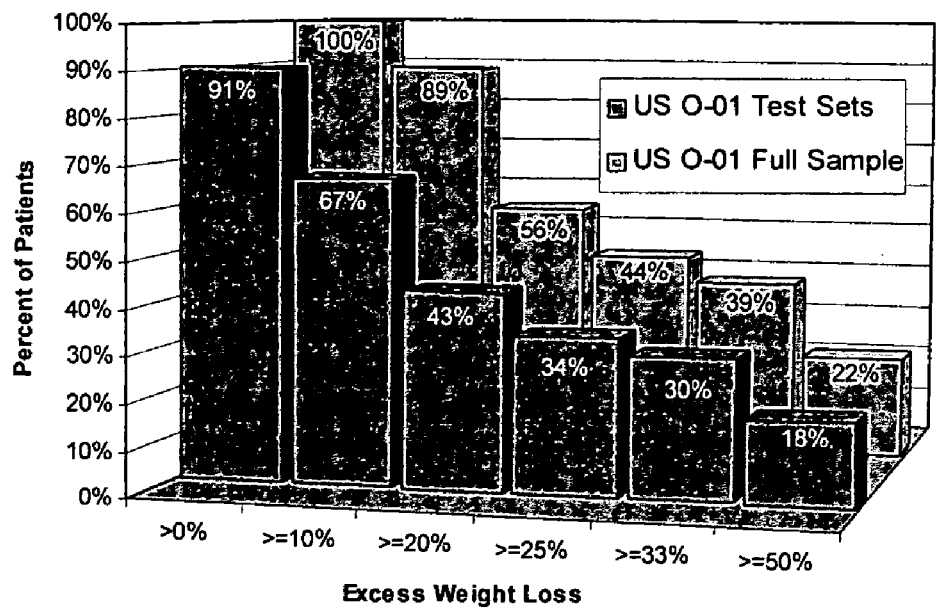
FIGS. 20 and 21 are bar graphs showing the percentage of trial subjects in the U.S. trials indicated in Table 1 achieving the various indicated excess weight losses by the last follow-up for all the trial subjects, based on the test sets and the full samples analyzed by the predictive model developed according to an embodiment of this invention.
Figure 21:
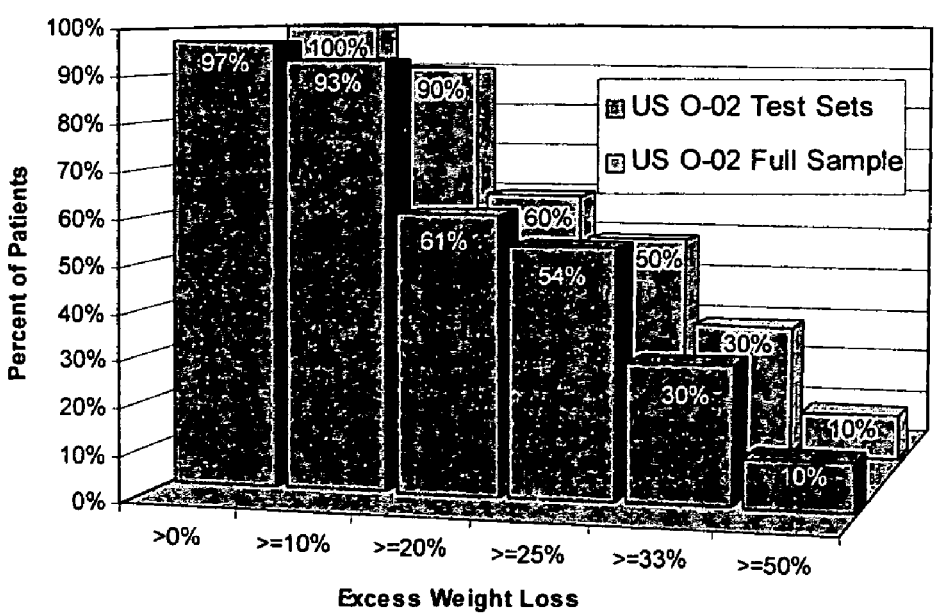
Figure 22:
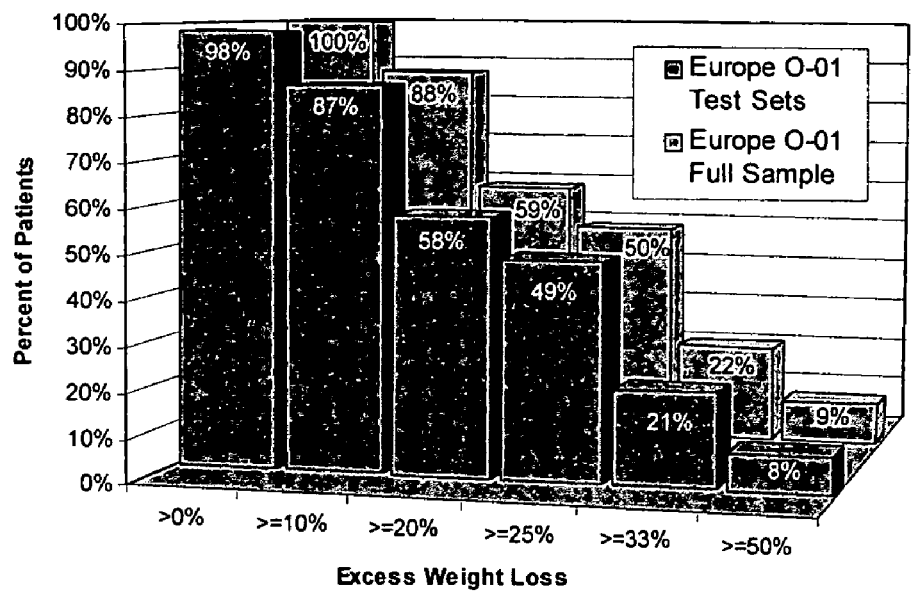
FIGS. 22 and 23 are bar graphs showing the percentage of trial subjects in the European trials indicated in Table 1 achieving the various indicated excess weight losses by the last follow-up for all the trial subjects, based on the test sets and the full samples analyzed by the predictive model developed according to an embodiment of this invention.
Figure 23:
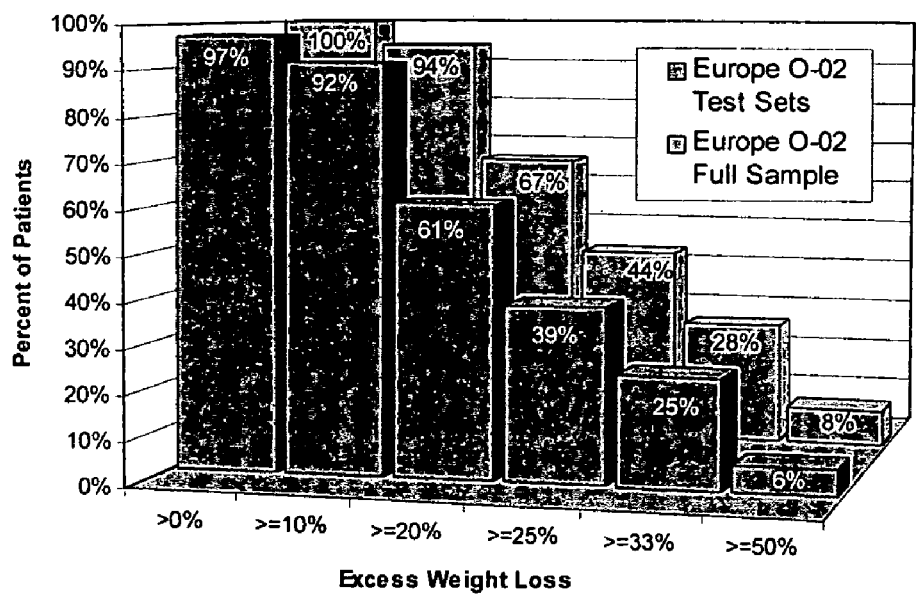

The remaining statistics in Table 5, as well as those displayed in FIGS. 13–15, indicate similarly modest declines in screening algorithm performance when it is applied to hold-out test samples. More than 90 percent of retained test sample subjects lose weight under implantable gastric stimulation, and more than 80 percent attain the clinically significant weight loss threshold of 5 percent or more of initial body weight. Test sample false positive and negative rates for the case of detecting a 5 percent weight loss are near or below 10 percent across all trials. For three of the four implantable gastric stimulation trials, the plots in FIGS. 13 and 14 of resubstitution and test sample estimates of excess weight loss by month for patients retained by screening lie nearly on top of one another. Likewise the test sample relative frequencies of excess weight loss by category shown in FIG. 15 differ from the full sample results by 10 percent or less in all categories. Comparisons between estimation and test sample distributions of excess weight loss within each implantable gastric stimulation trial separately, as shown in FIGS. 20–23, lead to largely similar results.

Notably, the difference between the full sample and hold-out test sample estimates of screening algorithm performance is greatest for patients from the United States O-01 trial. This is attributed at least in part to use of stimulation settings that subsequent experience suggests were sub-optimal for many patients. These problems were possibly compounded by the randomized trial protocol, which did not allow device revisions or adjustments to stimulation settings in the first seven months after implant. It is likely that such device problems caused some patients who would have otherwise done well under implantable gastric stimulation to lose little or no weight and discontinue treatment. Under test sample validation, the screening algorithm would tend to retain such patients based on their favorable prognostic factors, despite their lack of weight loss. Such a pattern could account for the larger deterioration in evident screening performance between resubstitution and test sample estimates for the United State O-01 trial.

E. Variables Determining Patient Selection

Further support for the validity of the predictive screening model can be drawn from considering the nature and direction of the correlations it uses to predict weight loss. Similar correlations have been reported in a range of existing empirical studies of weight loss and weight-related behaviors. The fact that the relationships exploited by the predictive screening model are not unique to the implantable gastric stimulation trial sample suggests that these correlations are likely to be stable enough to provide a useful basis for prediction in future samples of severely obese implantable gastric stimulation treatment candidates.

Understanding the way in which the CART model predicts weight loss outcomes is complicated by the use of boosting. With single tree prediction, visual inspection of the estimated CART decision tree is often sufficient to identify key predictors and the direction of their association with the target variable. In this application, however, there is not merely one tree but 250, comprised of more than 11,000 logical statements for sorting implantable gastric stimulation treatment candidates. Since little can be gleaned from visual inspection of such a large set of decision rules a more systematic analysis is required.

The approach taken here has two major components. First, the relative variable importance scores defined by Breiman et al. are used to identify which of 58 predictors used in the CART analysis play the largest roles in predicting excess weight loss. See, Breiman et al., Classification and Regression Trees, New York: Chapman Hall: 1984. CART relative importance scores are measures of the amount of variation in percentage excess weight change that can be accounted for by individual predictors. A score of 10, for example, indicates that a variable can predict one tenth as much variation in weight change as the most important variable, which receives a score of 100. These scores are calculated for each of the 250 boosted CART regression trees estimated in the full implantable gastric stimulation trial sample, and then averaged across trees. A formal definition of relative importance scores and a complete listing of scores for all 58 predictors is described in the subsection below.

1. Variable Importance Scores

This subsection provides a formal description of the relative variable importance scores defined by Breiman et al., referenced above, devoted to the CART algorithm. These scores, which are defined for individual CART trees, are measures of the amount of variation in the target variable that can be explained by variation in a particular predictor. The scores are normalized so that the most important predictor receives a score of 100 and serves as the metric for gauging the importance of the remaining predictors. It is critical to note that importance scores are measures of predictive "potential" rather than "actual" contribution to prediction. Important predictors that are highly correlated will have similarly high important scores even if some of these predictors are seldom or never used for splitting in the estimated CART decision tree.

To accommodate the use of boosting, variable importance scores are averaged across the ensemble of 250 boosted trees. Average scores are re-normalized by dividing by the highest average score and multiplying by 100. Table 6 contains a list of the resulting scores for the 58 predictors entering the CART model of excess weight loss. Predictors appear in the table ranked in descending order of their relative importance scores.

To define CART relative importance scores, the following notations were adopted:

$N_{Max}$ is the total number of nodes in the maximal tree, $T_{Max}$, built in a training sample, just as described in Box 1 of the main text of this document;

t is the set of training sample subjects sorted into the $t^{th}$ node of $T_{Max}$;

$\Delta err(t; j)^*$ is the largest improvement in the sum of squared prediction errors over subjects in t obtainable from any binary split of these subjects based on the value of the $j^{th}$ predictor; and if t is a terminal node of $T_{Max}$, then $\Delta err(t; j)^* = 0$ for all j.

Note that the definition of $\Delta err(t; j)^*$ is analogous as that given for $\Delta err(t)$ in Table 2, save that $\Delta err(t; j)^*$ refers to the change in squared prediction error associated with the best available split on a particular predictor. This split could happen coincide with the split actually chosen by the CART tree building algorithm in constructing $T_{Max}$, but in most case it will not. Indeed, it is possible that the $j^{th}$ predictor happens not to be used for splitting at any intermediate node of $T_{Max}$.

Using the above notation, the importance of the $j^{th}$ predictor is measured by the sum of $\Delta err(t; j)^*$ across all nodes of $T_{Max}$, namely $$I_j = \sum_{t=1}^{N_{Max}} \Delta err(t; j)^*.$$

The relative importance score for the $j^{th}$ predictor is $$I_j^* = \left(\frac{I_j}{I^*}\right) \times 100$$

where $I^*$ is the value of $I_j$ for the most important predictor.

TABLE 6

Predictors (Pred.) 1–58 for CART Analysis of Percentage Excess Weight Loss, Ranked by Variable Importance

| Pred. | Variable Group | Variable | Variable Description | Importance Score |
|---|---|---|---|---|
| 1 | Baseline Obesity Measures | BMI0 | Implant BMI (kg/m2) | 100.0 |
| 2 | Baseline Obesity Measures | EWGT0 | Implant Excess Body Weight (kg) | 99.5 |
| 3 | Baseline Obesity Measures | WGT0 | Implant Weight (kg) | 94.4 |
| 4 | Baseline Obesity Measures | EWGTPCNT | Excess Weight at Baseline as % of 1983 Met Life Ideal Weight | 78.3 |
| 5 | Patient Age | AGE | Age at Implant | 65.2 |
| 6 | SF-36 Emotional Well Being Score Variables | EMWB | Emotional Well Being Score | 52.9 |
| 7 | SF-36 Physical Health Composite Score Variables | PHF | NEMC Physical Health Composite Score | 52.8 |
| 8 | SF-36 Mental Health Composite Score Variables | MHF | NEMC Mental Health Composite Score | 48.5 |
| 9 | SF-36 General Health Composite Score | GHT | RAND Global Health Composite Score | 46.3 |
| 10 | SF-36 Physical Health Composite Score Variables | PHT | RAND Physical Health Composite Score | 43.6 |
| 11 | SF-36 Mental Health Composite Score Variables | MHT | RAND Mental Health Composite Score | 43.2 |
| 12 | SF-36 Emotional Well Being Score Variables | I24 | SF36 Q24. How much time in the last 4 wks have you been a very nervous person? | 41.5 |
| 13 | SF-36 Health Perception Score Variables | GHPER | General Health Perceptions Score | 37.8 |
| 14 | SF-36 Physical Function Score Variables | PFNC | Physical Functioning Score | 35.9 |
| 15 | SF-36 Emotional Well Being Score Variables | I28 | SF36 Q28. How much time in the last 4 wks did you feel downhearted and blue? | 28.3 |
| 16 | SF-36 Vitality Score Variables | VITAL | Vitality Score | 25.9 |
| 17 | SF-36 Social Function Score Variables | SOFNC | Social Functioning Score | 25.6 |
| 18 | SF-36 Social Function Score Variables | I20 | SF36 Q20. Emotional/physical problems interfere with social activity in the last 4 wks? | 24.1 |
| 19 | SF-36 Vitality Score Variables | I23 | SF36 Q23. How much time in the last 4 wks did you feel full of pep? | 21.9 |
| 20 | SF-36 Vitality Score Variables | I31 | SF36 Q31. How much time in the last 4 wks did you feel tired? | 21.9 |
| 21 | SF-36 Vitality Score Variables | I29 | SF36 Q29. How much time in the last 4 wks did you feel worn out? | 21.5 |
| 22 | SF-36 Emotional Well Being Score Variables | I26 | SF36 Q26. How much time in the last 4 wks have you felt calm/peaceful? | 19.2 |
| 23 | SF-36 Bodily Pain Score Variables | I21 | SF36 Q21. How Much Bodily Pain in the last 4 wks? | 19.1 |
| 24 | SF-36 Health Perception Score Variables | I34 | SF36 Q34. How true?: I am as healthy as anybody I know | 19.0 |
| 25 | SF-36 Health Perception Score Variables | I1 | SF36 Q1. General Health Rating | 17.2 |
| 26 | SF-36 Emotional Well Being Score Variables | I30 | SF36 Q30. How much time in the last 4 wks have you been a happy person? | 17.0 |
| 27 | SF-36 Physical Function Score Variables | I9 | SF36 Q9. Limitation in walking more than 1 mile | 16.8 |

TABLE 6-continued

Predictors (Pred.) 1–58 for CART Analysis of Percentage Excess Weight Loss, Ranked by Variable Importance

| Pred. | Variable Group | Variable | Variable Description | Importance Score |
|---|---|---|---|---|
| 28 | SF-36 Health Perception Score Variables | I36 | SF36 Q36. How true?: My health is Excellent | 16.2 |
| 29 | SF-36 Vitality Score Variables | I27 | SF36 Q27. How much time in the last 4 wks did you have a lot of energy? | 16.1 |
| 30 | SF-36 Bodily Pain Score Variables | PAIN | Bodily Pain Score | 16.1 |
| 31 | SF-36 Health Perception Score Variables | I33 | SF36 Q33. How true?: I get sick a little easier than others | 15.3 |
| 32 | SF-36 Physical Function Score Variables | I10 | SF36 Q10. Limitation in walking several blocks | 14.5 |
| 33 | SF-36 Bodily Pain Score Variables | I22 | SF36 Q22. Did pain the last 4 wks interfere with work? | 14.3 |
| 34 | SF-36 Health Perception Score Variables | I35 | SF36 Q35. How true?: I expect my health to get worse | 13.6 |
| 35 | SF-36 Emotional Well Being Score Variables | I25 | SF36 Q25. How much time in the last 4 wks have you felt so down in the dumps . . .? | 13.1 |
| 36 | SF-36 Social Function Score Variables | I32 | SF36 Q32. Emotional/physical problems interfere with social activities? | 11.6 |
| 37 | SF-36 Bodily Pain Score Variables | PAIN1 | Bodily Pain Severity from SF36 Item 21, NEMC Scoring | 10.6 |
| 38 | SF-36 Health Perception Score Variables | I2 | SF36 Q2. Health now compared to 1 yr ago | 10.2 |
| 39 | SF-36 Bodily Pain Score Variables | PAIN2 | Bodily Pain interference from SF36 Item 22, NEMC Scoring | 10.0 |
| 40 | SF-36 Physical Role Limitation Score Variables | PLIM | Physical Role Limitations Score | 9.4 |
| 41 | SF-36 Physical Function Score Variables | I12 | SF36 Q12. Limitation in Bathing, Dressing | 9.3 |
| 42 | SF-36 Physical Function Score Variables | I6 | SF36 Q6. Limitation in Climbing Several Flights of Stairs | 8.9 |
| 43 | SF-36 Physical Function Score Variables | I5 | SF36 Q5. Limitation in Lifting Groceries | 8.9 |
| 44 | SF-36 Physical Function Score Variables | I4 | SF36 Q4. Limitation in Moderate Activity | 8.8 |
| 45 | SF-36 Physical Function Score Variables | I11 | SF36 Q11. Limitation in Walking One Block | 8.4 |
| 46 | SF-36 Physical Function Score Variables | I8 | SF36 Q8. Limitation in Bending, Kneeling | 7.9 |
| 47 | SF-36 Emotional Role Limitation Score Variables | I19 | SF36 Q19. Did emotional problems in the last 4 wks cause you to work less carefully? | 7.4 |
| 48 | SF-36 Physical Function Score Variables | I7 | SF36 Q7. Limitation in Climbing One Flight of Stairs | 7.4 |
| 49 | SF-36 Physical Function Score Variables | I3 | SF36 Q3. Limitation in Vigorous Activity | 7.0 |
| 50 | SF-36 Health Perception Score Variables | GHQ1 | Global Health Rating from SF36 Item 1, NEMC Scoring | 6.9 |
| 51 | SF-36 Emotional Role Limitation Score Variables | EMLIM | SF36 Emotional Role Limitation Score | 6.2 |
| 52 | SF-36 Physical Role Limitation Score Variables | I16 | SF36 Q16. Did physical problems in the last 4 wks cause difficulty in work/activities? | 4.9 |

TABLE 6-continued

Predictors (Pred.) 1–58 for CART Analysis of Percentage Excess Weight Loss, Ranked by Variable Importance

| Pred. | Variable Group | Variable | Variable Description | Importance Score |
|---|---|---|---|---|
| 53 | SF-36 Physical Role Limitation Score Variables | I13 | SF36 Q13. Did physical problems in the last 4 wks cut down work/activities? | 4.7 |
| 54 | SF-36 Physical Role Limitation Score Variables | I15 | SF36 Q15. Did physical problems in the last 4 wks limit kind of work/activities? | 4.6 |
| 55 | SF-36 Emotional Role Limitation Score Variables | I17 | SF36 Q17. Did emotional problems in the last 4 wks cut down work/activities? | 4.0 |
| 56 | SF-36 Emotional Role Limitation Score Variables | I18 | SF36 Q18. Did emotional problems in the last 4 wks limit accomplishment? | 3.4 |
| 57 | SF-36 Physical Role Limitation Score Variables | I14 | SF36 Q14. Did physical problems in the last 4 wks limit accomplishment? | 3.0 |
| 58 | Patient Gender | MALE | Male Gender Indicator | 2.6 |

Table Notes: Variables ranked by CART relative importance scores, which are measures of the amount of variation in percentage excess weight change that can be accounted for by individual predictors. A score of 10, for example, indicates that a variable can predict one tenth as much variation in weight change as the most important variable, which receives as score of 100. Importance scores are calculated for each of 250 boosted CART regression trees as described by Breiman et al. (1984), referenced herein, and then averaged across trees. Averaged scores are re-normalized by dividing by the highest average score and multiplying by 100. Note that importance scores are measures of predictive "potential" rather than "actual" contribution to prediction. Important predictors that are highly correlated will have similarly high important scores even if some of these predictors are seldom or never used for splitting in the boosted CART trees.

Though useful for identifying key predictors, CART importance scores do not tell anything about the direction of the correlation between a predictor and the target variable, nor do they provide readily interpretable measures of the magnitude of the association. The second component of the analysis is thus to use a logistic regression model as a device for describing the direction and magnitude of the relationship between key predictors and the likelihood of a patient being selected by the screening algorithm.

Using the pooled implantable gastric stimulation trial sample, a logistic regression was estimated of that probability that a patient is selected for treatment by the screening algorithm. The dependent variable in this regression is a binary indicator of whether a patient is selected by the screen, while the regressors are drawn from a list of key predictors identified by the importance score analysis. The estimated model is then used to construct adjusted probabilities of being selected by the screen for patients categorized according to the levels of a particular predictor. The adjustment uses the estimated logistic model to illustrate the effects of variations in a predictor on the likelihood of selection while holding the levels of other key predictors constant. While easier to interpret than regression coefficients, these adjusted probabilities are more consistent with the multivariate nature of the CART prediction model than a simple, bivariate analysis based on unadjusted relative frequencies. Details on the specification of the estimated logistic model and the construction of the adjusted probabilities are provided below.

2. Descriptive Logistic Regression Model

This subsection describes the specification and estimation of the logistic regression model used for summarizing the relationships between the key predictors of excess weight loss in the CART analysis and the likelihood of selection by the CART-based screening algorithm. It also provides a formal definition of the adjusted selection probabilities constructed from the logistic model estimates and displayed in FIGS. 24–30.

Specifying the Model. A major limitation of CART importance scores is that they measure predictive potential rather than actual contribution to prediction. This means that highly intercorrelated predictors will have similarly high important scores, even if some of these predictors are seldom or never used for splitting in the boosted CART trees. This feature makes it inadvisable to specify the descriptive logistic model by simply adding variables to the regression in descending order of their importance scores. Such a strategy would lead to a model focused too narrowly on a set of redundant and highly collinear predictors. To avoid this problem, the 58 predictors are divided into 14 categories of related variables, and then the regressors for the descriptive logistic model are drawn from a list of the 14 variables having the highest importance score within each category.

The 14 predictor categories include age, gender, baseline obesity measures, the eight SF-36 health domains (i.e., physical function, physical role limitations, vitality, bodily pain, general health perception, emotional well being, emotional role limitations, social functioning), and the three SF-36 composite scores (physical, mental and general health). The age, gender and general health composite score categories contain only one variable each. The physical and mental health composite score categories each contain two variables, corresponding to the RAND and NEMC versions of these scores. The SF-36 health domain categories each contain the corresponding domain score and all of the individual item variables contributing to the score.

Table 7 lists the predictors having the highest relative importance score within each of the 14 categories. The basic strategy used to move from this list to a descriptive logistic specification was to enter each listed variable, or a transformation of the variable, into the regression model in descending order of their CART relative importance scores. Transformations were considered because there is nothing in the nonparametric CART analysis to warrant automatically assuming a linear relationship between key predictors and the log-odds of selection by screening, though in some cases such a specification appears adequate. To guide the specification for individual predictors, plots of their mean values were used within quantiles against the log-odds of selection in patient groups defined by the same predictor quantiles. Variables from the list in Table 7 were omitted that were likely to be redundant, given that the specified model already included a highly correlated predictor with a higher relative importance score, or a transformation of such a predictor.

TABLE 7

List of CART Predictors with Highest Importance Scores

| Predictor Group | Variable in Group Having the Highest Importance Score | Importance Score |
| --- | --- | --- |
| 1. Baseline Obesity Measures | Implant BMI (kg/m$^2$) | 100.0 |
| 2. Patient Age | Age at Implant | 65.2 |
| 3. SF-36 Emotional Well Being | Emotional Well Being Score | 52.9 |
| 4. SF-36 Physical Health Composite Score | NEMC Physical Health Composite Score | 52.8 |
| 5. SF-36 Mental Health Composite Score | NEMC Mental Health Composite Score | 48.5 |
| 6. SF-36 General Health Composite Score | RAND Global Health Composite Score | 46.3 |
| 7. SF-36 Health Perception | General Health Perceptions Score | 37.8 |
| 8. SF-36 Physical Function | Physical Function Score | 35.9 |
| 9. SF-36 Vitality | Vitality Score | 25.9 |
| 10. SF-36 Social Function | Social Function Score | 25.6 |
| 11. SF-36 Bodily Pain | SF-36 Item 21 Score | 19.1 |
| 12. SF-36 Physical Role Limitations | Physical Role Limitations Score | 9.4 |
| 13. SF-36 Emotional Role Limitations | SF-36 Item19 Score | 7.4 |
| 14. Patient Gender | Male Gender Indicator | 2.6 |

Table Notes: Variables ranked by CART relative importance scores, which are measures of the amount of variation in percentage excess weight change that can be accounted for by individual predictors. A score of 10, for example, indicates that a variable can predict one tenth as much variation in weight change as the most important variable, which receives as score of 100. Importance scores are calculated for each of 250 boosted CART regression trees as described by Breiman et al. (1984), referenced above, and then averaged across trees. Averaged scores are re-normalized by dividing by the highest average score and multiplying by 100.

As might be expected from their relatively low importance scores, inclusion or omission of predictors listed in the bottom third of Table 7, despite experimentation with a variety of plausible transformations, had little impact on the estimated model. Estimated effects associated with these variables were uniformly small and never reached nominal statistical significance. Thus, they were omitted from the final specification.

One variable not listed in Table 7, i.e., the score for SF-36 Item 33, was added to the model purely because of its similarity to items on locus of control instruments that have been found to be predictive of weight loss and related behaviors.

Figure 35:
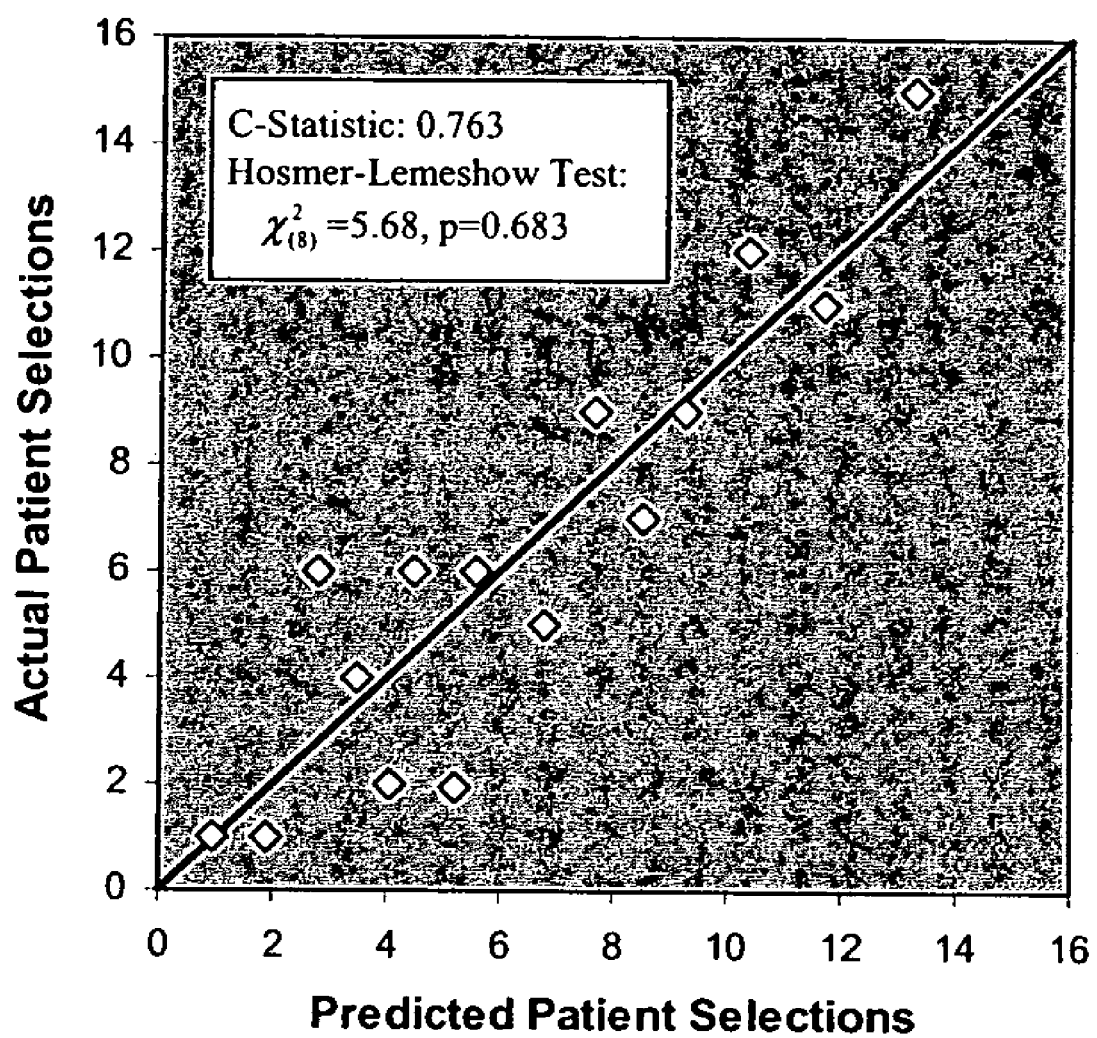
FIG. 35 is a goodness-of-fit plot for a logistic model used to predict patient selection by boosted CART screening.

Model Estimates. Parameter estimates for the descriptive logistic model are shown in Table 8. The asymptotic t-ratios and p-values shown in the table are for the two-sided test of the null hypothesis that the corresponding regression parameter is zero. A Hosmer-Lemeshow goodness-of-fit statistic ($\chi_{(8)}^2$=5.68, p=0.683) suggests that the model provides a reasonable fit to the data, as does the plot in FIG. 35 of actual versus predicted selections within quantiles of the logistic model predicted probabilities. FIG. 35 is a plot constructed by ranking the 252 sample observations by their predicted probabilities of selection under the estimated logistic model and then partitioning the ranked observations into 20 risk groups of approximately equal size. The plotted points correspond to the combination of observed and predicted patient selections in each of the 20 groups. Predicted selections are the sum of the predicted probabilities of selection under the estimated model across subjects in a risk group.

As an additional check on the model specification, a stepwise regression procedure was used to see if any of the other predictors from the CART analysis would enter the model at conventional significance levels. A handful of individual item scores entered the model with inconsequentially small coefficients and minimal change in the parameter estimates for the already included variables. This at least suggests that the importance-score based specification strategy used herein has not led us to missing any glaringly obvious correlates of selection by the screening algorithm (i.e., the predictive model).

It should be kept in mind that the logistic model was used only as a descriptive device for summarizing relationships between key predictors and patient selection. If estimates of a simple parametric model like that in Table 8 could provide sufficiently accurate prediction of selection by the screening algorithm, there would have been no need for resorting to the complexities of the boosted CART regression tree analysis. The CART results could be closely duplicated by screening based on direct prediction of weight loss success with a simple parametric regression. As it is, the amount of variation in patient selection relegated to idiosyncratic error by this simple, descriptive logistic regression is sufficient to make such a model practically useless as a basis for actual screening.

Adjusted Selection Probabilities. The estimated logistic model is used to construct adjusted probabilities of selection by the screening algorithm that are displayed in FIGS. 24–30. To provide a formal definition of these adjusted probabilities the following notation was adopted:

$x_i=(x_{i1}, x_{i2}, \ldots, x_{iK})'$ is a K-vector of covariate values for the $i^{th}$ subject;

$\beta$ is the corresponding vector of logistic regression parameter estimates;

$S_i$ is a binary indicator of selection, such that $S_i=1$ if the $i^{th}$ subject is selected for implantable gastric stimulation treatment by the CART screening algorithm, and $S_i=0$;

$Pr(S_i=1|x_i)=p(x_i)=[1+\exp(x'_i\beta)]^{-1}$ is the $i^{th}$ subject's logistic predicted probability of being selected for implantable gastric stimulation treatment by the CART screening algorithm; and $p(x_{ij}=c)$ is the predicted probability of selection for the $i^{th}$ subject, evaluated with the $j^{th}$ covariate set equal to c while all other covariates remain at their observed values.

The adjusted selection probability given $x_{ij}=c$ is can then be written as $$p(x_j = c) = \frac{1}{N} \sum_i p(x_{ij} = c),$$

which is simply average of $p(x_{ij}=c)$ across all sample observations. The adjusted probability of selection given $x_{ij} \geq c$ can be written as $$p(x_j \geq c) = \frac{1}{N_\Theta} \sum_{c \in \Theta} p(x_j = c),$$

which is the average of $p(x_j=c)$ over the set $\Theta$ of $N_\Theta$ not necessarily unique values of $x_{ij} \geq c$ that occur in the observed sample.

TABLE 8

Logistic Regression Estimates

| Model Covariates | Parameter Estimate | t-ratio | p-value (two sided) |
|---|---|---|---|
| Intercept | 82.607 | 2.61 | 0.0090 |
| Baseline BMI (kg/m$^2$) | −0.053 | −1.91 | 0.0558 |
| Ln(Age at Implant) | −45.833 | −2.60 | 0.0093 |
| ln(Age at Implant)$^2$ | 6.389 | 2.61 | 0.0089 |
| SF-36 Emotional Well Being Score | −0.027 | −2.55 | 0.0109 |
| I$_+$(SF-36 Physical Health Composite Score $\geq$45) | 0.815 | 2.25 | 0.0245 |
| I$_+$(SF-36 General Health Perception Score <30) | 1.637 | 2.65 | 0.0080 |
| I$_+$(SF-36 General Health Perception Score >75) | −1.148 | −2.33 | 0.0197 |
| SF-36 Vitality Score | 0.030 | 3.05 | 0.0023 |
| SF-36 Item 33 Score | 0.017 | 2.51 | 0.0123 |

Table Notes: Dependent variable is a binary indicator for selection by the boosted CART screening model with a 12 percent excess weight loss (% EWL) target. Screened subjects are selected under this criterion if the mean of predicted % EWL across the 250 boosted trees is $\geq$12 or a majority of trees predict % EWL$\geq$12. $I_+(\cdot)$ denotes an indicator function such that $I_+(\cdot)=1$ if the condition in the parentheses is true, and $I_+(\cdot)=0$ otherwise. The reported t-ratios are the ratio of the parameter estimates to their standard errors and have an asymptotically standard normal distribution under the assumed model. The p-values are for two-sided tests of the null hypothesis that the true value of the corresponding logistic model parameter is zero.

Figure 24:
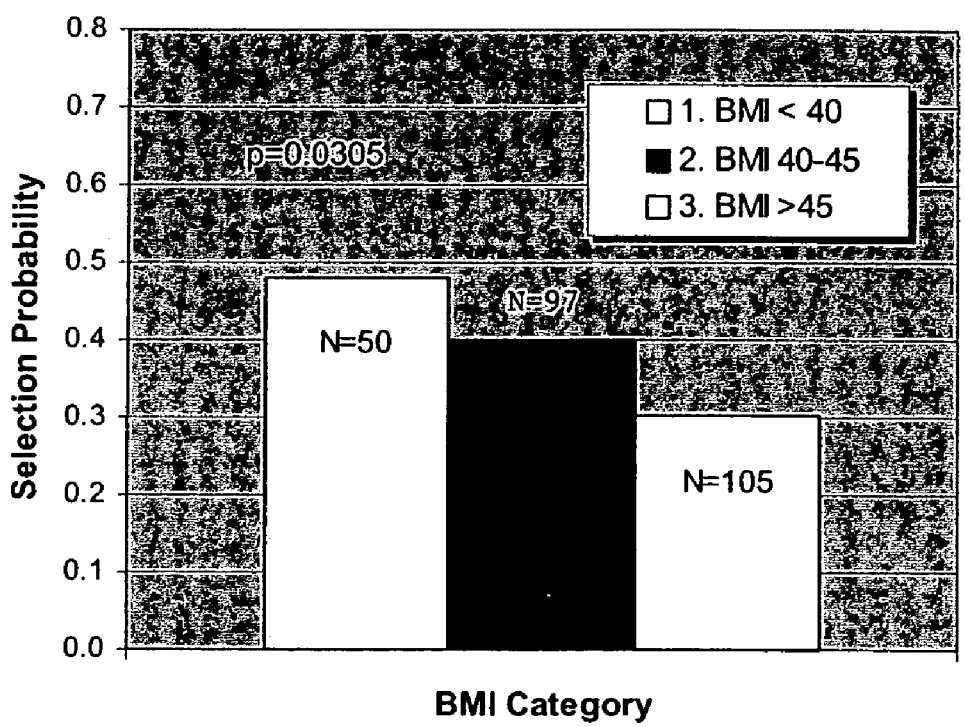
FIG. 24 is a bar graph showing the probability of selection for treatment relative to BMI category by the predictive model developed according to an embodiment of this invention.
Figure 25:
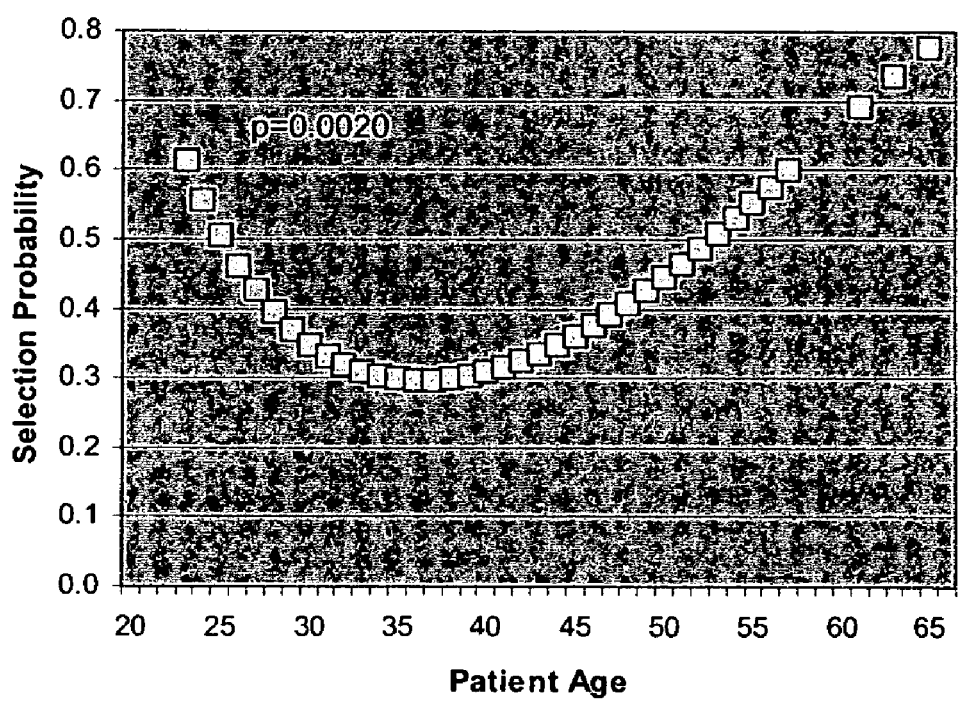
FIG. 25 is a plot showing the probability of selection for treatment relative to patient age by the predictive model developed according to an embodiment of this invention.

The main results of this analysis are displayed in FIGS. 24 and 25. The p-values noted in these figures correspond to Wald tests of the null hypothesis that, under the estimated logistic regression model, the corresponding predictor has no association with selection by the screening algorithm. The p-values can be interpreted as the probability of the observed association occurring by chance when the predictor in question is in fact unrelated to selection. The sample sizes displayed on the bar graphs in FIGS. 24 and 25 indicate the number of implantable gastric stimulation trial subjects having values of the predictor within the ranges indicated in the bar labels.

FIGS. 24 and 25 show that the likelihood of being selected for treatment by the screening algorithm is negatively related to patient BMI and has a J-shaped relationship with patient age, falling at young ages and then rising sharply after age 40. For instance, a patient with BMI less than 40 is more than 1.5 times as likely to be selected for treatment as an otherwise similar patient with a BMI over 45. Similarly, with the values of other key predictors held constant, a 55-year-old patient is nearly twice as likely to be selected for treatment as a 40-year-old patient. Note that the "otherwise similar" and "other key predictors held constant" caveats attached to these comparisons are critical. A 40-year-old patient with a BMI over 45 may nonetheless have a high probability of selection because of favorable observed values of other prognostic factors. Further, the ultimate mix of patients selected for treatment depends critically on the distribution of prognostic factors among patients presenting for treatment. For example, despite the trough in the adjusted selection probability curve over the 30 to 45 year age range, a larger number of the implantable gastric stimulation trial subjects would be selected by screening from this age group than from among subjects younger than 30 or older than 45. This result reflects the predominance of 30 to 45-year-olds among patients seeking obesity treatment and agreeing to participate in an implantable gastric stimulation trial.

Pre-treatment BMI has been found to be predictive of weight loss outcomes in numerous reported obesity treatment studies. The direction of the association, however, is variable across studies, depending at least in part on whether outcomes are measured in relative or absolute terms. Higher BMI is generally found to be predictive of a greater absolute number of kilograms or pounds lost under a given treatment. The likely reason for this is the well-established relationship between body weight and energy expenditure. Persons with higher BMI values have higher average body weight, and, as a result, higher expected energy expenditure. They thus tend to lose more weight on a fixed-calorie, hypoenergetic diet than do lighter persons adhering to the same diet. When the focus is on relative weight loss, however, measuring heavier patients' losses as percentages of their higher initial excess or total weights offsets their energy expenditure advantage. Heavier patients with higher initial BMI values tend to have smaller percentage weight losses, despite losing a greater number of pounds or kilograms. Patient selection under the screening algorithm is based on boosted CART predictions of percentage excess weight loss, a relative outcome measure. The finding that higher BMI is predictive of lower percentage excess weight loss, and, consequently, a lower likelihood of selection by the screening algorithm is thus consistent with the findings of other obesity treatment studies that focus on relative weight loss.

The relationship between age and the probability of selection by the screening algorithm is at least partially consistent with age-related patterns in weight change observed in large US and European cohort studies. These studies find that average body weight among adults initially increases with age, then stabilizes between the ages of 40 and 50, and finally begins to decline markedly thereafter. Mean weight losses at older ages are largest among obese adults, (defined as having BMI>30), and the onset of these losses among the obese occurs at earlier ages than for persons in lower BMI categories. Given this pattern of increasing likelihood of weight loss beyond age 50 in the general population, it is not surprising that age is an important predictor of weight loss success in the CART analysis of implantable gastric stimulation patients, or that the likelihood of selection begins to increase sharply around age 50.

Figure 26:
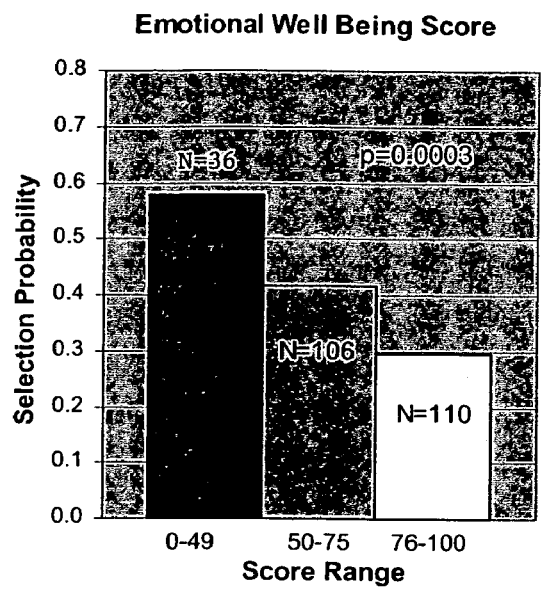
FIGS. 26–29 are bar graphs showing the probability of selection for treatment relative to Baseline SF-36 Scores for Emotional Well Being, General health Perception, Physical Health Composite, and Vitality scores, respectively, by the predictive model developed according to an embodiment of this invention.
Figure 27:
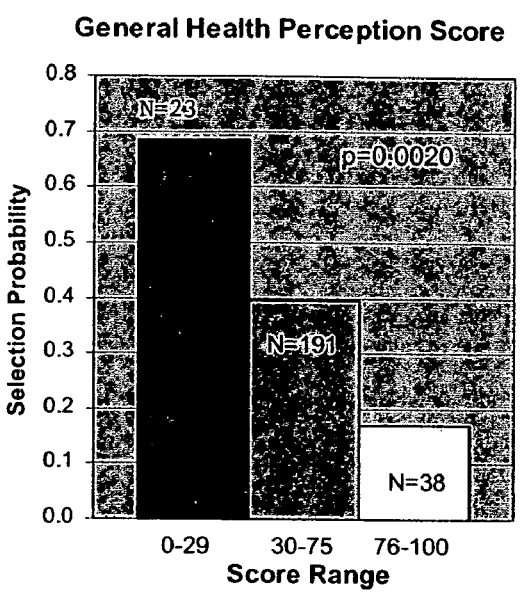

FIGS. 26–29 summarize the primary relationships between selection by the screening algorithm and pre-treatment SF-36 health survey responses. FIGS. 26 and 27 show that the likelihood of selection is negatively related to the SF-36 emotional well-being and general health perception scores. The SF-36 emotional well being score is constructed from items asking about the frequency of depressed mood and emotional distress during the past month. A higher reported frequency of emotional problems translates into a lower emotional well being score. The general health perception score is based on items asking the respondent to rate their overall health in varying ways. The more favorable the ratings the higher the health perception score.

Notably, despite being severely obese, a sizeable minority of implantable gastric stimulation trial patients (110 of 252) have pre-treatment emotional well being scores greater than the average for the general population, and atypically high relative to other obese samples. Such relative emotional contentment is predictive of poorer weight loss outcomes under implantable gastric stimulation and a lower likelihood of selection by screening. This result is consistent with a range studies finding that severely obese individuals with relatively high levels of emotional distress are more likely to pursue obesity treatment, and more likely to pursue intensive modes of treatment that result in greater weight loss. The negative association of patient perceptions of their overall health with selection by screening is also consistent with the existing empirical literature on obesity. In particular, severely obese persons who clearly recognize the health risks of their obesity are more likely to attempt and to succeed in weight loss than comparably obese persons who believe they have no serious health problem.

Figure 28:
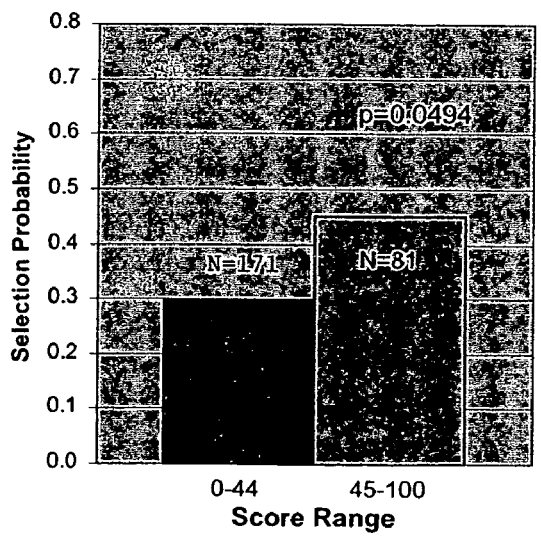
Figure 29:
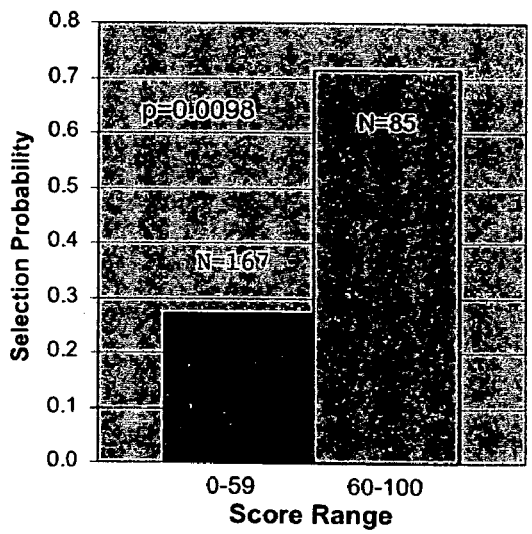

FIGS. 28 and 29 show that patients with higher SF-36 physical health composite and vitality scores are more likely to be selected by the screening algorithm. The physical health composite score primarily reflects patient responses to questions about whether physical problems inhibit them in performing specific tasks, or participating in routine activities. The score is normalized to have a mean of 50 and standard deviation of 10 for the US adult population, with higher scores indicating better physical health. Patients with physical health scores of at least 45 are 1.5 times more likely to be selected for treatment than otherwise comparable subjects with physical health scores less than 45. The chances of selection vary more dramatically with vitality scores, which are constructed from questions about how often the respondent feels either tired or energetic. Higher vitality scores indicate a higher frequency of feeling energetic and lower frequency of fatigue. Holding other key prognostic factors constant, a patient with a vitality score in the 60 to 100 range is nearly three times as likely to be selected for treatment as a patient scoring below 60.

These physical health and vitality score results are also consistent with existing empirical evidence on obesity treatment outcomes. It is well established that higher levels of physical activity are predictive of better weight loss and weight loss maintenance under obesity treatment, and reduced risk of obesity in the general population. Patients who are free from major physical impairments and relatively energetic are more likely to be physically active, making these traits understandable predictors of weight loss success. Notably, the only published study of which the present investigators are aware of that explores the prognostic value of the SF-36 for bariatric surgery outcomes also finds a statistically significant, positive association between weight loss and pre-treatment physical health composite scores. I.e., Dixon et al., Pre-operative predictors of weight loss at 1-year after LapBand surgery, Obes. Surg. 2001, 11(2): 200–7.

Item 33 on the SF-36 questionnaire asks respondents to endorse or reject the following statement: "I seem to get sick a little easier than others". The wording of this statement is similar to items appearing on various "locus of control" scales that have been found to be predictive of weight loss treatment outcomes and weight-related behaviors. Because of this similarity, we included the Item 33 score in the logistic regression used to describe the relationship between key predictors of weight loss in the CART analysis and the likelihood of selection by the screening algorithm. The Item 33 score turns out to be a statistically significant predictor of selection in the estimated model, and the direction of the relationship is consistent with the locus of control literature. Studies in the literature consistently find that persons with an external locus of control, who see health events or weight gain as things that "just happen" to them, are more likely to fail in weight loss treatment, more likely to engage in eating behaviors that increase their risk of obesity, and more likely to be unresponsive to diet-related health education materials. The opposite holds for persons with an internal locus of control, who see themselves as responsible for and able to contribute to their own health.

Locus of control instruments distinguish internal and external control orientations by asking respondents to endorse or reject statements that assert varying degrees of individual control over personal health. The reason why SF-36 Item 33 can plausibly be viewed as a locus of control measure can be seen by comparing it to items on the Health Locus of Control (HLC) instrument developed by Wallston and colleagues. E.g., Wallston B. S., et al., Development and Validation of the Health Locus of Control (HLC) Scale, J. Cons. Clin. Psy., 1976, 44:580–85. Strong endorsement of "I seem to get sick a little easier than others," is similar to rejecting the following internal locus of control items on the HLC:

"1. If I take care of myself, I can avoid illness."

"2. Whenever I get sick it is because of something I've done or not done."

Likewise, strong endorsement of Item 33 is similar to endorsing one of the following external locus of control items from the HLC:

"3. Good health is largely a matter of good fortune."

"4. No matter what I do, if I am going to get sick I will get sick."

Figure 30:
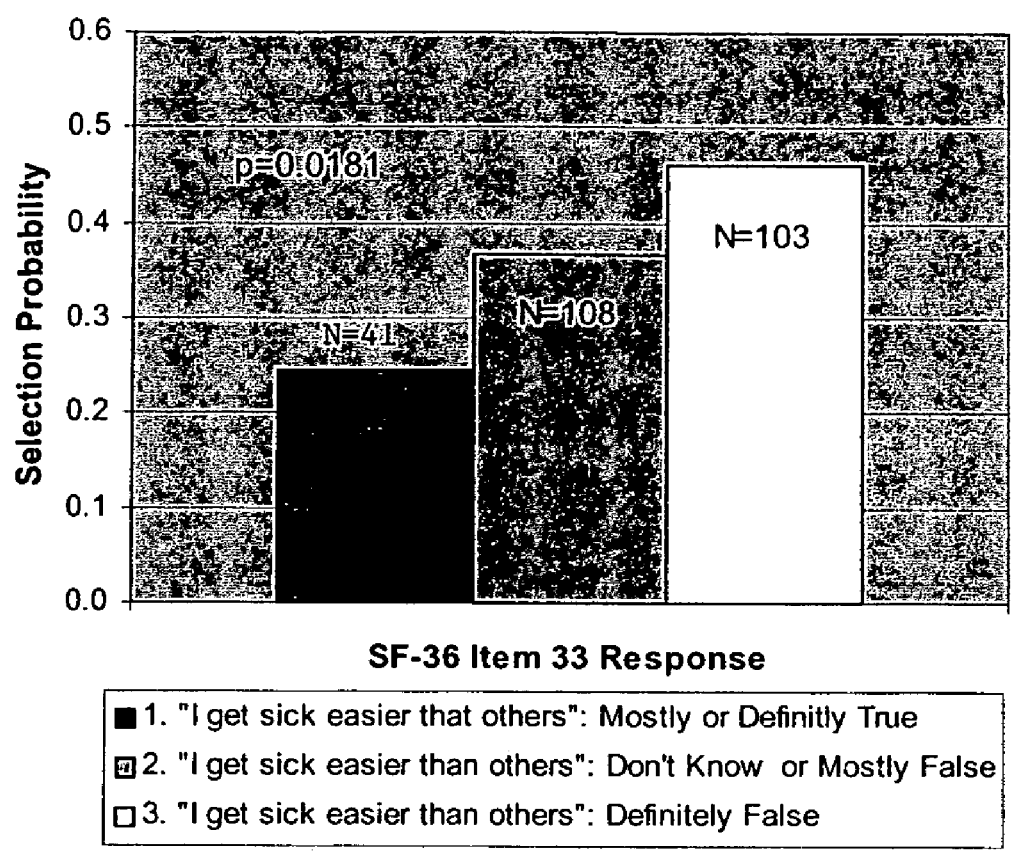
FIG. 30 is a bar graph showing the probability of selection for treatment relative to Baseline SF-36 Item 33 Responses by the predictive model developed according to an embodiment of this invention.

Given these similarities it is plausible to view strong endorsement of Item 33 on the SF-36 as an indication of an external locus of control orientation. Such endorsement is thus expected to be predictive of poorer implantable gastric stimulation weight loss outcomes and a lower probability of selection for treatment. Conversely, strong rejection of Item 33 would be consistent with an internal locus of control orientation, and ought to be associated with better weight loss and a higher chance of retention by screening. As shown in FIG. 30, this is precisely the pattern that was found in the descriptive logistic regression analysis. This provides another point of consistency between the screening algorithm and the existing empirical literature on obesity.

F. Treatment and Selection Effects

The foregoing exemplary analysis shows that the CART-based screening algorithm selects patients based on characteristics that have been found to be predictive of weight loss and weight maintenance in a wide range of other empirical studies of obesity. Evidence for the presence of a significant implantable gastric stimulation treatment effect in patients selected by the screening algorithm can also be gleaned from the data already in hand.

Figure 31:
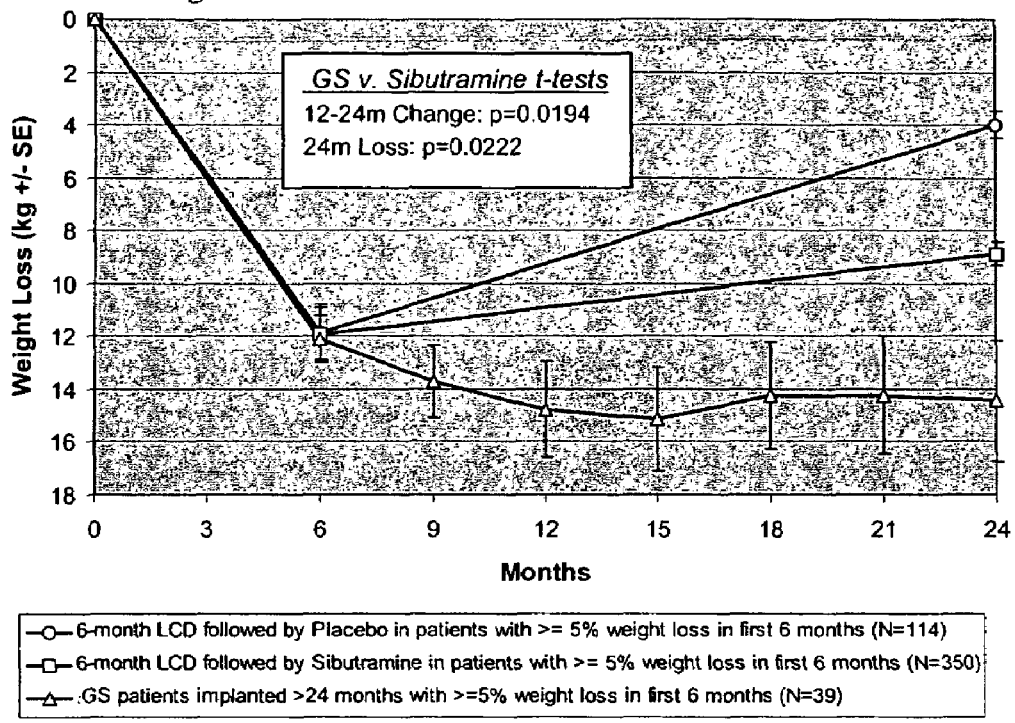
FIG. 31 is a plot showing weight loss maintenance under implantable gastric stimulation for patient data inputted into the predictive model developed according to an embodiment of this invention versus that of a reported obesity therapy study using sibutramine.
Figure 32:
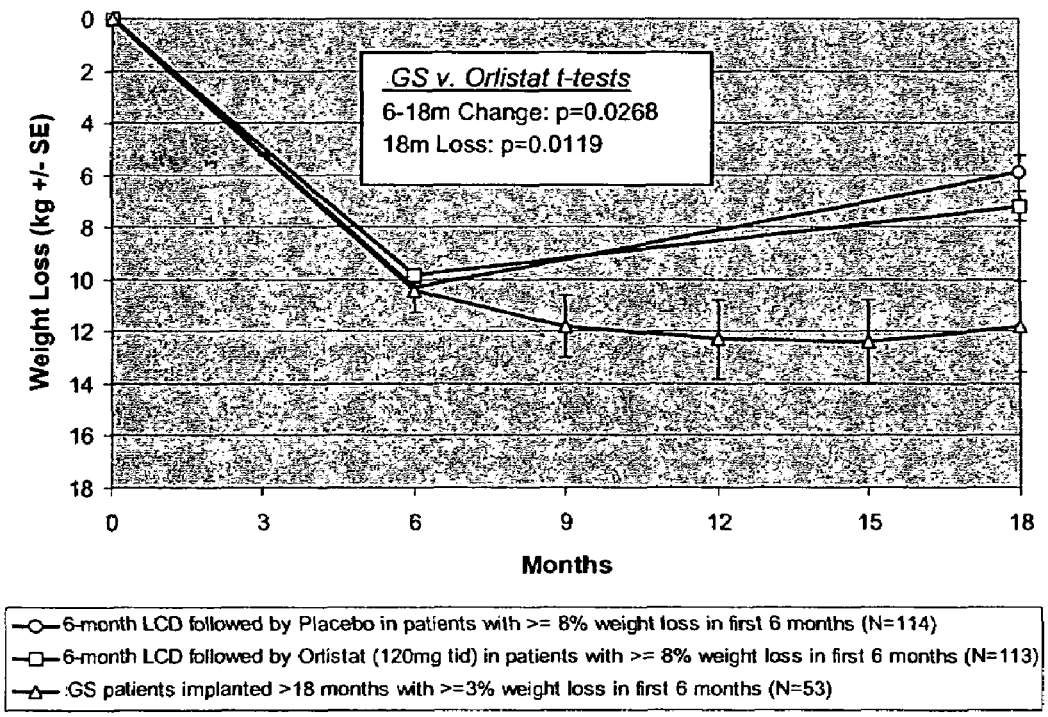
FIG. 32 is a plot showing weight loss maintenance under implantable gastric stimulation for patient data inputted into the predictive model developed according to an embodiment of this invention versus that of a reported obesity therapy study using orlistat.
Figure 33:
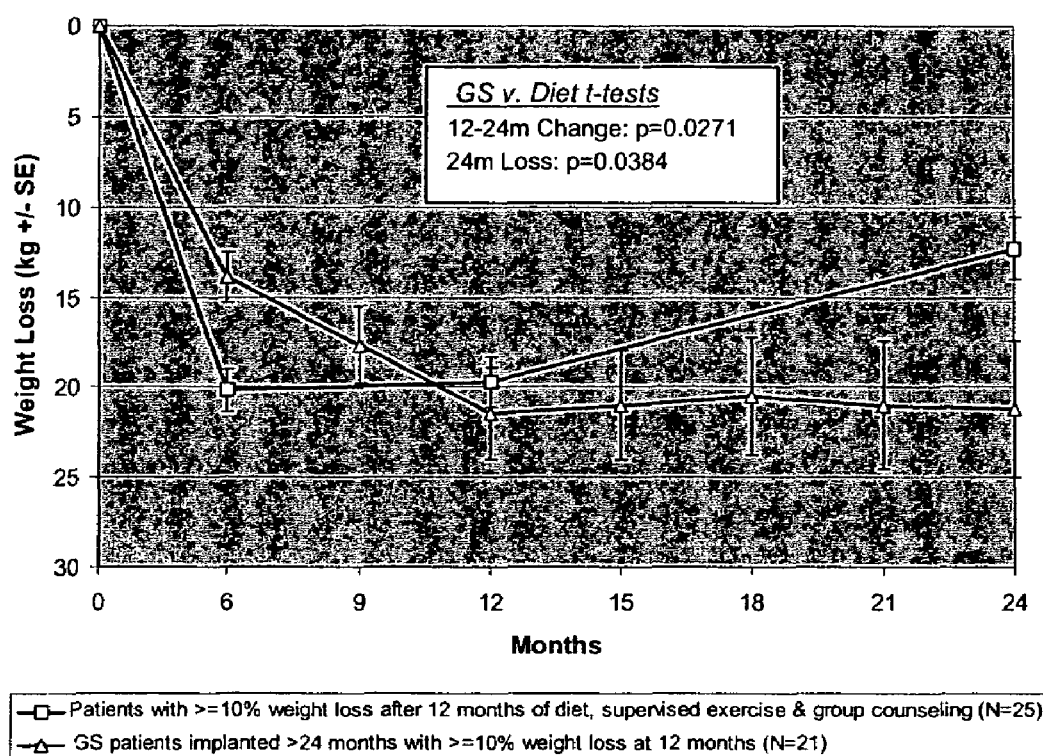
FIG. 33 is a plot showing weight loss maintenance after a year of diet and counseling as compared to implantable gastric stimulation treatment.

One source of such evidence lies in comparisons of weight loss maintenance in implantable gastric stimulation patients selected based on achieving an interim weight loss target, (e.g., 5 percent weight loss in 6 months, 10 percent in 12 months), to weight loss maintenance in studies of established treatments that selected their subjects in the similar fashion. Three comparisons of this type are shown in FIGS. 31–33. In all three cases, samples of implantable gastric stimulation trial patients chosen based on interim weight loss maintain their losses significantly better than similarly selected samples of obese patients treated with standard therapies. This result is relevant to the question of whether there is a device effect for implantable gastric stimulation patients selected by the screening algorithm because of the near equivalence of selection by screening and selection based on initial weight loss. The two methods of selection pick sets of implantable gastric stimulation patients with a large degree of overlap, and nearly identical weight loss outcomes. If there is an implantable gastric stimulation treatment effect for patients selected on initial weight loss, as the comparisons in FIGS. 31–33 suggest, then there is also a treatment effect among patients selected by screening, since the two sets contain largely the same patients.

FIG. 31 compares weight loss in long-term implantable gastric stimulation subjects to results from a large randomized, placebo controlled trial of sibutramine for weight loss maintenance. Viz., James, W. P. et al, Effect of sibutramine on weight maintenance after weight loss: a randomised trial. STORM Study Group. Sibutramine Trial of Obesity Reduction and Maintenance. Lancet 2000, 356(9248):2119–25. Subjects included in the sibutramine trial had to lose at least 5 percent of their body weight during a 6 month hypoenergetic diet with twice-monthly dietary counseling. Those who succeeded were then randomized to either sibutramine or placebo, and followed for an additional 18 months, during which they continued to receive monthly dietary counseling. The sibutramine trial patients were then compared to implantable gastric stimulation patients who also lost at least 5 percent of their body weight during their first 6 months of treatment, and who have been implanted at least 24 months, the length of the sibutramine trial. All such patients are from the first generation of European and US implantable gastric stimulation trials in which the treatment protocols did not include any dietary or behavioral adjunct to implantable gastric stimulation. In both the implantable gastric stimulation and sibutramine trial samples, missing weight loss follow-up data were imputed by carrying forward the last available observation. Despite the fact that the long-term implantable gastric stimulation patients received no dietary or behavioral counseling, their weight losses were better maintained from 6 through 24 months than the sibutramine treated patients (p=0.0194), and they had a larger mean weight loss at 24 months (p=0.0222).

FIG. 32 shows an analogous comparison between long-term implantable gastric stimulation patients and subjects in a large randomized trial of orlistat for weight loss maintenance. Viz., Hill, J. O., et al., Orlistat, a lipase inhibitor, for weight maintenance after conventional dieting: a 1-y study, Am J Clin Nutr, 1999, 69(6): 1108–16. Inclusion in the orlistat trial required that subjects lose at least 8 percent of their pre-treatment body weight during a 6 month hypoenergetic diet that included dietary and behavioral counseling. Patients attaining the weight loss goal were then randomized to either placebo or one of three dosages of orlistat treatment plus continued dietary counseling for an additional year. Only the highest orlistat dosage (120 mg tid) showed any evidence of efficacy over placebo in the trial, and it is these results that are displayed in FIG. 32. The implantable gastric stimulation comparison groups consists of patients implanted at least 18 months (the length of the orlistat trial) who lost at least 3 percent of their body weight during the first 6 months of treatment. Note that in this case a weaker interim weight loss criteria has been used to select the implantable gastric stimulation patients in order to yield a group with mean weight loss roughly equal to that of the orlistat subjects at 6 months; implantable gastric stimulation trial patients losing 8 percent or more of their body weight in 6 months have substantially larger weight losses. Statistics for both the implantable gastric stimulation and orlistat trial samples were calculated with missing weight loss follow-up data imputed by carrying forward the last available observation. Again, despite the fact that the long-term implantable gastric stimulation patients received no dietary or behavioral counseling, their weight losses were better maintained from 6 through 18 months than the orlistat treated patients (p=0.0268), and they had a larger mean loss at 18 months (p=0.0119).

Figure 34:
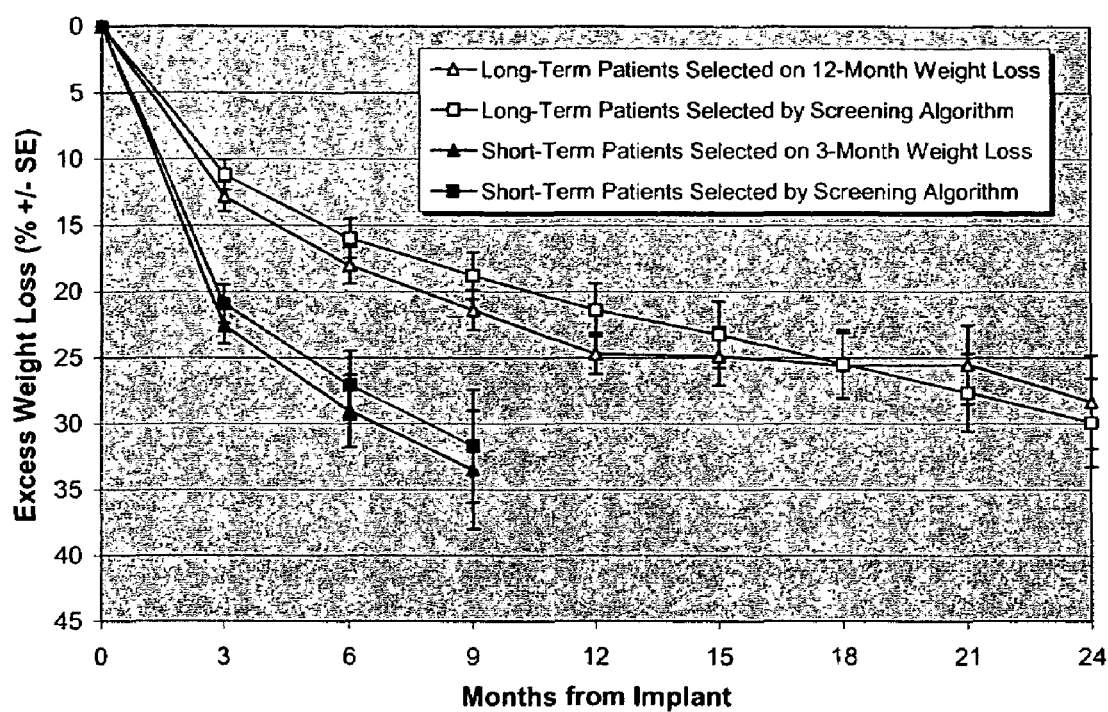
FIG. 34 is a plot showing outcomes in screened patients and patients selected on initial weight loss.

FIG. 34 compares weight loss maintenance in implantable gastric stimulation subjects to that observed in 25 women who completed a yearlong diet and behavioral support program as part of a randomized trial of supervised exercise treatment. Viz., Wadden, T. A., et al., Two-year changes in lipids and lipoproteins associated with the maintenance of a 5% to 10% reduction in initial weight: some findings and some questions. Obes Res, 1999, 7(2): 170–8. All trial participants attended weekly group counseling sessions for 48 weeks and three-quarters were assigned to a year of supervised aerobics, strength training, or a combination of the two. Weight loss outcomes were followed for an additional year after the end of the diet and exercise program. The 25 patients were selected from 77 original trial subjects because they maintained at least a 5 percent weight loss through 100 weeks, and had sufficiently high baseline blood cholesterol to qualify for a sub-study of the effects of maintained weight loss on blood levels of lipids and lipoproteins. All but one of these 25 patients had lost more than 10 percent of her initial weight at the end of the 48-week treatment period. Thus their weight loss maintenance was compared over the subsequent year to implantable gastric stimulation subjects who lost more than 10 percent of their body weight in 12 months of treatment, and who have been implanted at least 24 months, approximating the length of the comparison study. Missing weight loss follow-up data for the implantable gastric stimulation patients were again imputed by last observation carry forward. Because of the fashion in which they were selected, there are no missing follow-up data for the 25 women from the diet and exercise study. Weight loss maintenance is again evidently superior under implantable gastric stimulation therapy. The implantable gastric stimulation subjects experience significantly less weight regain than the comparison group from 12 to 24 months (p=0.0271), and have a larger absolute weight loss at 24 months (p=0.0384).

These comparisons of weight loss maintenance under implantable gastric stimulation and other treatments may not rise to the level of evidence that would be offered by head-to-head comparisons in randomized clinical trials. Still, they have notable features that make it difficult to readily explain the superior weight loss maintenance observed in implantable gastric stimulation subjects as anything other than an implantable gastric stimulation treatment effect. First, the implantable gastric stimulation and comparison treatment samples demonstrate ostensibly similar weight loss motivation by surpassing comparable interim weight loss thresholds, and losing nearly identical amounts of weight prior to the maintenance periods that are the focus of the comparisons. Second, the fact that long-term implantable gastric stimulation subjects used in these comparisons received no treatment other than the implantable gastric stimulation implant makes it impossible to attribute their superior weight loss maintenance to an adjunctive therapy. Thirdly, the comparison studies were picked because of their focus on maintenance after attainment of a given weight loss threshold, and not because they had a typically unfavorable weight loss outcomes. Indeed, the patterns of weight loss and regain in the comparison studies are similar, if not more favorable, than those reported in other studies of the same treatments.

If there is an implantable gastric stimulation treatment effect for implanted patients selected based on interim weight loss, then there is reason to expect a similar effect among implantable gastric stimulation patients selected by the screening algorithm. The reason for this is that the two sets of patients are largely the same. For instance, 72 percent of long-term implantable gastric stimulation patients selected for the sibutramine comparison based on having at least a 5 percent weight loss at 6 months are also selected by the screening algorithm using the 12 percent excess weight loss target. Similarly, 85 percent of the long-term implantable gastric stimulation patients selected for the comparison in FIG. 33 based on their 12-month weight loss are also selected by the screening algorithm under the 12 percent predicted excess weight loss cutoff. The excess weight loss outcomes plotted in FIG. 34 provide further evidence of the similarity of implantable gastric stimulation patients selected by the screening algorithm to those selected based on interim weight loss.

EXAMPLE 2

Performance of Predictive Model on New Patients

The performance of the CART predictive screening algorithm described in Example 1 was evaluated on new patients, i.e., patients who were not among the subjects used in development and validation of the predictive model. These included seventeen patients (N=17) implanted after the development of the CART predictive screening model described in Example 1, as well as seven patients (N=7) for whom baseline and follow-up data were only obtained from clinical study sites after the development of the predictive model. Two additional new subjects having ages less than 25 and BMI's greater than 45 were excluded from the analysis given the unusual combination of youth and very severe obesity. Less than 1% of subjects in the 252 patient development sample had this combination of youth and very severe obesity, and the screen is not expected to perform well in this subpopulation until further data are acquired on similar subjects.

The CART predictive screening model was applied using baseline data obtained from the 24 new patients. These new patients were severely obese (BMI>35), and all were 25 to 65 years old.

Subjects for which the CART predictive screening model predicted eventual attainment of weight loss equal to at least 15% of baseline excess body weight were deemed to have "passed," while those subjects who did not meet this criterion were deemed to have "failed" the screening model. 13 of the patients "passed" screening by the CART predictive screening model, and 11 patients "failed."

Each of the 24 patients received an implantable gastric stimulation implant, whether they "passed" or "failed." Apparatus for stimulating neuromuscular tissue of the gastrointestinal tract and methods for installing the apparatus to the neuromuscular tissue and therapeutic techniques for operating the apparatus as applied to these new patients are similar to that indicated in above Example 1. The original weight of each patient was recorded, and each patient's baseline excess body weight was determined.

A follow-up weight measurement for each of the 24 patients were taken at an average of 10.5 months after implantation. Regarding the timing of the follow-up measurements for weight loss taken on the patients, the means and ranges thereof (in months) are indicated in Table 9. In Table 9, "Previously Implanted" patients were implanted with gastric stimulators prior to the development of the screening algorithm, but their follow-up data did not become available until after the predictive model was developed. "Newly Implanted" patients were implanted with gastric stimulators after the predictive model was developed. Neither group patients contributed to the sample used to develop the predictive model.

TABLE 9

Follow-Up Weight Loss Measurement Timing

| Group | All Patients in Group | Previously Implanted | Newly Implanted |
|---|---|---|---|
| Passed Screen Group | N = 13 Mean: 10 Months Range: 3 to 23 Months | N = 4 Mean: 17 Months Range: 12 to 23 Months | N = 9 Mean = 7 Months Range: 3 to 12 Months |
| Failed Screen Group | N = 11 Mean: 11 Months Range: 5 to 19 Months | N = 3 Mean = 14 Months Range: 12 to 19 Months | N = 8 Mean = 10 Months Range: 5 to 15 Months |
| Both Groups Combined | N = 24 Mean: 10 Months Range: 3 to 23 Months | N = 7 Mean: 15 Months Range: 12 to 23 Months | N = 17 Mean: 8 Months Range: 3 to 15 Months |

Figure 36:
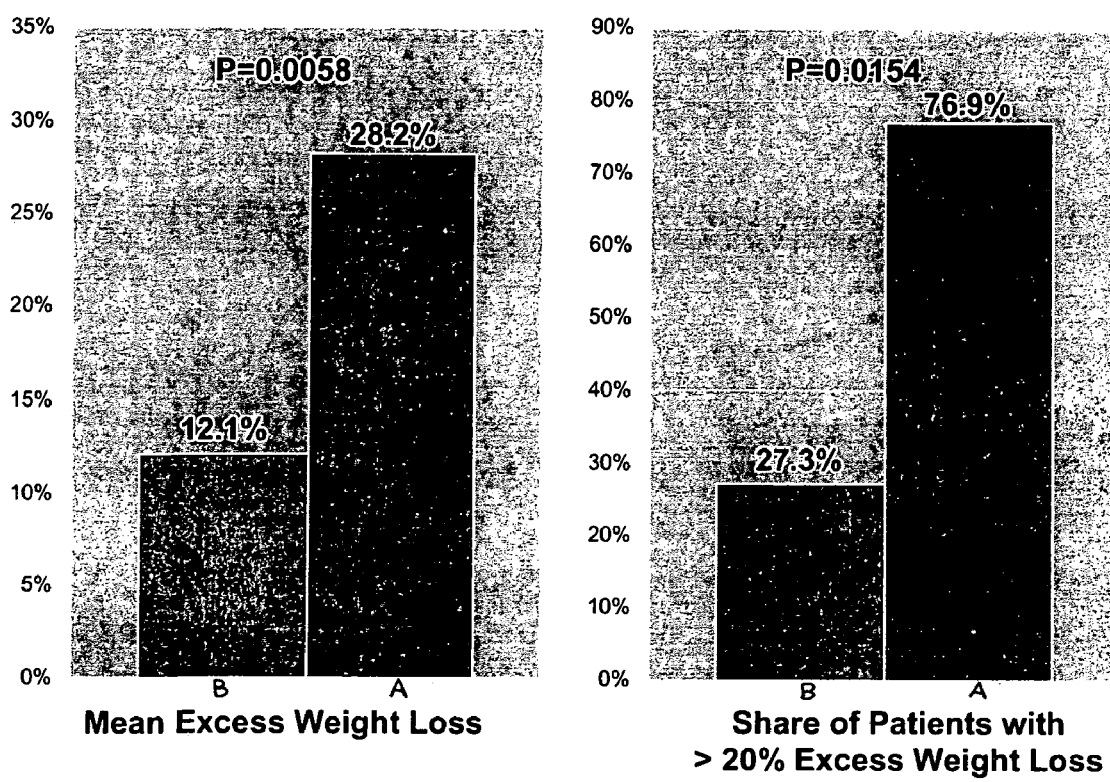
FIG. 36 is a bar graph showing the results of a clinical study in terms of the mean and excess weight losses and share of patients losing at last 20% of their initial excess body weight in respective "passed screen" and "failed screen" groups of severely obese patients, observed at an average of 10.5 months after receiving an implantable gastric stimulation implant, in which a predictive model developed according to an embodiment of this invention was used to screen and designate these patients either prior to implantation (17 patients), or in which this predictive model was applied to screen and designate previously implanted patients for whom weight loss follow-up data were unavailable at the time the predictive model was developed.

Mean weight loss in each test group, and the share of patients in each group losing at least 20% of their excess body weight were determined, and these results have been plotted as bar graphs in FIG. 36. P-values indicated in FIG. 36 are from two-sample t-tests for differences between the means for the "failed screen" and "passed screen" groups.

As shown in FIG. 36, the 13 patients who "passed" screening by the CART predictive screening model had a mean excess body weight loss of 28% as compared to a mean excess body weight loss of 12% for the patients who had failed the CART predictive screening model. In addition, 77% of the patients in the "passed screen" group lost at least 20% of their baseline excess body weight, while only 27% of patients in the "failed screen" group lost 20% or more of their baseline excess body weight. These clinical results demonstrate the predictive reliability of the CART predictive screening model which was used.

While the present invention has been exemplified above in the context of screening patients for implantable gastric stimulation therapy to treat obesity, it will be appreciated that the invention has broader application in screening patients for various obesity therapies and treatments, which are not limited to implantable gastric stimulation. It also may be used before, during, or after an animal clinical trial to demonstrate safety or efficacy of a medicinal therapy or medical device. For instance, the screening method embodied herein may be applied to human clinical trials directed, e.g., to overweight therapy, metabolic therapy, obesity therapy, and/or their related comorbidities. The related comorbidities associated with obesity include, for example, high blood pressure, hypertension, high blood cholesterol, dyslipidemia, Type 2 (non-insulin dependent) diabetes, insulin resistance, glucose intolerance, hyperinsulinemia, coronary heart disease, angina pectoris, congestive heart failure, stroke, gallstones, cholesystitis, cholelithiasis, gastroephageal reflux disease (GERD), gout, osteoarthritis, respiratory problems such as obstructive sleep apnea and sleep apnea complications of pregnancy, cancer (e.g., endometrial, breast, prostate, and colon cancers), poor female reproductive health (e.g., menstrual irregularities, infertility, irregular ovulation), bladder control problems (e.g., stress incontinence), uric acid nephrolithiasis, psychological disorders (e.g., depression, eating disorders, distorted body image, and low self esteem). In general, any treatment for obesity revolves around one basic item: less consumption of food. Even gastric bypass surgery, a radical and permanent change to the gastro-intestinal tract, can fail if a patient is not committed to a drastic lifestyle change primarily oriented to consume less food. The specific non-limiting embodiment of the method described herein is for screening of patients for an implantable pulse generator. Because this embodiment utilizes the RAND short form 36 questionnaire, or a comparable or otherwise suitable psychometric instrument, it leads to the conclusion that the ability and readiness to change one's lifestyle is important in this therapy. Because this change is essential for any permanent weight loss, it is likely that this same method may apply to any obesity therapy. Therefore, this invention is not limited to only implantable pulse generator therapy, but to extends any obesity therapy, both surgical, such as gastric by pass, vertical banded gastroplasty, or banding with devices such as the LapBand marketed by Innamed or Swedish Band marketed by Johnson & Johnson, and non-surgical, such as behavioral modification therapy, pharmaceutical therapy, or low calorie or very low calorie (liquid fasting) dieting. Examples of pharmaceutical therapy include, e.g., drugs under development such as Axokine® by Regeneron, or Rimonbant by Sanofi, or even drugs on the market such as Orlistat or Subutramine. Cocktails of one or more drugs used in combination, or drugs used with implantable devices, are further examples. Further, while the optimal implantable pulse generator therapy may be the pacing of the stomach in many situations, the placement of the implantable pulse in embodiments of the present invention extends to generator therapy for obesity including, but not limited to, the stimulation of the stomach, vagus nerve, intestines, brain, spinal cord, and other nerves of an animal body, including the sympathetic nerves.

Additionally, it is believed that the method of data mining and regression tree analysis described herein has not been previously observed as a screening tool for the implantation of other medical devices, including those outside the field of obesity or weight loss. Society may soon become very discerning as to whether even good medical device therapies may be reimbursed by third party payers such as insurance companies or governmental agencies. Evidence in advance of any implantation, to point to the degree of efficacy may be required to gain reimbursement. Thus, a proven scientific screening or optimization tool such as the disclosed method described herein offers a solution. It will be appreciated then that this invention applies to any similar screening or optimization tool developed on data mining and advanced regression tree analysis utilized in any device implantation without any particular limitation. A number of medical device therapies can be contemplated in this respect and, while not intending to limit the scope of this patent, can be shown as examples.

As an example, other implantable neuro-stimulators, such as those used to stimulate the spinal cord for chronic pain, or those used to stimulate the vagus nerve for depression or epilepsy, or those used to stimulate the brain for Parkinsons' disease, are all quite expensive and almost all effective on only a certain percentage or portion of the patients involved. Examples of these devices include those from Medtronic, Inc., Advanced Neuromodulation Systems, Inc. and Cyberonics, Inc.

Another example may involve the implant of drug coated coronary artery stents, such as those currently marketed by Cordis, a unit of Johnson & Johnson. These stents are currently expensive and in short supply. Another embodiment of the disclosed algorithm herein may be utilized to screen the best patients to receive the available devices.

Yet another example is the dual ventricular heart pacing devices designed to synchronize the ventricles and combat congestive heart failure, such as those sold by Guidant and Medtronic. Input data into the algorithm could change from the SF-36 to the size of the left ventricle, the ejection fraction of the patient, years in CHF, the immediate real time improvement of cardiac output upon temporary pacing, and other concurrent hemodynamic or electrophysiological diagnoses, such as the presence of atrial fibrillation.

Additionally, while the disclosed method is used for decision making prior to an implemented therapy in an important embodiment thereof, it should be noted that this invention is not limited entirely to pre-implant of a device. Once a device is implanted, the algorithm may be used with a change in input parameters of course, to determine a change in the way the implant works. For example, the implantable pulse generators today are mostly all programmable by a means external to the body. Similarly, a good number of the implantable drug pumps can be altered as to the amount of output from such pumps. Rather than change the output of these devices by a trial and error basis, which may cost valuable time in a diseased patient, or result in a potential overdose, the change in therapy can be more scientific by utilizing the described data mining and advanced regression tree analysis as described herein but with an altered embodiment. Thus, the present invention also covers methods of alterations of treatment within an already implanted device. Additionally, while this method has been shown to be useful in the implantation of a medical device, it should be noted that this invention is not limited to use with a medical device. It also is specifically contemplated that this invention be used to screen or optimize all medical therapies, including pharmaceutical, for example only, and not by way of limitation, biologics, natural medicines, gene therapy, stem cell therapies, and radiation therapies, among others.

All patents, patent applications, and publications disclosed herein are fully incorporated herein by reference for all purposes.

In the foregoing specification, various embodiments have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for predicting weight loss outcome of application of a proposed therapy to a patient for treating an eating, gastrointestinal, or gastroesophageal disorder, comprising:
   a) obtaining items of information from the patient at risk of the eating, gastrointestinal, or gastroesophageal disorder, each item of information relating to a preselected patient variable; and
   b) predicting the weight loss outcome for the patient from the obtained items of information for the patient using an aggregated weight loss predictor developed from i) observed similar types of information and corresponding weight loss information obtained from an actual population of patients who previously received a similar therapy to the proposed therapy for the patient, or ii) information generated from a simulated population of patients by resampling the observed actual population information to produce pseudo-replicates;
   wherein predicting the weight loss outcome comprises processing the items of information using an aggregated classification and repression tree model formed using a committee or ensemble method combining multiple predictors trained in perturbed versions of the observed similar types of information and corresponding weight loss information obtained from the actual population of patients.

2. The method of claim 1, where the proposed therapy is applied through the use of an implantable pulse generator.

3. The method of claim 1, where the proposed therapy is application of a banding type device.

4. The method of claim 1, where the proposed therapy is a bariatric type surgery.

5. The method of claim 1, where the proposed therapy is a non-surgical behavioral modification.

6. The method of claim 1, where the proposed therapy is a pharmaceutical or medicinal therapy.

7. The method of claim 1, wherein the committee or ensemble method is selected from the group consisting of a boosting algorithm, a bagging algorithm, and an arcing algorithm.

8. The method of claim 1, further comprising training the aggregated classification and regression tree model by preprocessing i) historical data comprising actual patient information of patients who previously received similar therapy to the proposed therapy for the patient, and ii) the corresponding weight loss outcomes of the patients who previously received similar therapy to learn how to predict weight loss outcomes.

9. The method of claim 8, wherein the preprocessing comprises:
   reducing quantity of the historical data and corresponding patient weight loss outcomes of patients who previously received similar therapy;
   reducing number of variables contained in the historical data and corresponding patient weight loss outcomes of patients who previously received similar therapy;
   transforming the historical data and corresponding patient weight loss outcomes of patients who previously received similar therapy using classification and regression trees;
   applying the boosting algorithm or the bagging algorithm; and
   generating the classification and regression tree model to predict the weight loss outcome.

10. The method of claim 8, further comprising testing the trained aggregated classification and regression tree model through a cross-validating procedure that comprises the steps of:
   1) randomly dividing the historical data and the corresponding weight loss outcomes of the patients who previously received similar therapy into a training set and a hold out test set;
   2) repeatedly training the model using perturbed versions of the randomly selected training set by the committee or ensemble method selected from the group consisting of the boosting algorithm and the bagging algorithm to obtain resulting predictors;
   3) applying each of the resulting predictors to the hold-out test set, and aggregating predictions by averaging and majority voting for use in screening test set subjects to determine their suitability for treatment;
   4) repeating steps 1), 2) and 3) at least once; and
   5) averaging at least one outcome statistic of interest for screening test set subjects, and
   6) using results of step 5) to assess usefulness of the model for improving expected treatment outcomes.

11. The method of claim 8, wherein the aggregated classification and regression tree model includes a combination of many distinct trees, each estimated in a sequence of systematically or randomly perturbed version of the historical data and the corresponding weight loss outcomes of the patients who previously received similar therapy, and wherein a screening decision for the patient is then based on a combination of average predicted weight loss across distinct trees or a majority vote criterion comprising whether a majority of the distinct trees predict weight loss above a predetermined threshold level.

12. The method of claim 1, wherein the items of information include psychometric data.

13. The method of claim 12, wherein the psychometric data include answers by the patient to questions asked in a RAND Short Form 36 (SF-36) health survey.

14. The method of claim 1, wherein the items of information are selected from at least one of symptoms, demographics, tests of psychological well being, family history, eating habits, diet, exercise, and other attempted weight loss therapies.

15. The method of claim 1, wherein the items of information comprises anthropometric data.

16. The method of claim 1, wherein the items of information comprises biomarker data.

17. The method of claim 1, wherein the items of information includes body mass index.

18. The method of claim 1, wherein the items of information includes RAND scores calculated for answers made by the patient to questions asked in a RAND Short Form 36 (SF-36) health survey (version 1.0), and anthropometric data of the patient including at least one of the patient's height, weight, sex, and age.

19. The method of claim 1, wherein the predicting comprises comparing the items of information to similar data gathered from an actual or simulated patient population for which results to an obesity therapy have been precollected or precalculated, respectively, effective to permit a classification of the patient in terms of a probable outcome to the proposed therapy, and wherein the proposed therapy is the obesity therapy.

20. The method of claim 19, wherein the processing and the comparing are at least partially performed by a computer.

21. The method of claim 19, further comprising rendering a decision as to whether or not to apply the proposed therapy based on the classification of the patient.

22. The method of claim 1, wherein the disorder is obesity, metabolic syndrome, or their related comorbidities.

23. The method of claim 22, wherein the disorder comprises at least one of the related comorbidities selected from the group consisting of high blood pressure, hypertension, high blood cholesterol, dyslipidemia, Type 2 diabetes, insulin resistance, glucose intolerance, hyperinsulinemia, coronary heart disease, angina pectoris, congestive heart failure, stroke, gallstones, cholesystitis, cholelithiasis, gastroesophageal reflux disease, gout, osteoarthritis, obstructive sleep apnea, sleep apnea complications related to pregnancy, cancer, menstrual irregularities, infertility, irregular ovulation, stress incontinence, uric acid nephrolithiasis, depression, eating disorders, distorted body image, and low self esteem.

24. The method of claim 1, wherein steps a) and b) are performed before, during, or after an animal clinical trial to demonstrate safety or efficacy of a medicinal therapy or medical device.

25. The method of claim 1, wherein the items of information comprise biomarker information selected from the group consisting of hormone information, peptide information, genomics information, and body scan information.

26. The method of claim 1, wherein the items of information comprise biomarker information selected from the group consisting of ghrelin peptide information, blood glucose measurements, and hemoglobin AIC information.

27. A method of screening or optimization of a prospective patient in advance of a medical treatment, comprising:
   a) developing a predictive model for outcomes of patients who will receive the medical treatment as part of a therapy or treatment of a medical condition or disorder, using data mining techniques, and advanced regression tree analysis to build, train and test the predictive model for predicting the outcomes of patients receiving the medical treatment;
   b) collecting data from the prospective patient for the medical treatment;
   c) using the predictive model to predict the possible outcome of the prospective patient for the medical treatment.

28. A method of claim 27, where such screening or optimization uses scoring from a lifestyle, quality of life, mental health or mental well-being being questionnaire taken by the prospective patient.

29. The method of claim 27, wherein the medical treatment comprises the implantation of a medical device in the prospective patient.

30. The method of claim 27, wherein the medical treatment comprises applying a pharmaceutical regimen to the prospective patient.

31. The method of claim 27, wherein the medical treatment comprises applying a medicinal regimen to the prospective patient.

32. The method of claim 27, wherein steps a), b), and c) are performed before, during, or after an animal clinical trial to demonstrate safety or efficacy of a medicinal therapy or medical device.

33. A method of screening or optimization of a prospective patient in advance of the application of an obesity therapy, comprising:
   a) developing a predictive model for outcomes of patients who will have the obesity therapy as part of a treatment for obesity and comorbidities thereof, using data mining techniques, and advanced regression tree analysis to build, train and test the predictive model for predicting the outcomes of patients receiving the obesity therapy;
   b) collecting data from the prospective patient for the obesity therapy;
   c) using the predictive model to predict the possible outcome of the prospective patient for the obesity therapy.

34. A method of claim 33, wherein the screening or optimization uses scoring from a lifestyle, quality of life, mental health or mental well-being questionnaire taken by the prospective patient.

35. The method of claim 34, wherein the questionnaire contains between about 20 and about 60 individual indications for response.

36. The method of claim 35, wherein the questionnaire is the RAND SF-36 form.

37. The method of claim 33, wherein the obesity therapy comprises a surgical procedure.

38. The method of claim 33, wherein the obesity therapy comprises installing an implantable gastric stimulator.

39. The method of claim 33, wherein the obesity therapy comprises bariatric surgery.

40. The method of claim 39, wherein the obesity therapy further comprises treatment of at least one of the comorbidities selected from the group consisting of high blood pressure, hypertension, high blood cholesterol, dyslipidemia, Type 2 diabetes, insulin resistance, glucose intolerance, hyperinsulinemia, coronary heart disease, angina pectoris, congestive heart failure, stroke, gallstones, cholesystitis, cholelithiasis, gastroeophageal reflux disease, gout, osteoarthritis, obstructive sleep apnea, sleep apnea complications related to pregnancy, cancer, menstrual irregularities, infertility, irregular ovulation, stress incontinence, uric acid nephrolithiasis, depression, eating disorders, distorted body image, and low self esteem.

41. The method of claim 33, wherein the obesity therapy comprises a pharmaceutical regimen.

42. The method of claim 33, wherein the obesity therapy comprises a medicinal regimen.

43. The method of claim 33, wherein steps a), b), and c) are performed before, during, or after an animal clinical trial to demonstrate safety or efficacy of a surgical procedure, medicinal therapy, or medical device.

* * * * *

UNITED STATES PATENT AND TRADEMARK OFFICE
CERTIFICATE OF CORRECTION

PATENT NO. : 7,194,301 B2 Page 1 of 1
APPLICATION NO. : 10/955591
DATED : March 20, 2007
INVENTOR(S) : Jenkins et al.

It is certified that error appears in the above-identified patent and that said Letters Patent is hereby corrected as shown below:

On the Title Page:

Item (73) Assignee: Change "Transeuronic" to -- Transneuronix --;

First Page, Column 2 (U.S. Patent Documents), Line 4: Change "Bonissone" to -- Chen --;

In the Claims:

Claim 1, Column 47, Line 35: Change "repression" to -- regression --;

Claim 23, Column 49, Lines 22-23: Change "gastroeophageal" to -- gastroesophageal --;

Claim 28, Column 49, Line 57: After "well-being" delete "being";

Claim 40, Column 50, Line 48: Change "gastroeophageal" to -- gastroesophageal --.

Signed and Sealed this

Twenty-first Day of August, 2007

JON W. DUDAS
*Director of the United States Patent and Trademark Office*